United States Patent
Chang et al.

(10) Patent No.: US 9,474,759 B2
(45) Date of Patent: Oct. 25, 2016

(54) BROAD-SPECTRUM ANTIVIRALS AGAINST 3C OR 3C-LIKE PROTEASES OF PICORNAVIRUS-LIKE SUPERCLUSTER: PICORNAVIRUSES, CALICIVIRUSES AND CORONAVIRUSES

(71) Applicants: Kansas State University Research Foundation, Manhattan, KS (US); The Ohio State University, Columbus, OH (US); Wichita State University, Wichita, KS (US)

(72) Inventors: Kyeong-Ok Chang, Manhattan, KS (US); Yunjeong Kim, Manhattan, KS (US); William C. Groutas, Wichita, KS (US); Duy Hua, Manhattan, KS (US); Linda J. Saif, Wooster, OH (US)

(73) Assignees: Kansas State University Research Foundation, Manhattan, KS (US); The Ohio State University, Columbus, OH (US); Wichita State University, Wichita, KS (US)

( * ) Notice: Subject to any disclaimer, the term of this patent is extended or adjusted under 35 U.S.C. 154(b) by 0 days.

(21) Appl. No.: 14/347,756

(22) PCT Filed: Sep. 27, 2012

(86) PCT No.: PCT/US2012/057609
§ 371 (c)(1),
(2) Date: Mar. 27, 2014

(87) PCT Pub. No.: WO2013/049382
PCT Pub. Date: Apr. 4, 2013

(65) Prior Publication Data
US 2014/0243341 A1 Aug. 28, 2014

Related U.S. Application Data

(60) Provisional application No. 61/641,552, filed on May 2, 2012, provisional application No. 61/539,810, filed on Sep. 27, 2011.

(51) Int. Cl.
| | |
|---|---|
| *A61K 38/06* | (2006.01) |
| *A61K 31/5377* | (2006.01) |
| *A61K 31/4015* | (2006.01) |
| *A61K 31/422* | (2006.01) |
| *A61K 31/427* | (2006.01) |
| *A61K 45/06* | (2006.01) |
| *C07D 207/27* | (2006.01) |

(52) U.S. Cl.
CPC ....... *A61K 31/5377* (2013.01); *A61K 31/4015* (2013.01); *A61K 31/422* (2013.01); *A61K 31/427* (2013.01); *A61K 38/06* (2013.01); *A61K 45/06* (2013.01); *C07D 207/27* (2013.01); *C12N 2770/16011* (2013.01); *C12N 2770/20011* (2013.01); *C12N 2770/32111* (2013.01); *C12N 2770/32311* (2013.01); *C12N 2770/32411* (2013.01); *C12N 2770/32611* (2013.01)

(58) Field of Classification Search
None
See application file for complete search history.

(56) References Cited

U.S. PATENT DOCUMENTS

| | | |
|---|---|---|
| 5,856,530 A | 1/1999 | Webber et al. |
| 6,649,639 B2 | 11/2003 | Dragovich et al. |
| 2006/0014821 A1 | 1/2006 | He et al. |

FOREIGN PATENT DOCUMENTS

| | | |
|---|---|---|
| WO | 97/43305 | 11/1997 |
| WO | 99/31122 | 6/1999 |
| WO | 01/10894 | 2/2001 |
| WO | 02/18369 | 3/2002 |
| WO | 2006061714 | 6/2006 |
| WO | WO 2006061714 A2 * | 6/2006 |

OTHER PUBLICATIONS

Kim, Yunjeong et al, "Broad-spectrum antivirals against 3c or 3c-like proteases of picornaviruses, noroviruses, and coronaviruses." J. Virol. (2012) 86(21) p. 11754-11762.*
Tiew, Kok-Chuan et al, "Design, synthesis, and evaluation of inhibitors of norwalk virus 3c protease." Bioorg Med. Chem. Lett (2011) 21 p. 5315-5319.*
Sarma, Diganta et al, "Synthesis of tripeptide-type sars-cov 3clpro inhibitors with a highly electrophilic carbonyl group." Peptide Science (2010) 46 p. 311-314.*
Sarma, Diganta et al, "SYnthesis fo tripeptide-type sars-cov 3clpro inhibitors with a highly electrophilic carbonyl group." Peptide Sci. (2010) 46 p. 311-314.*
International Search Report and Written Opinion dated Mar. 15, 2013, in the corresponding PCT/US2012/057609 application filed Sep. 27, 2012.
European Search Report dated May 21, 2015, in the corresponding EP 12837222.4 application filed Mar. 25, 2014.
Sivakoteswara Rao Mandadapu, "Potent Inhibitors of Norovirus 3CL Protease by Peptidyl Alfa-Ketoamides and Alfa-Ketoheterocycles," Bioorganic & Medicinal Chemistry Letters, 2012, pp. 4820-4826, vol. 22.

(Continued)

*Primary Examiner* — Maury Audet
*Assistant Examiner* — Fred Reynolds
(74) *Attorney, Agent, or Firm* — Hovey Williams LLP

(57) ABSTRACT

Antiviral protease inhibitors, including peptidyl aldehydes, peptidyl α-ketoamides, peptidyl bisulfate salts, and peptidyl heterocycles, are disclosed, along with related antiviral compounds, and methods of using the same to treat or prevent viral infection and disease. The compounds possess broad-spectrum activity against viruses that belong to the picornavirus-like supercluster, which include important human and animal pathogens including noroviruses, enteroviruses, poliovirus, foot-and-mouth disease virus, hepatitis A virus, human rhinovirus (cause of common cold), human coronavirus (another cause of common cold), transmissible gastroenteritis virus, murine hepatitis virus, feline infectious peritonitis virus, and severe acute respiratory syndrome coronavirus.

20 Claims, 23 Drawing Sheets

(56) References Cited

OTHER PUBLICATIONS

Rajendra P. Jain, "Synthesis and Evaluation of Keto-Glutamine Analogues as Potent Inhibitors of Severe Acute Respiratory Syndrome 3CL PRO," Journal of Medical Chemistry, Dec. 2, 2004, vol. 47, No. 25.

Kan X. Wu, "Developments Towards Antivirals Therapies Against Enterovirus 71." Drug Discovery Today, Dec. 2010, vol. 15, No. 23-24.

Prior, Allan M. "Design, synthesis, and bioevaluation of viral 3C and 3C-like protease inhibitors," Bioorganic & Medicinal Chemistry Letters, 2013, vol. 23, pp. 6317-6320.

Mandadapu, Sivakoteswara Rao, "Inhibition of norovirus 3CL protease by bisulfite adducts of transition state inhibitors," Bioorganic & Medicinal Chemistry Letters, 2013, vol. 23, pp. 62-65.

Mandadapu, Sivakoteswara Rao, "Potent inhibition of norovirus by dipeptidyl a-hydroxyphosphonate transition state mimics," Bioorganic & Medicinal Chemistry Letters, 2013, vol. 23, pp. 5941-5944.

* cited by examiner

ORF1

| | 45K | 40K | 22K | 16K | 19K | 57K |
|---|---|---|---|---|---|---|
| | NS1-2 N-terminal | NS3 NTPase | NS4 P22 | NS5 VPg | NS6 3CLpro | NS7 RdRp |
| | Q/G | | Q/G | E/G | E/A | E/G |

| | P7 | P6 | P5 | P4 | P3 | P2 | P1 | / | P1' | P2' | P3' | P4' | P5' | P6' | P7' | SEQ ID NO: |
|---|---|---|---|---|---|---|---|---|---|---|---|---|---|---|---|---|
| NS1-2/NS3 | L | P | D | F | H | L | Q | | G | P | E | D | L | A | R | 17 |
| NS3/NS4   | Q | D | E | F | Q | L | Q | | G | P | T | Y | D | F | D | 18 |
| NS4/NS5   | P | S | D | A | V | P | E | | G | K | N | K | G | K | T | 19 |
| NS5/NS6   | N | E | K | I | N | F | E | | A | P | P | T | L | W | S | 20 |
| NS6/NS7   | E | G | E | T | A | L | E | | G | G | D | K | G | H | Y | 21 | warhead
(Z = H, COOR, CONHR, etc.)

| Inhibitor | Structure | IC$_{50}$ (μM) |
|---|---|---|
| A | 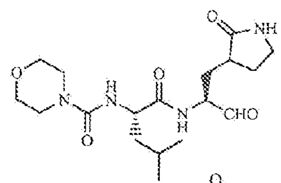 | 7.2 |
| B | 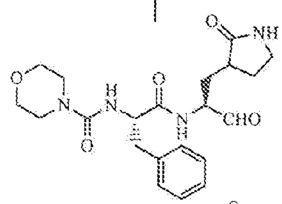 | Inactive[a] |
| C | 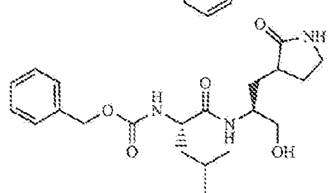 | Inactive[a] |
| D | 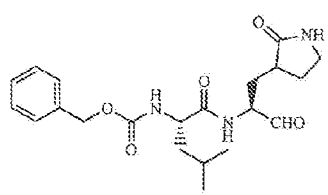 | 1.82 |
| E | 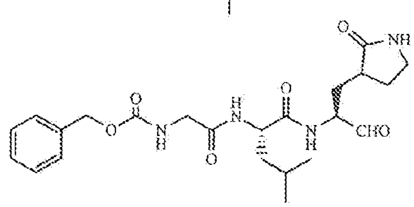 | 1.45 |
| F | 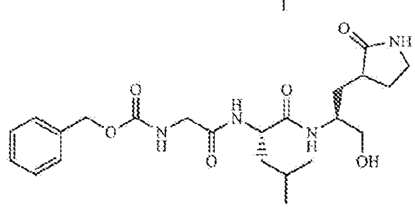 | Inactive[a] |

[a]Inhibitors were designated as inactive if the percent inhibition was < 25 when incubated with the enzyme for 30 minutes at an [ I ] / [ S ] ratio of 25.

Fig. 4

[a]Inhibitors were designated as inactive if the percent inhibition was < 25 when incubated with the enzyme for 30 minutes at an [ I ] / [ S ] ratio of 25.

| | Inhibition [IC$_{50}$ (µM)] against recombinant 3CLpro | | |
|---|---|---|---|
| | NV | MD145 | MNV-1 |
| GC373 | 0.64 | 1.18 | 1.34 |
| GC375 | 2.87 | 4.03 | 6.8 |
| GC376 | 0.50 | 0.96 | 1.12 |

|  | Inhibition [ED$_{50}$ (μM)] against various caliciviruses | | |
| --- | --- | --- | --- |
|  | HG23* | MNV-1 | FCV |
| GC373 | 0.3 | 6.5 | 65.1 |
| GC375 | 2.8 | >50 | >50 |
| GC376 | 0.2 | 5.3 | 35.2 |

* NV-replicon harboring cells

Fig. 10

| Drug | Inhibition [IC$_{50}$ (μM)] of recombinant 3Cpro or 3CLpro[a] | | | | | | | |
| --- | --- | --- | --- | --- | --- | --- | --- | --- |
|  | Caliciviruses | | Coronaviruses | | Picornaviruses | | | |
|  | NV | MD145 | TGEV | SARS-CoV | HAV | HRV | PV | FMDV |
| GC373 | 0.64±0.27 | 1.18±0.52 | 0.99±0.12 | 3.48±1.59 | >50 | 0.65±0.36 | 2.02±1.56 | 0.61±0.32 |
| GC375 | 2.87±0.39 | 4.02±2.19 | 1.55±0.10 | 4.66±0.19 | 42.59±2.61 | 0.55±0.39 | 2.84±0.25 | 0.55±0.32 |
| GC376 | 0.49±0.05 | 0.96±0.65 | 0.82±0.47 | 4.35±0.47 | >50 | 0.20±0.14 | 1.77±0.31 | 1.16±0.75 |
| Rupintrivir | 0.83±0.19 | 0.70±0.19 | >50 | >50 | >50 | 0.34±0.05 | 1.83±0.38 | 4.21±1.97 |

[a] The IC$_{50}$s are mean ± standard errors of the means for two or three independent tests with each optimized protease assay.

Fig. 11

| Drug | Inhibition (IC$_{50}$[µM]) against virus (mean±SEM)[a] | | | | | | | | | |
|---|---|---|---|---|---|---|---|---|---|---|
| | Caliciviruses | | Coronaviruses | | | | | Picornaviruses | | |
| | FCV | MNV-1 | TGEV | FIPV | MHV | 229E | BCV | HAV | EV71 | PTV | CoxB |
| GC373 | 65.1±2.1 | 6.5±1.2 | 0.3±0.2 | 0.3±0.1 | 2±0.2 | 0.2±0.1 | 0.7±0.2 | >100 | 11.1±1.2 | 0.15±0.1 | 0.2±0.1 |
| GC375 | >50 | >50 | 0.2±0.1 | 1.5±0.3 | 4.5±0.4 | 0.25±0.1 | 0.8±0.2 | 19.5±2.1 | 15.2±1.3 | 0.2±0.1 | 0.3±0.1 |
| GC376 | 35.2±3.6 | 5.3±1.6 | 0.15±0.1 | 0.2±0.1 | 1.1±0.3 | 0.15±0.1 | 0.6±0.2 | 50.2±5.6 | 10.3±2.4 | 0.15±0.1 | 0.15±0.1 |
| Rupintrivir | >50 | >50 | 2.5±0.7 | 10.3±1.3 | >100 | 0.3±0.1 | 15.3±2.5 | >100 | 0.5±0.2 | 0.15±0.1 | x |

[a]The IC$_{50}$s are averages for 3 independent tests and determined by the TCID$_{50}$ method. SEM, standard error of the mean.

Fig. 12

Inhibition (IC$_{50}$[μM]) against various viruses (mean±SEM)[a]

| Drug | Caliciviruses | Picornaviruses | | |
|---|---|---|---|---|
| | HG23 | HRV18 | HRV51 | HRV68 |
| GC373 | 0.2±0.1 | 1.1±0.3 | 1.8±0.3 | 1.6±0.2 |
| GC375 | 2.8±0.3 | 0.09±0.03 | 0.08±0.02 | 0.07±0.02 |
| GC376 | 0.3±0.1 | 1.2±0.2 | 1.5±0.2 | 0.8±0.2 |
| Rupintrivir | 2.3±0.5 | 0.03±0.01 | 0.02±0.01 | 0.04±0.02 |

[a] The IC$_{50}$s are averages for 3 independent tests and were determined by real-time qRT-PCR. SEM, standard error of the mean.

|  |  | Cmax (ng/ml) | AUC | AUMC | MRT (hr) | Vc (ml) | Vss | CL (ml/hr) | ½-LIFE (hr) | % F |
|---|---|---|---|---|---|---|---|---|---|---|
| GC373 | IV* | 1946.6 | 6272.8 | 2774.5 | 0.5 | 0.0001 | 0.0001 | 0.0002 | 1.6 | |
| | PO | 51.2 | 250.0 | 43101.8 | 2.3 | N/A | N/A | 0.004 | 1.6 | 4 |
| GC375 | IV | 2178.3 | 4911.0 | 2774.50 | 1.30 | 0.10 | 0.10 | 0.0002 | 6.1 | |
| | PO | 248.1 | 767.7 | 4948.4 | 6.18 | N/A | N/A | 0.001 | 1.6 | 16 |
| GC376 | IV | 3718.5 | 53259.2 | 567104.0 | 0.1 | 0.00001 | 0.00001 | 0.00002 | 1.3 | |
| | PO | 58.5 | 1645.0 | 43101.8 | 2.30 | N/A | N/A | 0.001 | 4.6 | 3 |

* Each compound was administered to animals via oral or intravenous routes at a dose of 20 mg/Kg.

| Passage number | ED$_{50}$ (μM)* | | Selection conc. (μM) |
|---|---|---|---|
| | Trial #1 | Trial #2 | |
| 0 | 7.1 | 6.2 | 40 |
| - | - | - | - |
| 5 | 28.6 | 25.3 | 80 |
| - | - | - | - |
| 15 | 75.4 | 85.5 | 80 |
| * ED$_{50}$ values were determined at 30 hr after virus inoculation; # N/T: not tested | | | |

A

VPg
MNV VPg N122D
P3 position (VPg/3CLpro)

$$\text{IN/DFEA} \xrightarrow{\text{3CLpro}}$$
$$\xleftarrow{\text{VPg}}$$

Pro
MNV 3CLpro K147R

Z = CHO (Ia)
= (C=O) CONHR$^1$ (Ib)
= (C=O) heterocycle (Ic)

| Compound | Structure | IC$_{50}$(μM) | ED$_{50}$(μM) |
|---|---|---|---|
| 5a | 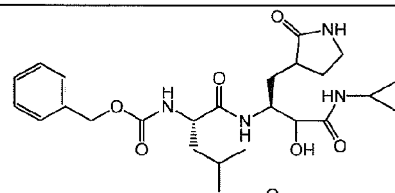 | 45.3 | 4.1 |
| 6a[42] | 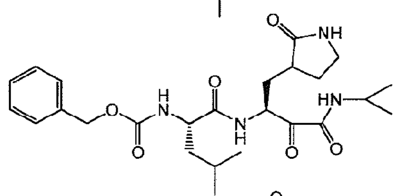 | 5.3 | 2.8 |
| 5b | 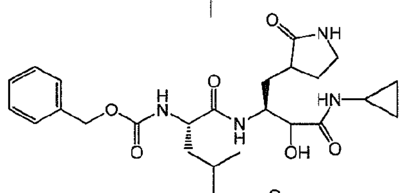 | >50 | >10 |
| 6b | 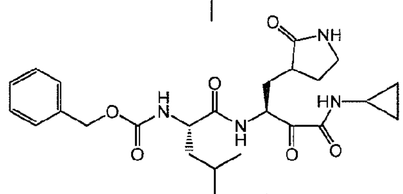 | 3.4 | 1.1 |
| 5c | 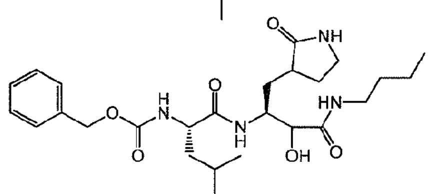 | >50 | >20 |
| 6c | 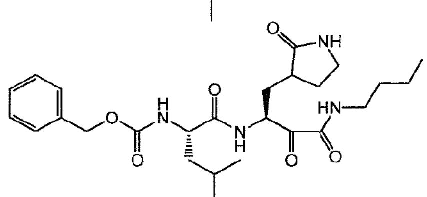 | 4.1 | 1.3 |
| 5d | 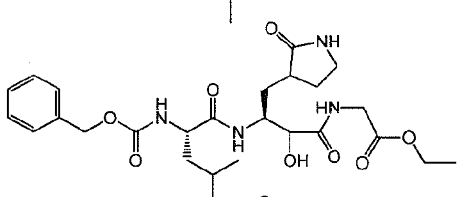 | >50 | >10 |
| 6d | 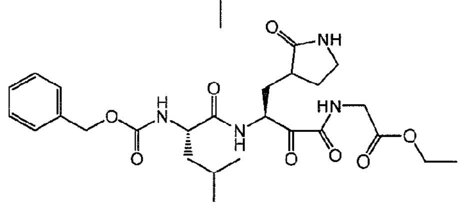 | 2.1 | 0.8 |

Fig. 23

| Compound | Structure | IC$_{50}$(μM) | ED$_{50}$(μM) |
|---|---|---|---|
| 5e | 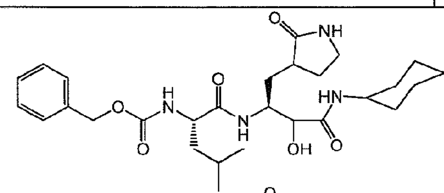 | >50 | >20 |
| 6e | 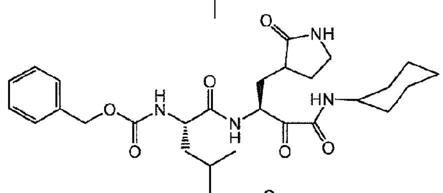 | 3.5 | 1.2 |
| 5f | 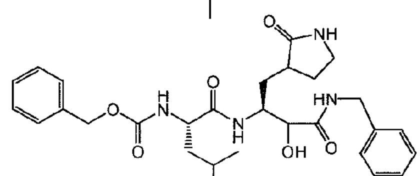 | >50 | >20 |
| 6f | 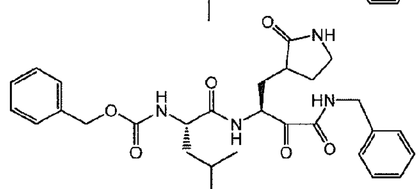 | 7.1 | 1.8 |
| 5g | 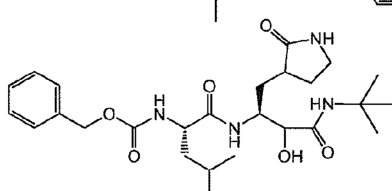 | >50 | >20 |
| 6g | 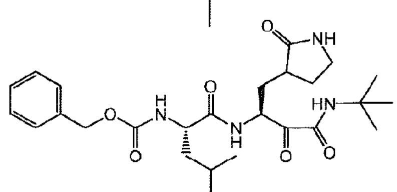 | 2.8 | 1.1 |
| 5h | 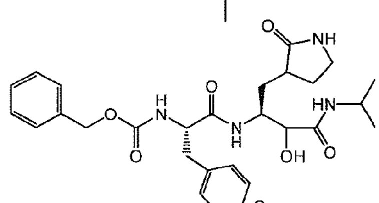 | 23.1 | 6.3 |
| 6h | 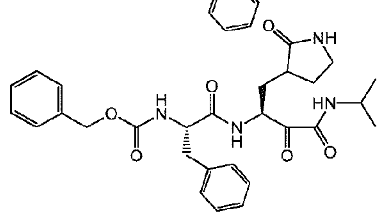 | 21.5 | 4.2 |

Fig. 23 (cont'd)

| Compound | Structure | IC$_{50}$(μM) | ED$_{50}$(μM) |
|---|---|---|---|
| 7a | 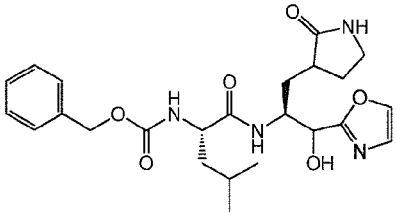 | >50 | >20 |
| 8a | 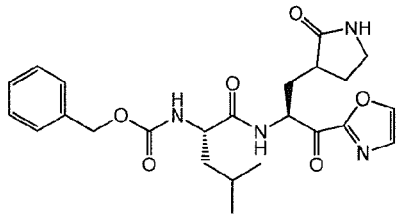 | 2.3 | 0.9 |
| 7b | 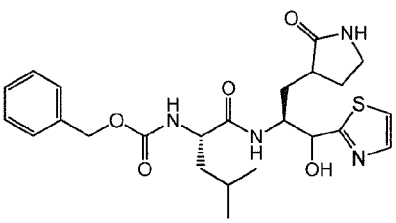 | 12.3 | 4.3 |
| 8b | 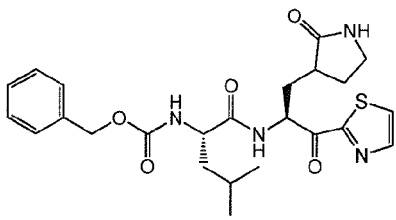 | 8.8 | 4.2 |
Fig. 23 (cont'd)

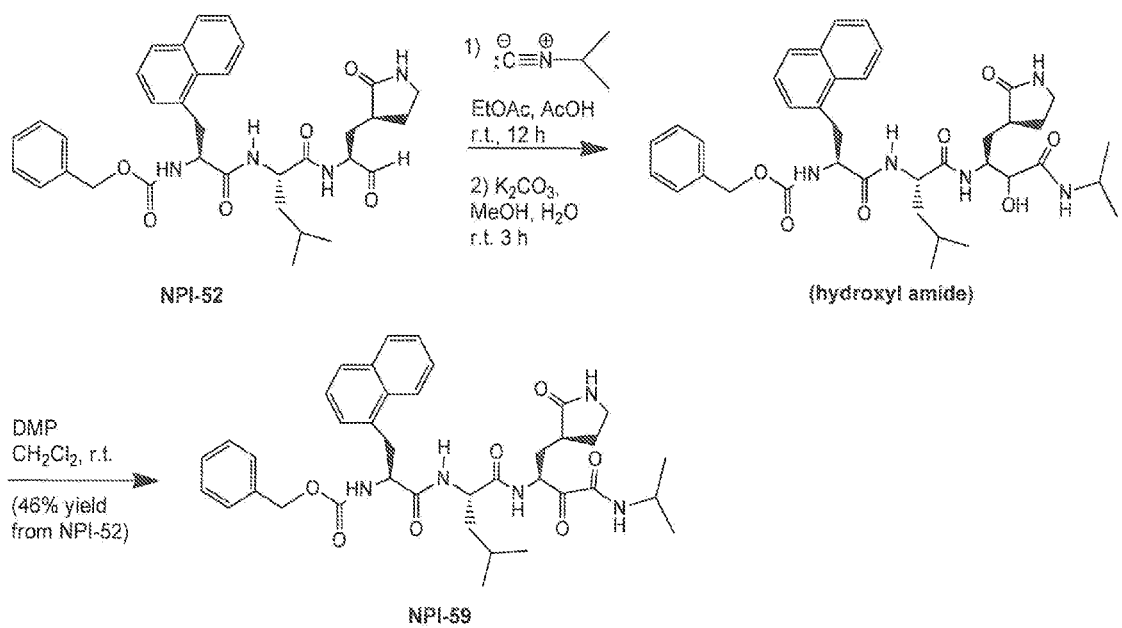

Fig. 31

| | Inhibition [IC$_{50}$ (μM)] against various viruses* | | | | | | | | | | | | | |
|---|---|---|---|---|---|---|---|---|---|---|---|---|---|---|
| | Calicivirus | | | Coronavirus | | | | | Picornavirus | | | | | |
| | HG23 | FCV | MNV-1 | TGEV | FIPV | MHV | 229E | BCV | HAV | HRV18 | HRV51 | HRV1B | EV71 | CB2 | PTV |
| NPI52 | 0.05 | 0.3 | 0.6 | 0.1 | 0.4 | 0.8 | 0.1 | ND | 25.5 | 0.015 | 0.03 | 0.07 | 0.4 | 0.01 | ND |
| NPI59 | 5.0 | > 50 | > 50 | 1.5 | 0.8 | 5.3 | 6.5 | ND | > 100 | 0.03 | 0.02 | 0.06 | 1.1 | 0.02 | ND |

* FCV: feline calicivirus; MNV-1: murine norovirus-1; TGEV: transmissible gastroenteritis virus; FIPV: feline infectious peritonitis virus; MHV: mouse hepatitis virus; 229E: human coronavirus 229E; MHV: BCV: bovine coronavirus; HAV: hepatitis A virus; EV71: Enterovirus 71; HRV 18, 51, 68: human rhinovirus 18, 51, 68 strains; CB2: coxsackievirus B2; PTV: porcine teschovirus. The IC50 values were averages of 3 independent tests, and determined by the TCID50 method for FCV, MNV-1, TGEV, FIPV, MHV, 229E, BCV, HAV, EV71 and PTV. Real time qRT-PCR was used for HG23 and HRV.

Fig. 32

BROAD-SPECTRUM ANTIVIRALS AGAINST 3C OR 3C-LIKE PROTEASES OF PICORNAVIRUS-LIKE SUPERCLUSTER: PICORNAVIRUSES, CALICIVIRUSES AND CORONAVIRUSES

CROSS-REFERENCE TO RELATED APPLICATIONS

The present application is the U.S. National Stage of PCT/US2012/057609, filed Sep. 27, 2012, which claims the priority benefit of U.S. Provisional Patent Application Ser. No. 61/539,810, filed Sep. 27, 2011, and Ser. No. 61/641,552, filed May 2, 2012, both entitled Novel Broad-Spectrum Antivirals against 3C or 3C-like Proteases of Picornavirus-like Supercluster: Picornaviruses, Noroviruses and Coronaviruses, and incorporated by reference in their entireties herein.

STATEMENT REGARDING FEDERALLY-FUNDED RESEARCH

This invention was made with U.S. Government support under grant number U01 AI081891 awarded by the National Institute of Health. The U.S. Government has certain rights in the invention.

SEQUENCE LISTING

The nucleic and amino acid sequences listed in the accompanying Sequence Listing are presented in accordance with 37 C.F.R. 1.822. Only one strand of each nucleic acid sequence is shown, but the complementary strand is understood as included by any reference to the displayed strand. The Sequence Listing is submitted as an ASCII computer readable text file, created on Sep. 18, 2012, 5 KB, which is incorporated by reference herein.

BACKGROUND OF THE INVENTION

1. Field of the Invention

The present invention relates to broad-spectrum antiviral compounds targeting the 3C or 3C-like proteases of the picornavirus-like supercluster.

2. Description of Related Art

Many viruses encode polyproteins with proteases which catalyze their subsequent cleavage to the mature functional proteins and are essential for viral replication. Previous attempts have been made to inhibit viral activity by targeting such proteases. However, most protease inhibitors have a short range of specificity that is genus-, species-, or even strain-specific due to structural variations in the viral proteases. Thus, broad spectrum antivirals are rare and have proven elusive to researchers.

Caliciviruses, such as the norovirus and sapovirus genera cause acute gastroenteritis in humans and animals. Noroviruses are the most common cause of acute viral gastroenteritis in the United States and worldwide, accounting for ~21 million cases of gastroenteritis in the U.S. alone. Noroviruses are highly contagious and cause outbreaks in enclosed settings such as navy and cruise ships, army barracks, schools, and hospitals. Noroviruses are very stable in the environment and refractory to many common disinfectants, with only a few virions required to initiate virus infection and shedding which could be a source for further contamination. Norovirus infection constitutes an important public health problem, as well as a potential bioterrorism threat, and is classified as a NIAID bioterrorism agent B. The problem is further compounded by the absence of specific norovirus antiviral therapeutics or vaccines. Vaccine development for human noroviruses faces additional obstacles because norovirus strain diversity is high, and immunity to one strain does not necessarily provide protection from infection with other strains. Furthermore, repeat infections with the same norovirus strain in adults indicate that long-term immunity may be absent. Thus, there is currently an urgent and unmet need for the development of antiviral therapeutics for the treatment and prevention of norovirus infection. There is also a need for antiviral therapies for treating and preventing other types of enteroviruses, as well as rhinoviruses.

SUMMARY OF THE INVENTION

In one aspect, an antiviral compound comprising formula I, or a pharmaceutically-acceptable salt thereof is provided:

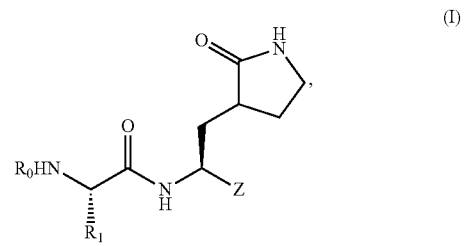

where: each $R_1$ is a branched or unbranched alkyl, cycloalkyl, aryl, arylalkyl, alkenyl, alkynyl, natural amino acid side chain, or a combination thereof; each $R_0$ is —C(O)R, —S(O)$_2$R or —(CH$_2$)$_n$R$_3$ where n=0-6; each R is selected from the group consisting of —OCH$_2$R$_3$ and —CH(—R$_4$)NHC(O)R$_5$; each $R_3$ is a substituted or unsubstituted: aryl, heteroaryl, aryloxy, heteroaryloxy, arylalkoxy, heteroarylalkoxy, or saturated heterocycle; each $R_4$ is a branched or unbranched alkyl, cycloalkyl, aryl, arylalkyl, alkenyl, alkynyl, natural amino acid side chain, or a combination thereof; and each $R_5$ is —OCH$_2$R$_3$ where $R_3$ is a substituted or unsubstituted: aryl, heteroaryl, aryloxy, heteroaryloxy, arylalkoxy, heteroarylalkoxy, or saturated heterocycle; and each Z is selected from the group consisting of aldehydes, ketoamides, bisulfite salts, heterocyclic moieties, —COCOOR$_2$ where $R_2$ is a branched or unbranched alkyl, —CH(OH)COOR$_2$ where $R_2$ is a branched or unbranched alkyl, and —CH(OH)(P=O)(OR$_6$)$_2$ where $R_6$ is an alkyl, alkenyl, arylalkyl, halogenated alkyl, or substituted or unsubstituted aryl.

A method of treating or preventing viral infection in a subject from one or more viruses selected from the group consisting of caliciviruses, picornaviruses, and/or coronaviruses is also provided. The method comprises administering to said subject a therapeutically-effective amount of a first antiviral compound according to the various embodiments described herein.

A broad spectrum antiviral composition is also disclosed. The composition comprises a first antiviral compound according to the various embodiments described herein dispersed in a pharmaceutically-acceptable carrier.

A kit is also provided herein. The kit comprises: an antiviral compound according to the various embodiments described herein; and instructions for administering the compound to a subject in need thereof.

A method of preventing or inhibiting replication of a virus in a cell is also disclosed. The method comprises contacting the cell with a compound according to the various embodiments described herein, wherein the virus is selected from the group consisting of caliciviruses, picornaviruses, coronaviruses, and combinations thereof.

The invention is also concerned with the use of a compound according to the various embodiments described herein to prepare a therapeutic or prophylactic medicament for the treatment or prevention of a viral infection from caliciviruses, picornaviruses, and/or coronaviruses in a subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure (FIG. 1) is an illustration of the genomic organization of norovirus (Norwalk virus) ORF1 with 3C-like (3CL) protease recognition sites;

FIG. 10 is a table showing the effects of GC373, 375, and 376 in the replication of NV, FCV, and MNV-1 in cell culture;

FIG. 11 is a table of the effects of GC373, 375, and 376 in the FRET protease assay using the 3C or 3CL proteases;

FIG. 12 is a table of the effects of GC373, 375, and 376 on replication of various viruses in cell culture;

FIG. 21 illustrates the mutations identified in MNV-1 passaged in the presence of GC376 showing (A) two mutations that were identified at VPg and 3CL protease; and (B) mutation K147R located at dII β-sheet of MNV 3CL protease (the structure in the panel is NV 3CL protease);

FIG. 22 is a general structure of disclosed protease inhibitors;

FIG. 23 is a table showing the results of the protease inhibition tests using the synthesized compounds in Example 4;

FIG. 31 illustrates the reaction scheme for synthesizing tripeptidyl compound NPI59; and FIG. 32 is the table of the results using the tripeptidyl compounds on various viruses in cell culture from Example 6.

DETAILED DESCRIPTION

Figures 1, 2:
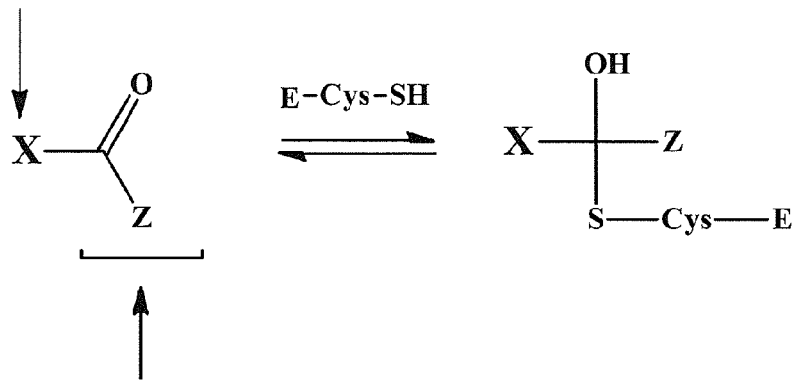
FIG. 2 is a general illustration of the interaction between a cysteine protease and a transition state inhibitor.

Among positive sense RNA viruses, genetic analysis has demonstrated that certain viruses can be classified as members of the picornavirus-like "supercluster," which includes picornaviruses, caliciviruses, and coronaviruses. A common feature of these viruses is that they possess a viral 3C or 3CL protease which is responsible for most cleavages of the corresponding viral polyprotein. These 3C and 3CL proteases share some common characteristics, including a typical chymotrypsin-like fold and a catalytic triad (or dyad) with Cys-His-Glu (or Asp) on the protease, and a preference for a Glu or Gln residue at the P1 position on the substrate. High resolution 3D structures of these proteases have confirmed the conservation of active sites with the catalytic triad or dyad and substrate binding pockets. Viruses in the picornavirus-like supercluster include important human and animal pathogens. For example, caliciviruses include noroviruses (Norwalk virus [NV]), feline calicivirus, MD145, murine norovirus [MNV], vesicular exanthema of swine virus, and rabbit hemorrhagic disease virus. Picornaviruses include enteroviruses (such as enterovirus 71), poliovirus, coxsackievirus, foot-and-mouth disease virus (FMDV), hepatitis A virus (HAV), porcine teschovirus, and rhinovirus (cause of common cold). Coronaviruses include human coronavirus (cause of common cold such as 229E strain), transmissible gastroenteritis virus (TGEV), murine hepatitis virus (MHV), bovine coronavirus (BCV), feline infectious peritonitis virus (FIPV), and severe acute respiratory syndrome coronavirus (SARS-Co). A series of novel protease inhibitors have been synthesized and demonstrated to possess broad-spectrum activity against viruses that belong to the picornavirus-like supercluster in enzyme and/or cell based assays. The efficacy of the compounds in an animal model of norovirus infection is also demonstrated. Members of this series of compounds are highly effective as antiviral therapeutics targeting a specific virus or, more importantly, they are broad-spectrum antivirals targeting multiple viruses. The wide applicability of the latter constitutes a significant advance in antiviral research and public health Embodiments described herein include antiviral compounds having broad-spectrum (multivalent) activity against viruses that belong to the picornavirus-like supercluster, including caliciviruses, picornaviruses and coronaviruses. The compounds are small-molecule based antivirals. The inventive compounds are peptidomimetics and include di- and tripeptidyl viral protease inhibitors which are highly effective against such viruses with low cytotoxicity. These compounds have broad-spectrum therapeutic value against multiple viruses of the picornavirus-like supercluster, which includes important classical and emerging animal and human pathogens. The compounds effectively target and inhibit viral 3C or 3CL protease activity across multiple virus species, strains, and subtypes, thereby preventing formation of the mature virus and inhibiting virus replication in the host cell. In some embodiments, the compounds are prodrugs that are converted into a active compounds that target and inhibit viral 3C or 3CL protease activity. The compounds have a therapeutic index (ratio of lethal or toxic dose to therapeutic dose) of greater than about 500:1, indicating the relative safety of such compounds for use in human and veterinary applications.

In some embodiments, antiviral compounds comprising (consisting essentially or even consisting of) formula (I), or the pharmaceutically-acceptable salt thereof, are provided:

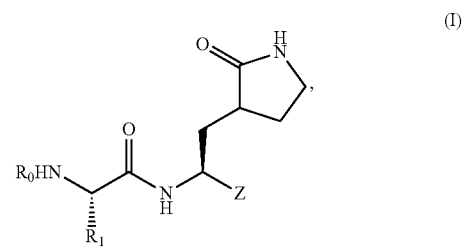

where each $R_1$ is a natural or non-naturally occurring amino acid side chain such as branched or unbranched alkyl (e.g., methyl, ethyl, butyl, isobutyl), cycloalkyl (e.g. cyclohexylmethyl), aryl (e.g., phenyl), arylalkyl (e.g. benzyl or group where the aryl is naphthyl), alkenyl (e.g. $(CH_2)_nCH=CH_2$ where n=1-4 and preferably 1) or alkynyl (e.g. $(CH_2)_nC\equiv CH$ where n=1-4 and preferably 1), or a combination thereof; each $R_0$ is —C(O)R, —S(O)$_2$R, or —(CH$_2$)$_n$R$_3$ where n=0-6 and preferably 1, each R is selected from the group consisting of —OCH$_2$R$_3$ and —CH(—R$_4$)NHC(O)R$_5$, where: each $R_3$ is a substituted or unsubstituted: aryl (e.g., phenyl), heteroaryl, aryloxy, heteroaryloxy, arylalkoxy, heteroarylalkoxy, or saturated heterocycle; each $R_4$ is an amino acid side chain (defined above); each $R_5$ is —OCH$_2$R$_3$ where $R_3$ is defined above; and each Z is selected from the group consisting of aldehydes (such as —CHO), ketoamides (such as —C(O)C(O)NHR$_2$ or —C(OH)C(O)NHR$_2$ where $R_2$ is a branched or unbranched alkyl (such as methyl, ethyl, butyl, isobutyl)), bisulfite salts (e.g., —CH(OH)SO$_3^-$Na$^+$), heterocylic moieties such as —C(O)-heterocycle or —CH(OH)-heterocycle where suitable heterocycles include thiazoles and/or oxazoles, —COCOOR$_2$ where $R_2$ is defined above, —CH(OH)COOR$_2$ where $R_2$ is defined above, and —CH(OH)(P=O)(OR$_6$)$_2$ where $R_6$ is an alkyl, alkenyl, arylalkyl, halogenated alkyl, or substituted or unsubstituted aryl. In preferred embodiments, moiety Z is attached directly to the molecule (alpha carbon). Suitable saturated or unsaturated ring substitutions mentioned above include cyanos, hydroxys, alkoxys, fluorine, and the like. The term "pharmaceutically-acceptable salt" refers to an acid or base salt of a compound of the invention, which salt possesses the desired antiviral activity and is neither biologically nor otherwise undesirable.

In some embodiments, the compounds are selected from the group consisting of formulas II, III, IV, V, VI, VII, VIII, or a pharmaceutically-acceptable salt thereof:

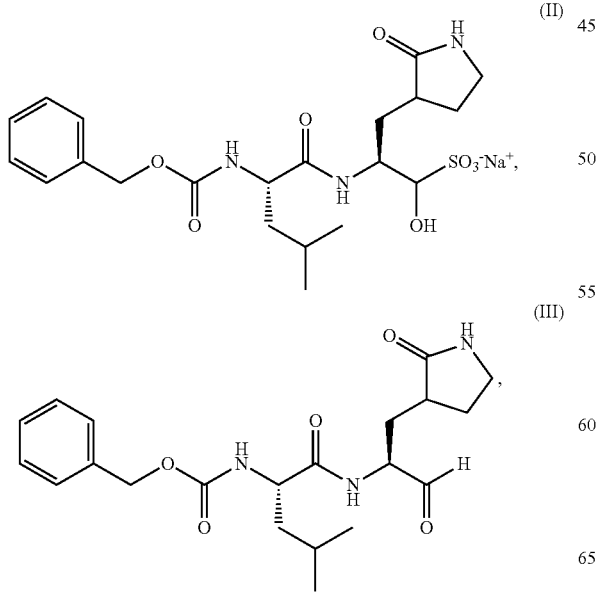

(II)

(III)

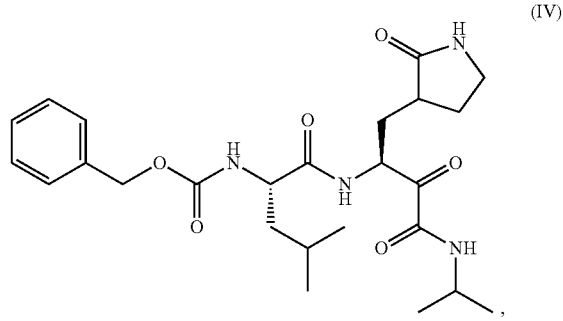

(IV)

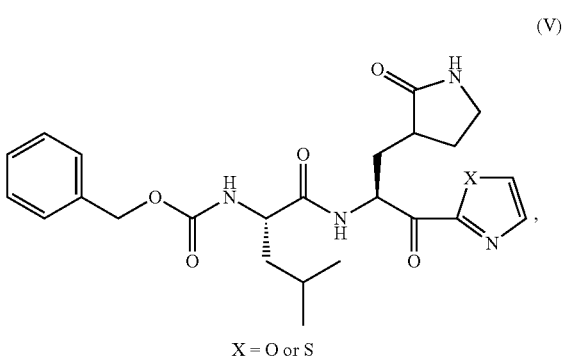

(V)

X = O or S

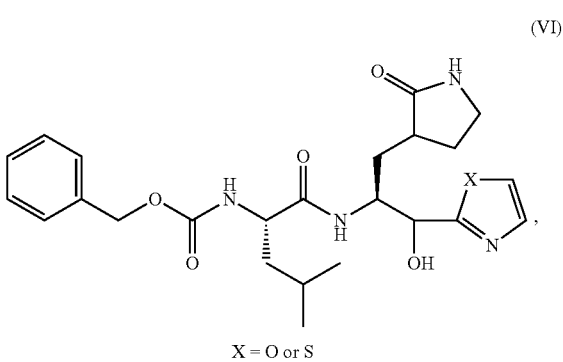

(VI)

X = O or S

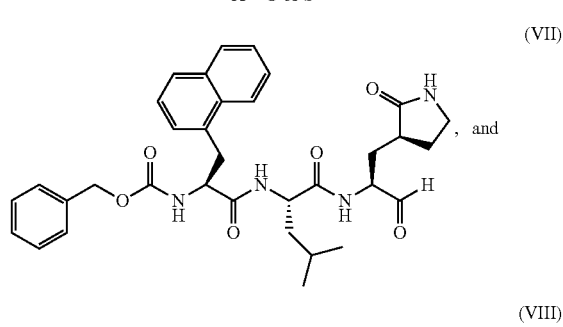

(VII), and

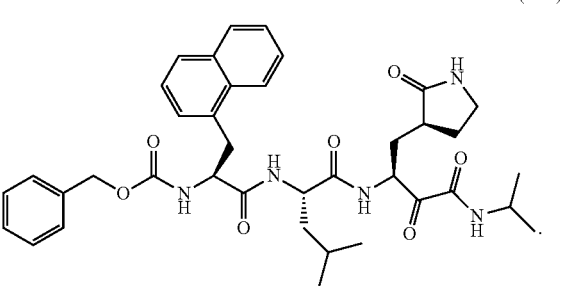

(VIII)

Combinations of one or more of the foregoing compounds can also be used in the invention.

Prophylactic and/or therapeutic compositions with specific or broad-spectrum antiviral activities are also disclosed. The compositions comprise an antiviral compound described herein dispersed in a pharmaceutically-acceptable carrier. The term carrier is used herein to refer to diluents, excipients, vehicles, and the like, in which the antiviral may be dispersed for administration. Suitable carriers will be pharmaceutically acceptable. As used herein, the term "pharmaceutically acceptable" means not biologically or otherwise undesirable, in that it can be administered to a subject without excessive toxicity, irritation, or allergic response, and does not cause unacceptable biological effects or interact in a deleterious manner with any of the other components of the composition in which it is contained. A pharmaceutically-acceptable carrier would naturally be selected to minimize any degradation of the compound or other agents and to minimize any adverse side effects in the subject, as would be well known to one of skill in the art. Pharmaceutically-acceptable ingredients include those acceptable for veterinary use as well as human pharmaceutical use, and will depend on the route of administration. For example, compositions suitable for administration via injection are typically solutions in sterile isotonic aqueous buffer. Exemplary carriers include aqueous solutions such as normal (n.) saline (~0.9% NaCl), phosphate buffered saline (PBS), sterile water/distilled autoclaved water (DAW), various oil-in-water or water-in-oil emulsions, as well as dimethyl sulfoxide (DMSO) or other acceptable vehicles, and the like.

The composition can comprise a therapeutically effective amount of the compound dispersed in the carrier. As used herein, a "therapeutically effective" amount refers to the amount that will elicit the biological or medical response of a tissue, system, or subject that is being sought by a researcher or clinician, and in particular elicit some desired therapeutic or prophylactic effect as against the viral infection by preventing and/or inhibiting 3C or 3CL protease activity and/or viral replication. One of skill in the art recognizes that an amount may be considered therapeutically "effective" even if the condition is not totally eradicated or prevented, but it or its symptoms and/or effects are improved or alleviated partially in the subject. In some embodiments, the composition will comprise from about 5% to about 95% by weight of an antiviral compound described herein, and preferably from about 30% to about 90% by weight of the antiviral compound, based upon the total weight of the composition taken as 100% by weight. In some embodiments, combinations of more than one type of the described antiviral compounds can be included in the composition, in which case the total levels of all such compounds will preferably fall within the ranges described above.

Other ingredients may be included in the composition, such as adjuvants, other active agents, preservatives, buffering agents, salts, other pharmaceutically-acceptable ingredients. The term "adjuvant" is used herein to refer to substances that have immunopotentiating effects and are added to or co-formulated in a therapeutic composition in order to enhance, elicit, and/or modulate the innate, humoral, and/or cell-mediated immune response against the active ingredients. Other active agents that could be included in the composition include other antiviral compounds (e.g., cathepsins) or any immunogenic active components (e.g., antigens) such as those that resemble a disease-causing microorganism or infectious agent, and/or are made from weakened or killed forms of the same, its toxins, subunits, particles, and/or one of its surface proteins, such that it provokes an immune response to that microorganism or infectious agent. In addition to live, modified, or attenuated vaccine components, active agents using synthetic peptides, carbohydrates, or antigens can also be used.

Compositions according to the embodiments disclosed herein are useful in treating and/or preventing viral infection from caliciviruses (noroviruses), picornaviruses, and/or coronaviruses in a subject. Thus, embodiments described herein have broad-spectrum therapeutic and/or prophylactic uses. The terms "therapeutic" or "treat," as used herein, refer to processes that are intended to produce a beneficial change in an existing condition (e.g., viral infection, disease, disorder) of a subject, such as by reducing the severity of the clinical symptoms and/or effects of the infection, and/or reducing the duration of the infection/symptoms/effects. The terms "prophylactic" or "prevent," as used herein, refer to processes that are intended to inhibit or ameliorate the effects of a future viral infection or disease to which a subject may be exposed (but is not currently infected with). In some cases the composition may prevent the development of observable morbidity from viral infection (i.e., near 100% prevention). In other cases, the composition may only partially prevent and/or lessen the extent of morbidity due to the viral infection (i.e., reduce the severity of the symptoms and/or effects of the infection, and/or reduce the duration of the infection/symptoms/effects). In either case, the compounds are still considered to "prevent" the target infection or disease.

In use, a therapeutically-effective amount of an antiviral compound is administered to a subject. In some embodiments, a composition comprising a therapeutically-effective amount of an antiviral compound is administered to a subject. Regardless, the compound or pharmaceutically acceptable salt thereof will preferably be administered to the subject in an amount sufficient to provide antiviral compound levels (independent of salt, if any) of from about 0.1 mg to about 1,000 mg of compound per kg of body weight of the subject, preferably from about 1 mg/kg to about 100 mg/kg of body weight of the subject, and more preferably from about 10 mg/kg to about 50 mg/kg of body weight of the subject. Thus, it will be appreciated that in the case of compound salts, for example, the formulation may be administered in amounts greater than the above ranges to provide sufficient levels of the active compound.

In some embodiments, the subject is afflicted with or suffering from a condition (e.g., infection, disease, or disorder) before the compounds are administered, wherein methods described herein are useful for treating the condition and/or ameliorating the effects of the condition. In other embodiments, the subject is free of a given condition before administering the compound, wherein the methods described herein are useful for preventing the occurrence or incidence of the condition and/or preventing the effects of the condition, as described above. The disclosed embodiments are suitable for various routes of administration, depending upon the particular carrier and other ingredients used. For example, the prophylactic and/or therapeutic compounds or compositions can be injected intramuscularly, subcutaneously, intradermally, or intravenously. They can also be administered via mucosa such as intranasally or orally. The compounds or compositions can also be administered through the skin via a transdermal patch.

In some embodiments, the compound or compositions can be provided in unit dosage form in a suitable container. The term "unit dosage form" refers to a physically discrete unit suitable as a unitary dosage for human or animal use. Each unit dosage form may contain a predetermined amount of the inventive compound (and/or other active agents) in the carrier calculated to produce a desired effect. In other embodiments, the compound can be provided separate from the carrier (e.g., in its own vial, ampule, sachet, or other suitable container) for on-site mixing before administration to a subject. A kit comprising the antiviral compound(s) is also disclosed herein. The kit further comprises instructions for administering the compound to a subject. The antiviral compound(s) can be provided as part of a dosage unit, already dispersed in a pharmaceutically-acceptable carrier, or it can be provided separately from the carrier. The kit can further comprise instructions for preparing the antiviral compounds for administration to a subject, including for example, instructions for dispersing the compounds in a suitable carrier.

It will be appreciated that therapeutic and prophylactic methods described herein are applicable to humans as well as any suitable animal, including, without limitation, dogs, cats, and other pets, as well as, rodents, primates, horses, cattle, pigs, etc. The methods can be also applied for clinical research and/or study. Additional advantages of the various embodiments of the disclosure will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described and claimed herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention. Except where noted, precursor, intermediate, and final compounds described in the synthesis reactions below are independently numbered in each Example.

Example 1

Design Synthesis and Evaluation of Inhibitors of Norwalk Virus 3C Protease

Noroviruses are a leading cause of food-borne and water-borne non-bacterial acute gastroenteritis. Norovirus infections constitute an important health problem with an estimated 23 million cases of gastroenteritis occurring annually in the U.S., causing 50,000 hospitalizations and 300 deaths. There are currently no effective vaccines or antiviral therapeutics for the treatment of norovirus infection.

Noroviruses are a small non-enveloped viruses of the Caliciviridae family. The genome of Norwalk virus, a prototype of noroviruses, consists of a single-stranded, positive sense RNA molecule of ~7.7 Kilo bases) that consists of three open reading frames (ORFs) that encode a 200 kDa polyprotein (ORF1), a major capsid protein VP1 (ORF2), and a small basic protein VP2 (ORF3). The mature polyprotein is co- and post-translationally processed by a virus-encoded protease to generate mature non-structural proteins. Processing of the mature polyprotein is mediated by the 3CL protease, a (chymo)trypsin-like cysteine protease having a Cys-His-Glu catalytic triad and an extended binding site. The substrate specificity of norovirus 3CL protease has been determined using in-vitro transcription/translation studies, or peptidyl chromogenic and fluorogenic substrates. The protease shows a strong preference for a -D/E-F/Y-X-L-Q-G- sequence (where X is H, E or Q) corresponding to the subsites S5-S4-S3-S2-S1-S1'-S2'-. (FIG. 1) Cleavage is at the P1-P1' (Q-G) scissile bond. X-ray crystal structures of norovirus 3CL protease alone or covalently-bound to an inhibitor, a peptidyl Michael acceptor, have been reported.

Norovirus 3CL protease plays an essential role in the virus replication, consequently, orally-bioavailable drug-like agents that inhibit the 3CL protease are of value as potential antiviral therapeutics. We describe herein the results of preliminary studies related to the inhibition of Norwalk virus 3CL protease by a series of peptidyl inhibitors (FIG. 2).

Figure 3:
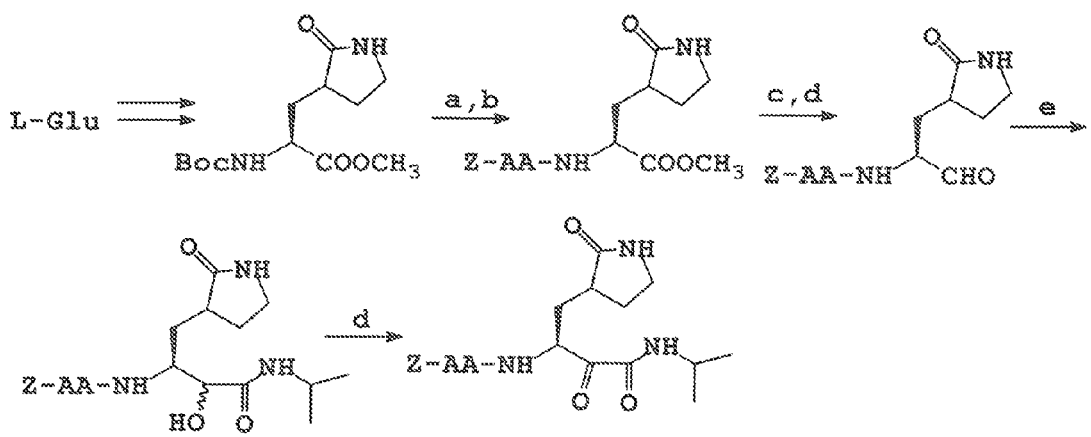
FIG. 3 shows a reaction scheme for the synthesis of inhibitors A-J in Example 1.

Initial design considerations included the use of a glutamine surrogate for optimal synthetic tractability and design flexibility. Furthermore, our overarching goal was to identify a suitably-functionalized di-peptide or tri-peptide inhibitor that could be further transformed into a molecule possessing molecular properties that are important for oral bioavailability and favorable ADME/Tox characteristics. The design of the inhibitors was further augmented by insights gained via the use of computer graphics and modeling and the X-ray crystal structure of the enzyme. The synthesis of inhibitors A-J was carried out as shown in Scheme 1 (FIG. 3). All compounds were characterized by 1H NMR and HRMS. The glutamine surrogate starting material was synthesized using literature procedures.

Deblocking with TFA, followed by coupling with an appropriate Cbz-protected amino acid ester, yielded a product which was subsequently reduced to the alcohol with lithium borohydride. Dess-Martin oxidation yielded the desired aldehydes. Alpha-ketoamide inhibitor J was synthesized by reacting the corresponding peptidyl aldehyde with isopropyl isonitrile in the presence of acetic acid, followed by mild hydrolysis of the diastereomeric acetate ester to yield the α-hydroxyamide, and Dess-Martin oxidation. The interaction of inhibitors A-J with Norwalk virus 3CL protease was then investigated.

Figure 4:
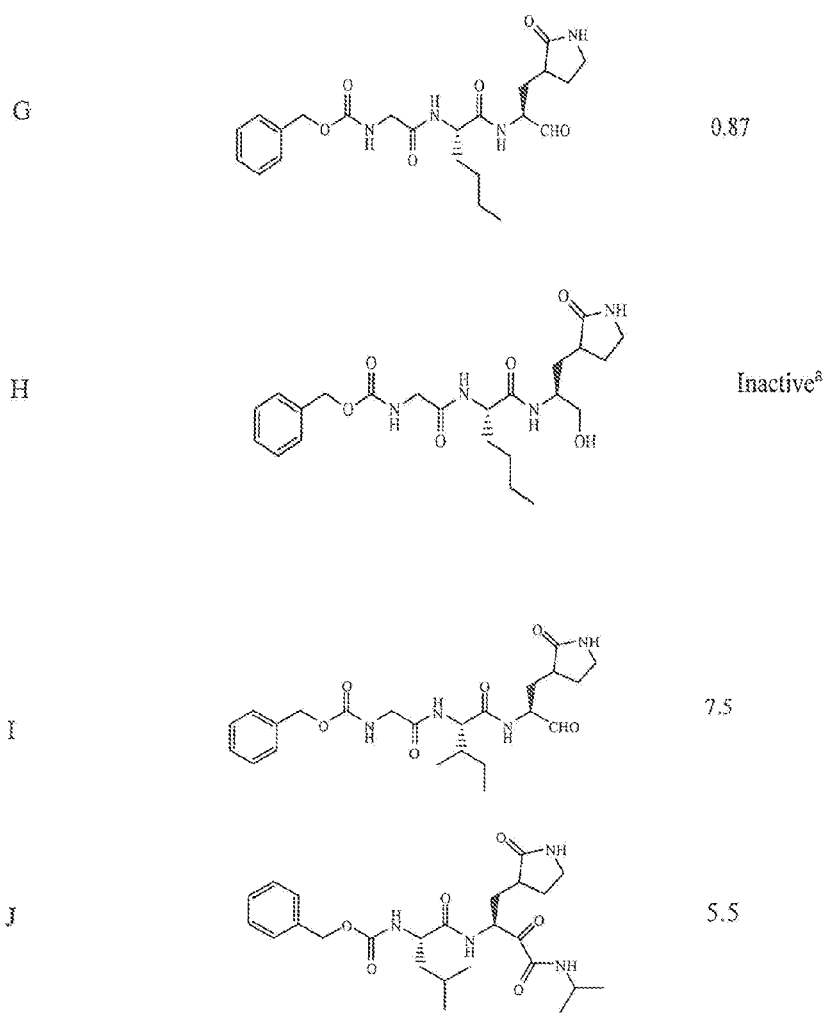
FIG. 4 is a table showing the results of the protease inhibition tests using the synthesized inhibitors in Example 1.
Figure 5:
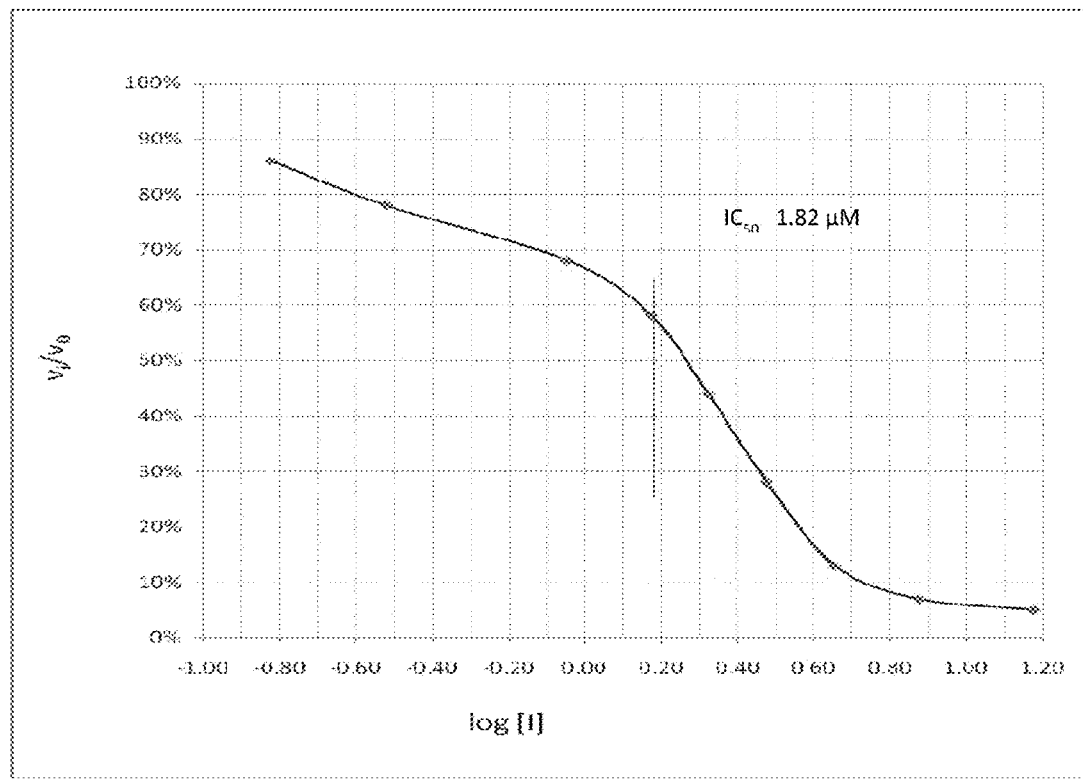
FIG. 5 is a graph of the Log dose-responsive curve for the inhibition of NV3CL protease by inhibitor E.
Figure 6:
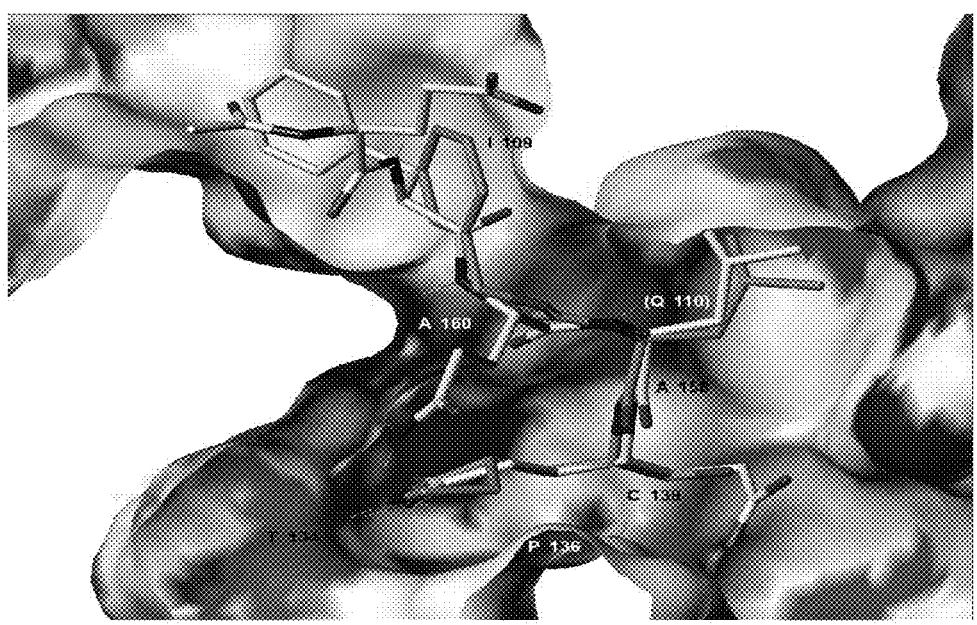
FIG. 6 is an illustration of the predicted covalently-bound conformer for NV3CL protease inhibitor C (stick structure with green carbon atoms and CPK-colored N and O atoms) contrasted with the peptide inhibitor (stick structure of green carbon atoms and CPK-colored N and O atoms) resolved in the 1IPH crystal structure. The NV3CL protease binding site is shown as a Connoly surface colored as follows: yellow=non-polar groups; white=partially polar C and H; red=polar O; blue=polar N; cyan=polar H. Key pharmacophore residues are labeled according to the positions on the receptor surface from which they interact with the ligand (except for Q110 whose approximate position is marked, but whose surface is not shown because the residue is above the plane of the molecule)

Recombinant NV protease was assayed as follows: In a typical inhibition run, 10 µL of 50 µM NV protease was added to a thermostatted cuvette at 30° C. containing 180 µL of 50 mM $NaH_2PO_4$ buffer, pH 8.0, containing 120 mM NaCl and 6 mM DTT, and 5 µL of inhibitor in DMSO. After a 30 minute incubation period, 5 µL of 12 µM Edans-EPDFHLQGPEDLAK-Dabcyl (SEQ ID NO:1) substrate in DMSO was then added and the increase in fluorescence was monitored for 30 minutes at an excitation and emission wavelength of 360 and 460 nm, respectively. Using a HORIBA FluoroMax 4 spectrofluorometer. Hydrolysis curves were linear. The final enzyme and substrate concentrations were 2.5 µM and 300 nM, respectively. The results are summarized in FIG. 4. Incubation of inhibitor D with Norwalk virus 3CL protease lead to dose-dependent inhibition of the enzyme (FIG. 5). It is evident from FIG. 4 that the presence of the aldehyde warhead was important for inhibitory activity in the synthesized compounds since the precursor alcohols were either inactive or had minimal activity (compare, for example, inhibitor C with D, inhibitor E with F, and inhibitor G with H). Furthermore, the nature of the cap was also important (compare, for example, inhibitors A and D). In order to gain a better insight and understanding into the binding of Inhibitor D to the active site of the enzyme, computer modeling was used to demonstrate that inhibitor D is capable of adopting a low energy conformation that closely resembles the conformer of the co-crystallized peptide (FIG. 6).

A prospective bound conformer for NV 3CL protease inhibitor D was determined via a genetic algorithm conformational optimization using the SYBYL program (SYBYL 8.0, The Tripos Associates, St. Louis, Mo., 2008). The covalently-bound ligand-receptor complex was prepared from the PDB 1IPH crystal structure by deleting the co-crystallized ligand and adding the ligand (one atom at a time) in an analogous conformation via the "Add Atom" utility so as to have conformational control during construction of the ligand and ensure automatically specification of low energy bond lengths and bond angles. Hydrogens were added to the entire complex according to the automatic SYBYL algorithm (assuming cationic Lys and Arg residues, and anionic Asp and Glu) and were positionally optimized via molecular mechanics with all heavy atoms held rigid and default convergence criteria using the Tripos Molecular Force Field and Gasteiger-Marsili charges. The resulting complex was then subjected to a genetics algorithm conformational search implemented in SYBYL, requesting identification of the top twenty most favorable conformations. The search yielded only one plausible low-energy conformation (FIG. 6).

Thus, in addition to covalent bond formation between the active site cysteine residue (Cys139) and the inhibitor aldehyde carbonyl (see general illustration in FIG. 2), inhibitor D engages in multiple favorable binding interactions with the enzyme, including lipophilic interactions involving the —CH$_2$—CH$_2$— segment of the ligand lactam with the —CH$_2$—CH$_2$— segment of Pro136, leucine side chain in inhibitor with His30, Ile109 and Val 114, and interactions of the phenyl ring in the Cbz cap—partially occupying the S4 pocket—with Ile 109. In addition, a network of hydrogen bonds involving Thr134 (backbone carbonyl), Ala158 (backbone carbonyl), Gln110 (side chain carbonyl), and Ala160 (backbone amide proton) is clearly evident. Extending the inhibitor by an additional amino acid (as in inhibitor E) improved potency, albeit not dramatically (compare inhibitors D and E). Modeling studies suggested that replacement of Leu by other hydrophobic amino acids might result in an optimal fit of the amino acid side chain in the S2 pocket, improving potency. Indeed, inhibitor G with a P2 Nle was found to be a sub-micromolar inhibitor of the enzyme, however, replacement of Leu with Ile (inhibitor I) was detrimental to inhibitory activity. α-Ketoamide inhibitor J was devoid of inhibitory activity, suggesting that steric congestion in the vicinity of the S1' subsite is severe.

The activity of inhibitors D-E against norovirus was investigated using a cell-based replicon system of NV replicon-harboring cells (human glioblastoma HG23 cells). The detailed procedures for studying the antiviral effects using HG23 cells were reported elsewhere. Briefly, One-day old, 80-90% confluent HG23 cells were treated with varying concentrations of inhibitor D or E (0 [mock-DMSO]-320 µM) to examine its effects on the replication of NV. At 24 or 48 hrs of treatment, the NV protein and genome were analyzed with Western blot and qRT-PCR, respectively. The ED50 of inhibitor D or E for NV genome levels was determined at 24 hrs post-treatment. The cytotoxic effects of inhibitor D or E on HG23 cells using a cell cytotoxicity assay kit (Promega, Madison, Wis.) to calculate the median toxic dose (TD50) at 48 hrs of treatment. The effects of inhibitors D and E were also examined in murine norovirus-1 (MNV-1). MNV-1 can be cultured in the murine macrophage-like cell line RAW267.4, thus MNV-1 can be a surrogate system to examine the effects of antiviral compounds on norovirus replication in cells. Confluent RAW267.4 cells in 6-well plates were inoculated with MNV-1 at a multiplicity of infection (MOI) of 2 with varying concentrations (0-320 µM) of inhibitors D and E. Virus infected cells were then incubated for an additional 12 and 24 hrs. After freezing and thawing plates 3 times, the replication of MNV-1 in the presence of the compound was measured by the 50% tissue culture infective dose (TCID50) assay. The nonspecific cytotoxic effects in RAW267.4 cells by ribavirin were monitored by the method described above.

Inhibitors D and E were found to be active with the effective dose that inhibit 50% of norovirus replication, ED50 at 2.1 and 7.8 µM, respectively. The median toxic dose, TD50 for both inhibitors D and E was found to be >320 µM. The inhibitors D and E also inhibit the replication of murine norovirus (MNV) in RAW267.4 cells with ED50's 5.5 and 20.3 µM, respectively. The TD50 for both inhibitors D and E in RAW267.4 was found to be >320 µM.

In conclusion, this first series of transition state inhibitors of norovirus protease exhibited noteworthy activity in a cell-based replicon system of norovirus infection.

Example 2

Figure 7:
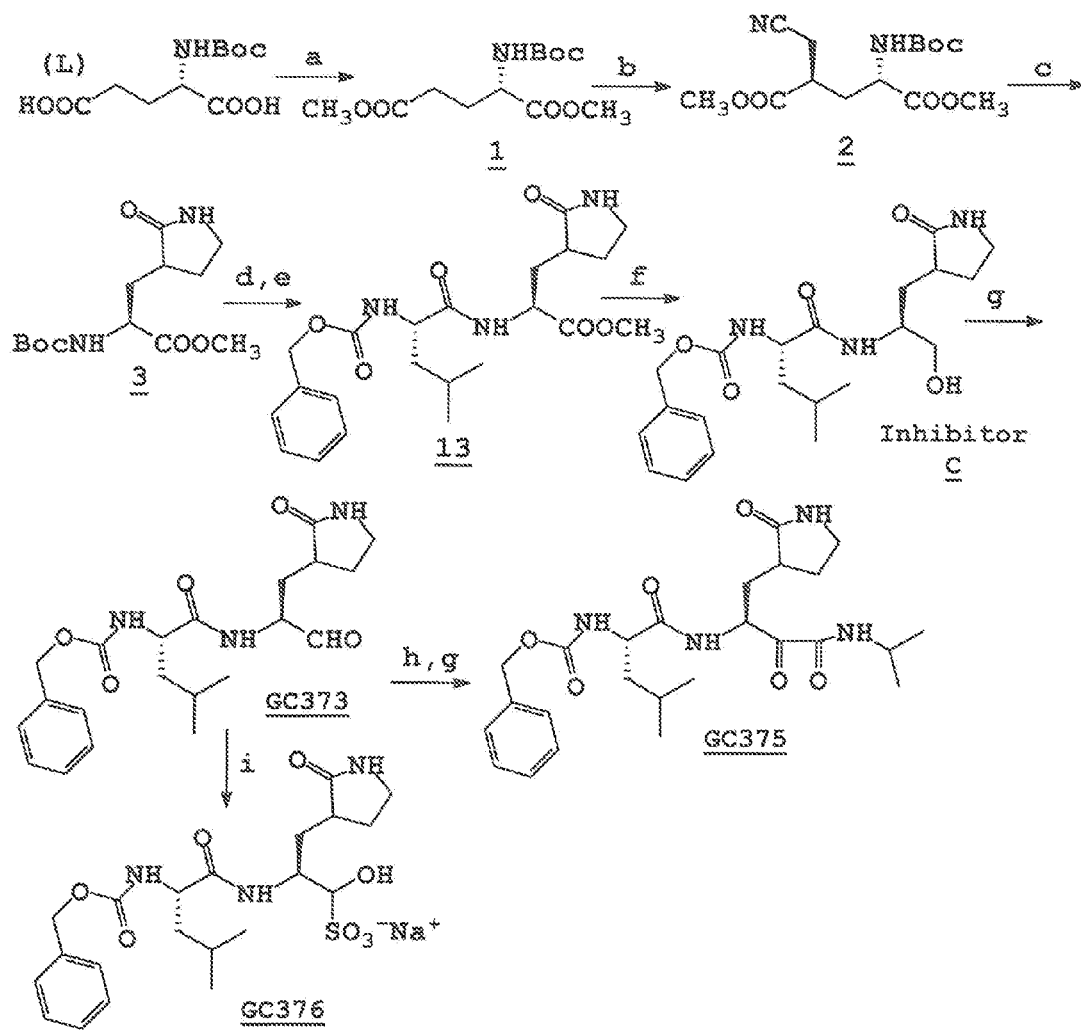
FIG. 7 is a schematic showing preparation of peptidyl aldehydes and their bisulfite salts, and peptidyl alpha-ketoamide antiviral compounds in Example 2.

Proteases Exhibiting Broad-Spectrum Activity Against Viruses that Belong to the Picornavirus-Like Supercluster Materials and Methods:

1. Cells, viruses, and reagents. The various cell lines including HG23 cells (Huh-7, human hepatoma cells, containing NV replicon), CRFK (feline kidney cell line), RAW267.4 (murine monocytes/macrophages), ST (porcine testis cells), CCL-9.1 (murine hepatocytes), HRT18 (human colon cancer cells), MRC-5 (human lung fibroblast cells), FRhK-4 (monkey kidney cells), and Vero cells (monkey kidney cells) were maintained in Dulbecco's minimal essential medium (DMEM) or MEM containing 10% fetal bovine serum and antibiotics (chlortetracycline [25 µg/ml], penicillin [250 U/ml], and streptomycin [250 µg/ml]) (DMEM-C). Murine norovirus-1 was provided by Dr. H. Virgin (Washington University in St Louis, Mo.), and maintained in RAW267.4 cells. Viruses used in the study were feline calicivirus (FCV), murine norovirus (MNV-1), transmissible gastroenteritis virus (TGEV), bovine coronavirus (BCV), feline infectious peritonitis virus (FIPV), human coronavirus 229E strain, mouse hepatitis virus (MHV), hepatitis A virus (HAV), porcine teschovirus, and enterovirus 71 (EV71). Various peptidyl aldehydes and their bisulfite salts, and alpha-ketoamide including GC373, GC375, and GC376 (FIG. 7) were synthesized as described below.

2. Protease assay. A fluorescence resonance energy transfer (FRET) protease assay has been developed to provide a rapid and specific identification of protease inhibitors for various cellular and viral proteases including foot-and-mouth virus and severe acute respiratory syndrome (SARS) coronavirus. In this assay system, substrates have a fluorescence donor and a quencher on each end, and the donor fluorescence signal in the uncleaved substrate is inhibited by the interaction of the fluorescence donor and quencher. Once substrates are cleaved by a protease, the donor fluorescence is no longer quenched, yielding an increase in fluorescence intensity. Addition of protease inhibitors to the assay inhibits the cleavage of the substrates, which leads to reduced fluorescence intensity, enabling screening of potential protease inhibitors.

For our studies, the full-length cDNAs corresponding to the complete amino acid sequence of each viral protease from various viruses as well as sequences encoding N-terminal six H for Ni column purification were expressed and purified. Fluorogenic substrates with Edans and Dabcyl as donor/quencher pair were purchased from Bachem (corona virus substrate) or synthesized (GenScript, Piscataway, N.J.). The viral proteases and the corresponding fluorogenic substrates are listed in Table 1. The designation of substrate residues for P1 and P1' starts at the scissile bond and counts toward the N- or C-terminus, respectively, in accordance with the nomenclature of Schechter and Berger (Schechter and Berger, 1967).

slope using GraphPad Prism software in order to determine the concentrations of inhibitors that results in half-maximum change in RFU (IC50).

TABLE 2

Viruses used for cell-based screening assay.

| Virus family | Viruses | Cell lines |
|---|---|---|
| Calicivirus | Norwalk virus | HG23 |
| | FCV | CRFK |
| | MNV-1 | RAW267.4 |
| Coronaviridae | TGEV | ST |
| | FIPV | CRFK |
| | 229E | MRC-5 |
| | MHV | CCL-9.1 |
| | BCV | HRT18 |
| Picornaviridae | Teschovirus | ST |
| | Enterovirus 71 | Vero |

3. Cell-based screening of inhibitor. The effects of each inhibitor on the viral replication were examined. The list of viruses and corresponding cell lines are listed above in Table 2. Briefly, confluent cells were inoculated with virus at a MOI of 5 or 0.05 for 1 hr, and medium was replaced with medium containing mock-medium or each compound (up to 100 μM). The virus infected cells were further incubated for up to 96 hrs, and the replication of virus was measured by TCID50 assay with the 10-fold dilution of each sample used

TABLE 1

Virus proteases and fluorogenic substrates used for FRET assay.

| Virus family | Viruses | Fluorogenic substrates (Edans/Dabcyl) |
|---|---|---|
| Calicivirus | Norwalk virus (NV) | DFHLQ/GP (residues 3-9 of SEQ ID NO: 1) |
| | MD145 | DFHLQ/GP (residues 3-9 of SEQ ID NO: 1) |
| Coronaviridae | TGEV | KTSAVLQ/SGFRKME (SEQ ID NO: 2) |
| | SARS-Co | KTSAVLQ/SGFRKME (SEQ ID NO: 2) |
| | Human coronavirus 229E | KTSAVLQ/SGFRKME (SEQ ID NO: 2) |
| Picornaviridae | Polio | KTSAVLQ/SGFRKME (SEQ ID NO: 2) |
| | HRV | DFHLQ/GP (residues 3-9 of SEQ ID NO: 1) |
| | HAV | GLRTQ/SFS (SEQ ID NO: 3) |
| | FMDV | APAKQLLN (SEQ ID NO: 4) |
| | Enterovirus 71 | KTSAVLQ/SGFRKME (SEQ ID NO: 2) |

The FRET-based protease assay was performed as follows; stock solutions (10 mM) of the substrates and compounds were prepared in DMSO, and diluted in assay buffer (50 mM HEPES buffer [pH 8.0] containing 120 mM NaCl, 0.4 mM EDTA, 20% Glycerol, and 4 mM DTT). Each protease was mixed with serial dilutions of each inhibitor or mock (DMSO) in 25 μL of assay buffer and incubated at 37° C. for 30 min, followed by the addition of 25 μL of substrates. The mixtures were incubated at 37° C. for an additional hour, and fluorescence readings were obtained on a microplate reader using an excitation wavelength of 360 nm and an emission wavelength of 460 nm on a fluorescence microplate reader (FLx800, Biotek, Winooski, Vt.). The relative fluorescence units (RFU) were determined by subtracting background values (substrate containing well without protease) from the raw fluorescence values. The dose-dependent FRET inhibition curves were fitted with variable for virus titration (Reed and Muench, 1938). In some viruses, the virus protein and genome expression levels were detected by Western blot analysis and real-time qRT-PCR, respectively, as described below. The IC50s of the compounds were calculated.

Real-Time qRT-PCR. The quantity of virus genome in the NV replicon-harboring cells was measured by real-time qRT-PCR with One-step Platinum qRT-PCR kit (Invitrogen, Carlsbad, Calif.), following an established protocol with specific primers and probes as described previously (Chang and George, 2007a). For qRT-PCR, the total RNA in cells (in 6-well plate) was extracted with RNeasy kit (Qiagen, Valencia, Calif.). The primer sequences for NV were: Forward 5'-CGYTGGATGCGITTYCATGA-3' (SEQ ID NO:5) and reverse 5'-CTTAGACGCCATCATCATTYAC-3' (SEQ ID NO:6). The probe sequence used was: FAM-5'-AG-ATYGCGITCICCTGTCCA-3'-Iowa Black (SEQ ID NO:7).

The qRT-PCR amplification was performed in a SmartCycler (Cepheid, Sunnyvale, Calif.) with the following parameters: 45° C. for 30 min, and 95° C. 10 min, followed by 40 cycles of denaturation at 95° C. for 30 s, annealing at 50° C. for 1 min and elongation at 72° C. for 30 s. For quantity control, qRT-PCR for β-actin was performed as described previously (Spann et al., 2004). The relative genome levels in cells with various treatments were calculated after the RNA levels were normalized with those of β-actin.

Western blot analysis. Protein samples of HG23 cells or MNV-1 infected RAW 267.4 cells with various treatments were prepared in SDS-PAGE sample buffer containing 1% β-mercaptoethanol, and sonicated for 20 sec. The proteins were resolved in a 10% Novex Tris-Bis gel (Invitrogen) and transferred to a nitrocellulose membrane. The membranes were probed with guinea pig antibodies specific for NV ProPol protein and the binding of the antibodies was detected with peroxidase-conjugated, goat anti-guinea pig IgG (Sigma-Aldrich). In addition, membranes were probed with rabbit antiserum specific for β-actin and peroxidase-conjugated, goat anti-rabbit IgG as a loading control. Following incubation with a chemiluminescent substrate (SuperSignal West Pico Chemiluminescent Substrate, Pierce Biotechnology, Rockford, Ill.), signals were detected with X-ray film.

4. Cell cytotoxicity. The nonspecific cytotoxic effects of each inhibitor on cells were monitored by observation under a microscopy and CytoTox 96 Non-radioactive cytotoxicity assay (Promega, Madison, Wis.).

5. Peptidyl aldehydes and their bisulfite salts, and alpha-ketoamide, including several of the inhibitors from Example 1, were synthesized as illustrated generally in FIG. 7, and described below.

Chemistry/Experimental Procedures:

Intermediate 1.

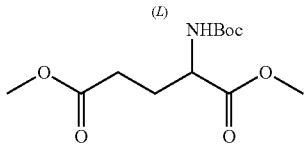

1

To a stirred solution of N-boc-L-glutamic acid (61.75 g, 250 mmol) in dry DMF (500 mL) were added NaHCO$_3$ (95%, 126.01 g, 1500 mmol) and CH$_3$I (141.0 g, 1000 mmol) sequentially and the mixture was stirred at RT for 5 days. Most of the DMF was removed in vacuo and the residue was taken up in ethyl acetate (600 mL). The organic layer was washed with brine (2×100 mL), dried over anhydrous sodium sulfate, filtered, and concentrated, leaving a thick yellow oil (~65 g) which was purified by flash chromatography (silica gel/hexane/ethyl acetate=7/1) to give the dimethyl ester as colorless oil (54.56 g, 79.4% yield). 1H NMR (CDCl$_3$): δ 1.41 (s, 9H), 1.90-2.01 (m, 1H), 2.19-2.23 (m, 1H), 2.55-2.69 (m, 2H), 3.68 (s, 3H), 3.75 (s, 3H), 4.35 (d, 1H), 5.18 (d, 1H).

Intermediate 2.

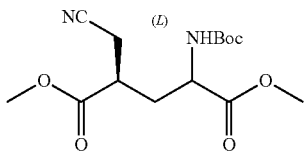

2

A stirred solution of lithium bis(trimethylsilyl)amide (hexamethyldisalazide, LiHMDS in THF (259.2 ml, 1M, 259.2 mmol) was added dropwise to a solution of intermediate 1 (33 g, 120 mmol) in anhydrous THF (360 mL) kept at −78° C. (using dry ice with acetone) under a nitrogen atmosphere. The resulting mixture was stirred at −78° C. for 1 h. Bromoacetonitrile (TCI) (15.54 g, 128.4 mmol) was added dropwise to the reaction mixture over a period of 1 h while maintaining the temperature below −70° C. The reaction mixture was stirred at −78° C. for an additional 5 h and then quenched by adding cold methanol (24 mL) in one portion and stirred for 30 min. The resulting methoxide was then quenched by adding cold acetic acid (24 mL) in THF (144 mL) in one portion. After stirring for 30 min the cooling bath was removed and replaced with a water bath. The reaction mixture was allowed to warm up to room temperature and then poured into a saturated brine solution (600 mL). The organic layer was separated and the aqueous layer was extracted with ethyl acetate (2×400 mL). The combined organic layers were dried over anhydrous sodium sulfate and concentrated to give a reddish oil (43.48 g). The reddish oil was dissolved in methylene chloride (500 mL) and treated with silica gel (50 g) and activated carbon (2-3 scoops). The slurry was filtered using a Hirsh funnel and washed with methylene chloride (50 mL). The filtrate was concentrated to afford a yellow oil (27.15 g, 71.98% yield) which was purified by flash chromatography (silica gel/hexane/ethyl acetate=3:1), leaving a light yellow oil (19.5 g, 51.7% overall yield). 1H NMR (CDCl$_3$): δ 1.42 (s, 9H), 2.16-2.20 (m, 2H), 2.78-2.80 (m, 2H), 2.82-2.91 (m, 1H), 3.78 (s, 6H), 4.40 (m, 1H), 5.08 (d, 1H).

Intermediate 3.

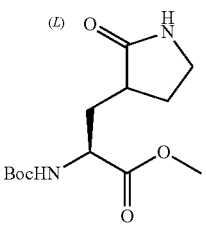

3

A pink solution of CoCl$_2$.6H$_2$O (Acros) (5.95 g, 25 mmol) and intermediate 2 (15.7 g, 50 mmol) in methanol (300 mL) was stirred vigorously and cooled to 0° C. while NaBH$_4$ (7.56 g, 200 mmol) was added portionwise over 30 min. The reaction was stirred at RT for 24 h (reaction was monitored by TLC to ensure completion). Most of the methanol was removed, leaving a viscous black oil which was taken up in ethyl acetate (400 mL), and washed with brine (200 mL). The mixture was allowed to stand in a separatory funnel for 2 h, at which time the two layers separated (incompletely). Addition of 5% HCl (150 mL) resulted in complete separation of the two layers. The organic layer was separated and the aqueous layer was extracted with ethyl acetate (2×200 mL). The organic extracts were combined, dried over sodium sulfate, filtered, and concentrated, leaving a crude green oil (13.09 g), which was purified by flash chromatography (silica gel/hexane/ethyl acetate=1:1) to give a white solid (8.26 g, 58% yield), mp 85-87° C. 1H NMR (CDCl$_3$): δ 1.43 (s, 9H), 1.77-1.90 (m, 2H), 2.05-2.18 (m, 1H), 2.40-2.50 (m, 2H), 3.31-3.39 (m, 2H), 3.74 (s, 3H), 4.25-4.31 (m, 1H), 5.51 (d, J=9.09 Hz, 1H).

Intermediate 4.

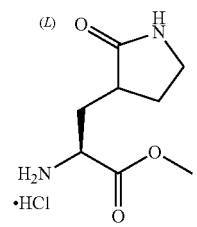

4

A solution of 4M HCl in dioxane (30 mL) was added to a solution of intermediate 3 (1.72 g, 6 mmol) at RT with stirring. The mixture was stirred for 2 h and then concentrated to yield a crude salt which was used in the next step without purification. 1H NMR (CDCl₃): δ 1.60-1.80 (m, 1H), 1.80-2.00 (m, 1H), 2.00-2.10 (m, 1H), 2.51-2.63 (m, 1H), 3.20 (m, 2H), 3.79 (s, 2H), 4.10-4.22 (s, 1H), 8.00 (s, 1H), 8.40-8.70 (s, 2H).

Intermediate 5.

5

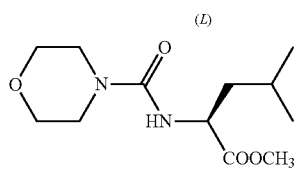

A solution of (L) Leu-OMe hydrochloride (9.05 g, 50 mmol) in DMF (250 mL) was treated with N,N-diisopropylethyl amine (19.35 g, 150 mmol) and the solution was stirred for 15 min. 4-Morpholinecarbonyl chloride (11.18 g, 75 mmol) was added and the solution was stirred at RT overnight. The solvent was removed in vacuo and the reddish oil was dissolved in ethyl acetate (500 mL) and washed sequentially with 5% HCl (200 mL), saturated sodium bicarbonate (2×200 mL) and brine (200 mL). The organic layer was separated, dried, and concentrated, leaving a yellow solid which was washed with hexane (150 mL). The solid was collected by suction filtration, leaving a white powder (9.84 g, 67% yield), mp 108-110° C. 1H NMR (CDCl₃): δ 0.99 (m, 6H), 1.49-1.60 (m, 2H), 1.62-1.80 (m, 1H), 3.38 (q, J=9.09 Hz, 4H), 3.71 (q, J=9.09 Hz, 4H), 3.75 (s, 3H), 4.49-4.60 (m, 1H), 4.80 (d, 1H).

Intermediate 6.

6

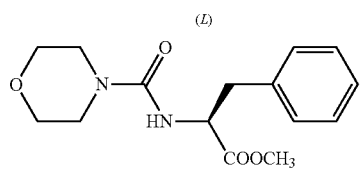

Intermediate 6 was synthesized starting with (L) Phe-OCH₃ hydrochloride using a similar procedure as that used in the synthesis of intermediate 5. White solid (9.7 g, 82.9% yield), mp 83-85° C. 1H NMR (CDCl₃): δ 3.12 (m, 2H), 3.20-3.40 (m, 4H), 3.60-3.80 (m, 4H), 3.75 (s, 3H), 4.75-4.90 (m, 1H), 7.09 (d, 1H), 7.15-7.35 (m, 5H).

Intermediate 7.

7

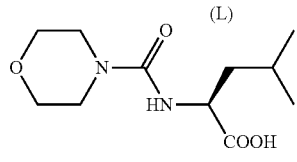

A solution of ester 5 (4.41 g, 15 mmol) in THF (30 mL) was treated with a solution of lithium hydroxide (0.718 g, 30 mmol) in water (30 mL) and the reaction was stirred for 1 h at RT (monitored by TLC until starting ester disappeared). The solvent was evaporated and water (25 mL) was added to the residue. The solution was extracted with ethyl acetate (50 mL) to remove impurities. The aqueous solution was acidified to pH 2-3 using 5% hydrochloride acid (30 mL) and extracted with ethyl acetate (3×100 mL). The combined organic layers were dried over sodium sulfate, filtered, and concentrated, leaving a yellow oil (4.40 g, 100% yield). 1H NMR (CDCl₃): δ 1.00 (m, 6H), 1.58-1.65 (m, 1H), 1.66-1.80 (m, 2H), 3.35-3.50 (q, J=37.0 Hz, 4H), 3.60-3.80 (t, J=37.0 Hz, 4H), 4.40-4.46 (m, 1H), 4.49 (d, 1H).

Intermediate 8.

8

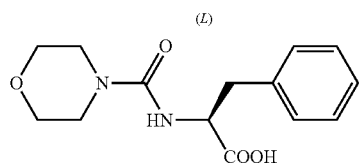

Intermediate 8 was synthesized from intermediate 6 using a similar procedure as that used in the synthesis of intermediate 7. Yellow oil (4.15 g, 99.5% yield). 1H NMR (CDCl₃): δ 3.10-3.20 (m, 2H), 3.20-3.40 (m, 4H), 3.50-3.70 (t, J=12.9 Hz, 4H), 4.60-4.71 (q, J=12.9 Hz, 1H), 4.85 (d, 1H), 7.19 (d, 2H), 7.20-7.35 (m, 3H).

Intermediate 9.

9

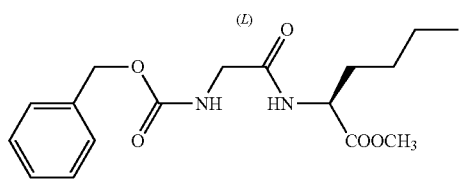

A solution of Z-Gly-OH (4.18 g, 20 mmol) in dry THF (40 mL) was added dropwise to a solution of carbonyldiimidazole (3.77 g, 23.4 mmol) in dry THF (20 mL) and the reaction mixture was stirred at RT for 20 min. At the same time (L) Nle methyl ester hydrochloride salt (3.63 g, 20 mmol) in THF (20 mL) was treated with triethylamine (4.04 g, 40 mmol) and stirred for 20 min. The two reaction mixtures were mixed and stirred at RT overnight. The solvent was removed and the residue was taken up in ethyl acetate (200 mL). The solution was washed with saturated sodium bicarbonate (25 mL) and brine (40 mL). The organic layer was dried over sodium sulfate, filtered and concentrated, leaving a colorless oil (6.2 g, 92.3% yield). 1H NMR (CDCl₃): δ 0.90-1.00 (t, J=16.13 Hz, 3H), 1.60-1.75 (m, 2H), 1.75-1.90 (m, 2H), 3.70-3.80 (s, 3H), 3.80-4.00 (m, 2H), 4.58-4.65 (q, J=9.68 Hz, 1H), 5.18 (s, 2H), 5.40-5.50 (s, 1H), 6.45-6.60 (d, 1H), 7.20-7.45 (m, 5H).

Intermediate 10.

10

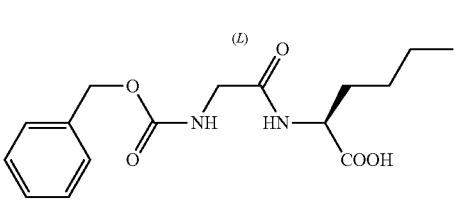

To a solution of intermediate 9 (6.0 g, 18.8 mmol) in THF (60 mL) was added lithium hydroxide (1M, 40 mL) and the reaction mixture was stirred at RT for 2 h. The solvent was removed in vacuo and the residue was taken up in water (100 mL) and extracted with ethyl acetate (2×200 mL). The aqueous layer was acidified to pH-1 using 5% hydrochloride acid. The aqueous layer was extracted with ethyl acetate (2×200 mL) and the combined organic layers were dried over sodium sulfate, filtered and concentrated, leaving a white solid (5.20 g, 85.8% yield), mp 85-87° C. 1H NMR (CDCl$_3$): δ 0.80-0.85 (t, J=6.90 Hz, 3H), 1.50-1.60 (m, 2H), 1.60-1.70 (m, 2H), 3.60 (t, J=6.90 Hz, 2H), 4.17 (q, J=5.17 Hz, 1H), 5.00 (s, 2H), 7.30-7.40 (m, 5H), 7.42 (t, J=5.17 Hz, 1H), 8.03 (d, 1H).

Intermediate 11.

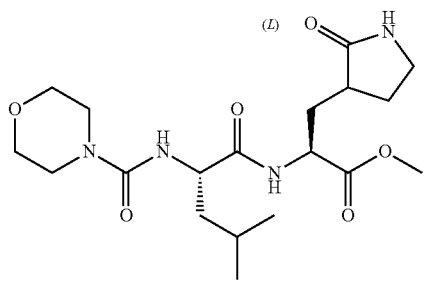

A solution of intermediate 4 (1.63 g, 6 mmol) and intermediate 5 (1.61 g, 6.6 mmol) in dry dimethyl sulfoxide (50 mL) cooled to 0° C. was treated with N,N-diisopropylethyl amine (2.32 g, 18 mmol), 1-Hydroxybenzotriazole monohydrate (1.15 g. 7.5 mmol) and 1-ethyl-3-(3-dimethylaminopropyl) carbodiimide (1.43, 7.5 mmol) sequentially. The ice bath was removed and the reaction mixture was stirred at RT overnight. The reaction mixture was diluted with dichloromethane (150 mL) and washed with 10% aqueous citric acid (60 mL) and brine (60 mL). The organic layer was separated, dried, and concentrated, leaving a yellow oil which was purified by flash chromatography (silica gel/hexane/ethyl acetate) to give a white solid (1.12 g, 42% yield), mp 158-160° C. 1H NMR (CDCl$_3$): δ 0.99 (d, 6H), 1.49-1.95 (m, 7H), 2.20-2.32 (m, 1H), 2.33-2.58 (m, 2H), 3.30-3.50 (m, 6H), 3.60-3.80 (m, 4H), 3.72 (s, 3H), 4.40-4.52 (m, 1H), 4.52-4.63 (m, 1H), 5.32 (d, 1H), 6.89 (s, 1H), 8.05 (d, 1H).

Intermediate 12.

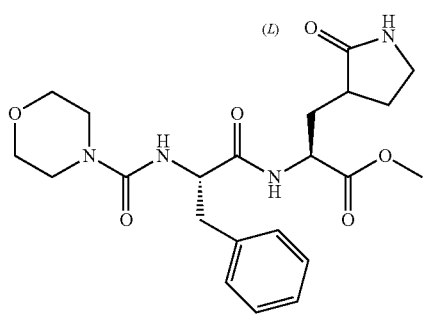

Prepared using a similar procedure as described above and intermediates 4 and 8. White solid (0.82 g, 61.2% yield), mp 133-135° C. 1H NMR (CDCl$_3$): δ 1.80-2.00 (m, 2H), 2.00-2.15 (m, 2H), 2.20-2.30 (m, 1H), 2.30-2.45 (m, 1H), 3.09-3.30 (m, 2H), 3.25-3.40 (m, 6H), 3.60-3.73 (m, 4H), 3.75 (s, 3H), 4.40-4.50 (m, 1h0, 4.72-4.81 (m, 1H), 5.09 (d, 1H), 5.50 (s, 1H), 7.19-7.30 (m, 5H), 7.70 (d, 1H).

Intermediate 13.

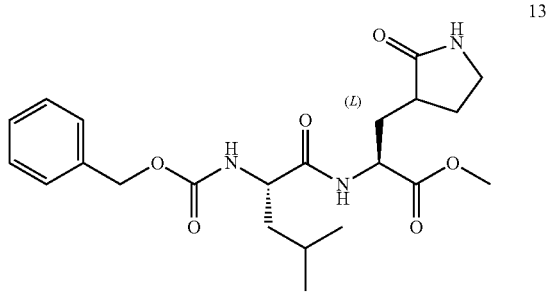

White solid (3.82 g, 72.2% yield), mp 53-55° C. 1H NMR (CDCl$_3$): δ 0.99 (d, 6H), 1.40-1.95 (m, 6H), 2.10-2.25 (m, 2H), 2.25-2.45 (m, 2H), 3.20-3.35 (m, 2H), 3.60-3.75 (s, 3H), 4.30-4.38 (m, 1H), 4.40-4.45 (m, 1H), 5.00-5.20 (s, 2H), 5.50 (d, 1H), 6.40 (s, 2H), 7.20-7.40 (m, 5H), 7.92 (d, 1H).

Intermediate 14.

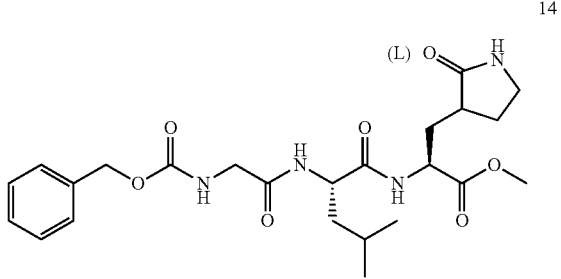

White solid (4.42 g, 85.99% yield), mp 88-90° C. 1H NMR (CDCl$_3$): δ 0.90 (d, 6H), 1.40-1.95 (m, 6H), 2.00-2.18 (m, 2H), 2.30-2.42 (m, 2H), 3.20-3.35 (d, 2H), 3.69 (s, 3H), 3.80-4.03 (m, 2H), 4.35-4.41 (m, 1H), 4.58-4.63 (m, 1H), 5.00-5.16 (s, 2H), 5.98 (s, 1H), 6.72 (s, 1H), 7.05 (d, 1H), 7.30-7.40 (m, 5H), 8.38 (d, 1H).

Intermediate 15.

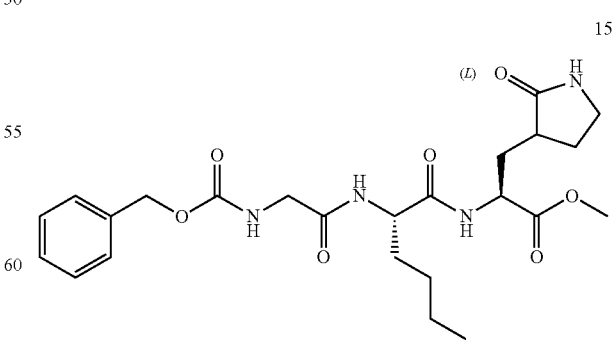

White solid (1.60 g, 70% yield), mp 45-47° C. 1H NMR (CDCl$_3$): δ 0.80-0.90 (s, 3H), 1.10-1.40 (s, 4H), 1.50-1.70 (m, 1H), 1.70-1.95 (m, 2H), 1.95-2.20 (m, 1H), 3.20-3.35 (s, 2H), 3.63 (s, 3H), 3.70-3.90 (m, 1H), 3.90-4.10 (m, 1H), 4.23-4.70 (m, 2H), 5.00-5.15 (s, 2H), 6.03 (s, 1H), 6.80 (s, 1H), 7.20-7.40 (m, 5H), 8.22 (s, 1H).

Intermediate 16.

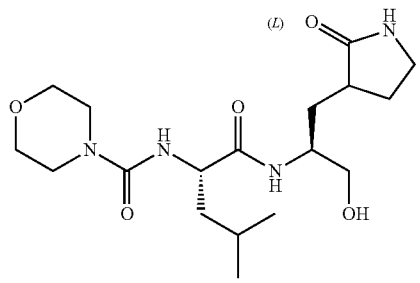

Intermediate 11 (1.06 g, 2.36 mmol) was dissolved in DCM (50 mL) and cooled to 0° C. Lithium borohydride (1M in THF, 3.54 mL, 3.45 mmol) was added with stirring. The reaction mixture was stirred for 3 h at 0° C., then quenched by the addition of ammonium chloride (25 mL). The THF was removed and ethyl acetate (200 mL) and brine (50 mL) were added to the residue. The organic layer was separated and the aqueous layer was extracted with ethyl acetate (2×100 mL). The organic layers were combined, dried over sodium sulfate, and concentrated, leaving a colorless oil (0.42 g, 46.7% yield). 1H NMR (CDCl$_3$): δ 0.99 (d, 6H), 1.40-2.00 (m, 7H), 2.33-2.50 (m, 2H), 3.30-3.42 (m, 6H), 3.53-3.60 (m, 2H), 3.60-3.72 (m, 4H), 3.95-4.00 (m, 1H), 4.35-4.40 (m, 1H), 5.10 (d, 1H), 3.05 (s, 1H), 7.85 (s, 1H).

Intermediate 17.

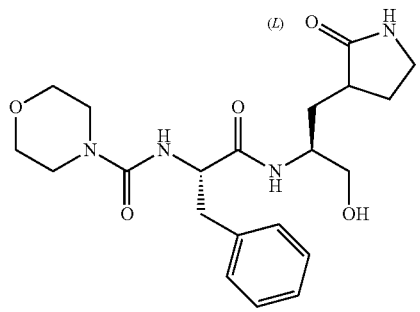

White solid (0.46 g, 74% yield), mp 103-105° C. 1H NMR (CDCl$_3$): δ 1.50-1.80 (m, 2H), 1.70-1.95 (m, 5H), 2.10-2.23 (m, 1H), 2.23-2.40 (m, 1H), 2.90-3.03 (m, 1H), 3.18-3.31 (m, 1H), 3.28-3.45 (m, 6H), 3.52-3.60 (m, 1H), 3.60-3.69 (m, 4H), 3.80-3.93 (m, 1H), 4.60-4.70 (m, 1H), 5.17 (d, 1H), 5.50 (s, 1H), 7.16-7.35 (m, 5H), 7.58 (d, 1H).

Inhibitor C

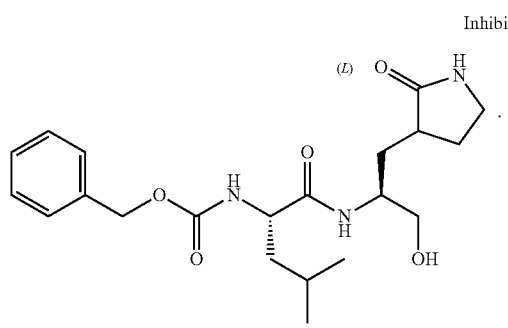

White solid (0.99 g, 96% yield), mp 63-65° C. 1H NMR (CDCl$_3$): δ 0.99 (d, 6H), 1.40-2.10 (m, 8H), 2.25-2.45 (m, 2H), 3.20-3.35 (m, 2H), 3.40-3.69 (m, 2H), 3.90-4.01 (s, 1H), 4.20-4.27 (m, 1H), 5.00-5.20 (s, 2H), 5.40 (d, 1H), 5.98 (s, 2H), 7.20-7.40 (m, 5H), 7.80 (d, 1H).

Inhibitor F

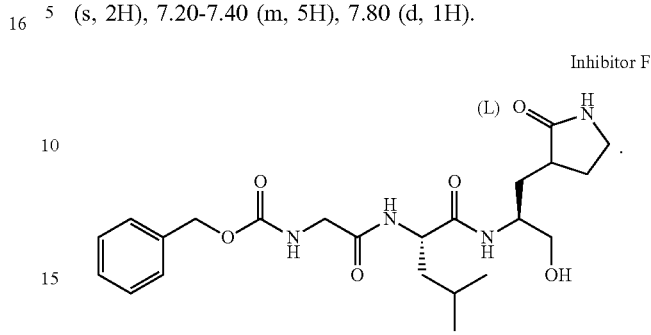

White solid (1.11 g, 79% yield), mp 68-70° C. 1H NMR (CDCl$_3$): δ 0.90 (d, 6H), 1.40-2.00 (m, 8H), 2.30-2.40 (m, 2H), 3.20-3.30 (m, 2H), 3.50-3.71 (m, 2H), 3.71-4.00 (m, 2H), 4.00-4.12 (m, 1H), 4.50-4.60 (m, 1H), 5.10 (s, 2H), 5.82 (s, 1H), 6.04 (s, 1H), 6.65 (d, 1H), 7.20-7.40 (m, 5H), 8.03 (d, 1H).

Inhibitor H

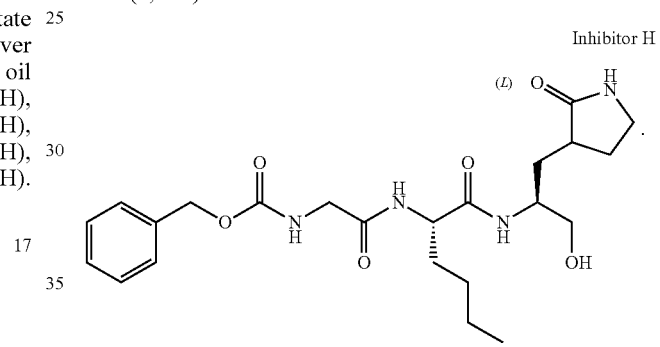

White solid, mp 73-75° C. 1H NMR (CDCl$_3$): δ 0.80-0.95 (s, 3H), 1.20-1.40 (m, 4H), 1.50-1.65 (m, 2H), 1.66-2.00 (m, 2H), 2.30-2.40 (s, 2H), 3.20-3.40 (m, 2H), 3.80-4.20 (m, 3H), 4.40-4.52 (q, J=5.17 Hz, 1H), 5.00-5.20 (s, 2H), 6.00-6.20 (s, 1H), 6.90-7.00 (d, 1H), 8.00 (d, 1H).

Inhibitor A

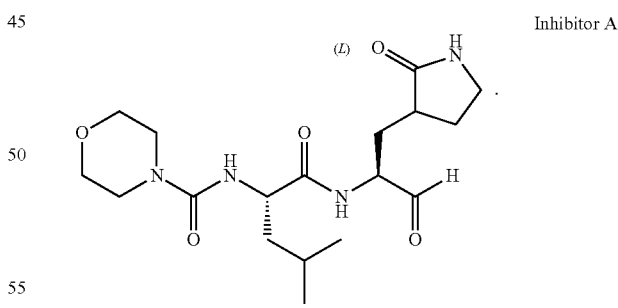

Intermediate 16 (0.35 g, 0.9 mmol) was suspended in anhydrous DCM (10 mL) under a nitrogen atmosphere and Dess-Martin reagent (15% wt in dichloromethane, 5.088 g, 2.00 mmol) was added with stirring. The reaction was stirred at RT for 1 h and the reaction was monitored by TLC until the starting material disappeared. The solvent was removed, leaving a yellow oil which was purified by flash chromatography to give a yellow oil mixed with solid. The mixture was treated with chloroform (10 mL) and the solid was filtered off by suction filtration. The filtrate was dried over anhydrous sodium sulfate and the solvent was evaporated, leaving a yellow solid (0.2 g, 58% yield), mp 78-80° C. 1H NMR (CDCl₃): δ 0.99 (d, 6H), 1.40-2.00 (m, 7H), 2.16-2.25 (m, 1H), 2.50-2.60 (m, 1H), 3.30-3.43 (m, 6H), 3.60-3.80 (m, 4H), 4.30-4.40 (m, 1H), 4.40-4.51 (m, 1H), 5.23 (d, 1H), 6.55 (s, 1H), 9.43 (s, 1H).

Inhibitor B

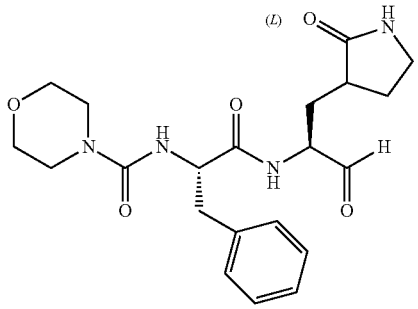

Yellow solid (0.31 g, 59.6% yield), mp 65-67° C. 1H NMR (CDCl₃): δ 1.70-1.90 (m, 2H), 2.10-2.20 (m, 1H), 2.20-2.40 (m, 2H), 3.00-3.20 (m, 2H), 3.20-3.40 (m, 4H), 3.56-3.70 (m, 4H), 3.70 (s, 2H), 4.40-4.50 (m, 1H), 4.70-4.80 (m, 1H), 6.35 (d, 1H), 7.10-7.30 (m, 5H), 7.90 (d, 1H), 8.23 (m, 1H), 9.22 (s, 1H).

Inhibitor D (aka GC373)

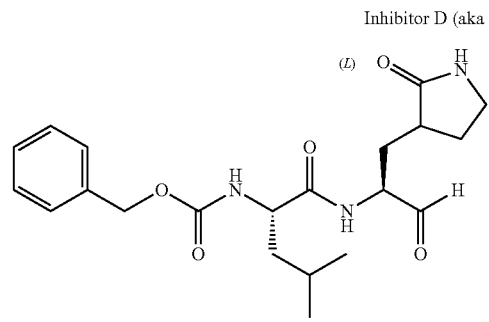

Yellow solid (0.63 g, 67.0% yield), mp 76-78° C. 1H NMR (CDCl₃): δ 0.95 (d, 6H), 1.40-2.00 (m, 6H), 2.00-2.20 (d, 2H), 2.20-2.50 (m, 2H), 3.20-3.40 (m, 2H), 4.20-4.39 (m, 1H), 4.40-4.50 (m, 1H), 5.10 (s, 2H), 5.30-5.40 (m, 1H), 5.90 (s, 1H), 7.20-7.40 (m, 5H), 8.31 (m, 1H), 9.43 (s, 1H).

Inhibitor G

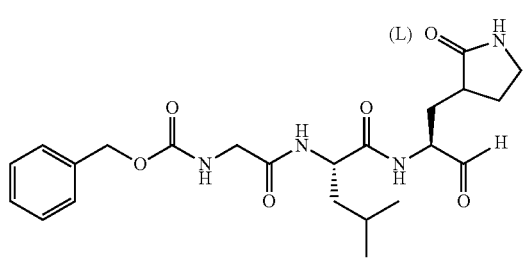

Yellow solid (0.63 g, 67.0% yield), mp 68-70° C. 1H NMR (CDCl₃): δ 0.80-1.10 (d, 6H), 1.40-2.00 (m, 8H), 2.30-2.50 (m, 2H), 3.20-3.40 (m, 2H), 3.79-3.90 (m, 1H) 4.03-4.21 (m, 2H), 4.60-4.71 (m, 1H), 5.00-5.20 (s, 2H), 6.00-6.20 (d, 1H), 6.65 (d, 1H), 7.20-7.40 (m, 5H), 8.70 (s, 1H), 9.42 (s, 1H).

Inhibitor G

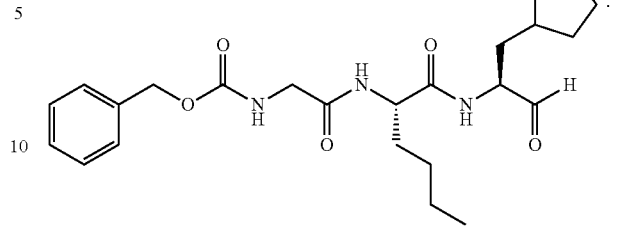

Yellow solid (0.56 g, 46% yield), mp 55-57° C. 1H NMR (CDCl₃): δ 0.80-0.90 (s, 3H), 1.20-1.40 (m, 4H), 1.75-2.00 (m, 4H), 2.30-2.50 (m, 2H), 3.20-3.35 (m, 2H), 3.80 (m, 2H), 4.00-4.19 (m, 2H), 4.60 (m, 1H), 5.00-5.17 (s, 2H), 5.71 (s, 1H), 6.00 (s, 1H), 6.49 (s, 1H), 7.20-7.38 (m, 5H), 8.79 (s, 1H), 9.40 (s, 1H).

Inhibitor J precursor

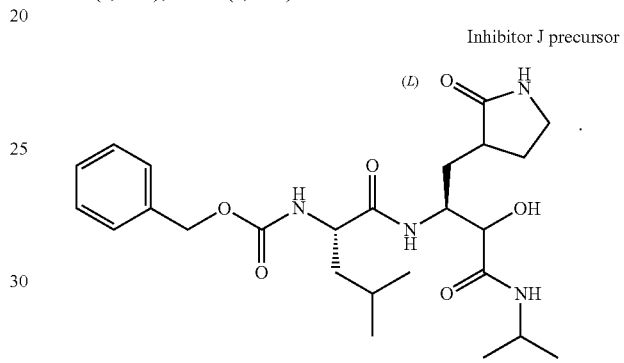

To a solution of inhibitor D (1.03 g, 2.55 mmol) in ethyl acetate (10 mL) kept at 0° C. was added acetic acid (0.177 g, 2.95 mmol) followed by isopropyl isonitrile (0.184 g, 2.58 mmol) and the mixture was stirred at RT for 18 h. The solution was concentrated to dryness and the residue was dissolved in methanol (~10 mL) and treated with an aqueous solution of potassium carbonate (0.85 g, 6.15 mmol) in water (10 mL). The reaction mixture was stirred at RT for 2 h and methanol was removed using a rotary evaporator. The aqueous layer was extracted with ethyl acetate (3×50 mL) and the combined organic layers were washed with 5% hydrochloride acid (2×50 mL) and brine (50 mL). The organic layer was dried over sodium sulfate, filtered and concentrated, leaving a white crystalline solid (0.89 g, 73.3% yield), mp 78-80° C. 1H NMR (CDCl₃): δ 0.90-1.05 (d, 6H), 1.05-1.22 (m, 6H), 1.40-1.93 (m, 6H), 2.25-2.56 (m, 2H), 3.20-3.40 (m, 2H), 4.00-4.40 (m, 2H), 5.00-5.2 (s, 2H), 5.56 (d, 1H), 6.00 (d, 1H), 6.77 (d, 1H), 7.20-7.40 (m, 5H).

Inhibitor J (aka GC375)

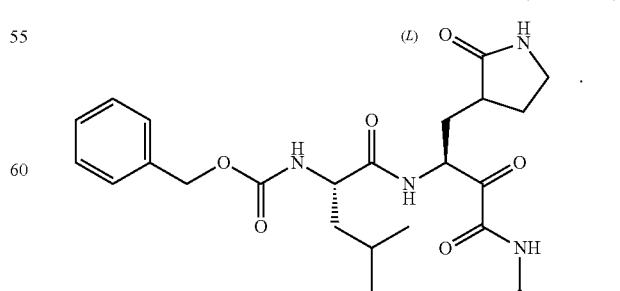

A solution of inhibitor J precursor (0.76 g, 1.6 mmol) in anhydrous DCM (10 mL) kept under nitrogen was treated with Dess-Martin reagent (15% wt in dichloromethane, 10.03 g, 3.55 mmol) with stirring. The reaction mixture was stirred at RT for 1 h (the reaction was monitored by TLC until the disappearance of Inhibitor B). The solvent was removed, leaving a yellow oil which was purified by flash chromatography to give a yellow oil mixed with solid. The mixture was treated with chloroform (5 mL) and the solid was filtered off by suction filtration. The filtrate was dried over anhydrous sodium sulfate, filtered and concentrated, leaving a yellow crystalline solid. (0.57 g, 75.3% yield), mp 145-147° C. 1H NMR (CDCl$_3$): δ 0.90-1.05 (d, 6H), 110-1.30 (m, 6H), 1.40-1.62 (m, 1H), 1.60-1.80 (m, 3H), 1.80-2.00 (m, 2H), 2.40-2.60 (m, 2H), 3.31-3.40 (m, 2H0, 4.00-4.05 (q, 12.5 Hz, 1H), 4.26-4.38 (m, 1H), 5.00-5.19 (s, 2H), 5.20-5.30 (m, 1H), 5.80 (s, 1H), 6.70 (d, 1H), 7.23 (m, 5H), 8.37 (d, 1H).

Bisulfite adduct form of Inhibitor D (aka GC 376)

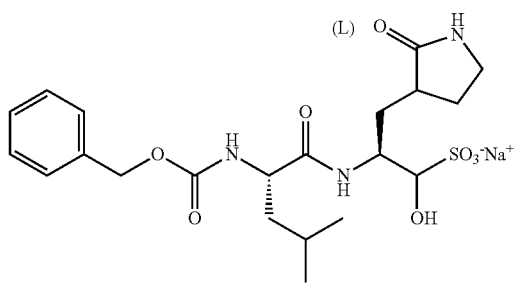

Inhibitor D (GC373) (0.50 g, 1.24 mmol), sodium bisulfite (0.119 g, 1.12 mmol), ethyl acetate (2 mL), ethanol (1 mL) and water (0.40 mL) were combined and heated to 40° C. using a water bath. The reaction mixture was stirred for 2 h and then allowed to cool to ambient temperature. The solution was filtered and washed with ethanol (5 mL). The filtrate was dried over sodium sulfate, filtered, and concentrated leaving a yellow oil, which was treated with ethyl ether (2×3 mL) to give a yellow solid (0.47 g, 74.8% yield), mp 135-137° C. 1H NMR (CDCl$_3$): δ 0.80-0.95 (d, 6H), 1.38-2.00 (m, 6H), 2.00-2.22 (d, 2H), 2.20-2.50 (m, 2H), 3.20-3.40 (m, 2H), 4.20-4.39 (m, 1H), 4.40-4.50 (m, 1H), 5.10 (s, 2H), 5.25 (d, 1H), 5.40 (d, 1H), 7.20-7.41 (m, 5H).

Tripeptidyl bisulfite salt

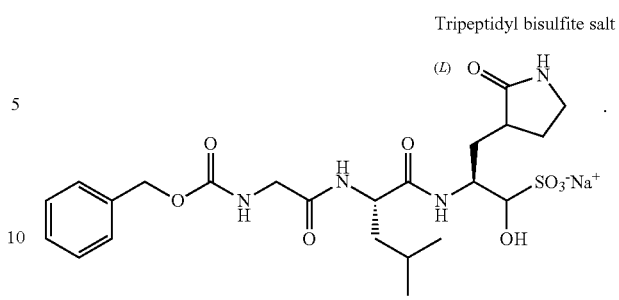

White solid (0.09 g, 71.4% yield), mp 125-127° C. 1H NMR (CDCl$_3$): δ 0.7 0-0.90 (m, 6H), 1.40-2.00 (m, 8H), 2.30-2.52 (m, 2H), 3.20-3.40 (m, 2H), 3.79-3.90 (m, 1H), 4.03-4.21 (m, 2H), 5.00 (s, 2H), 5.19 (d, 1H), 5.50 (s, 2H), 7.20-7.40 (m, 5H).

Tripeptidyl bisulfite salt

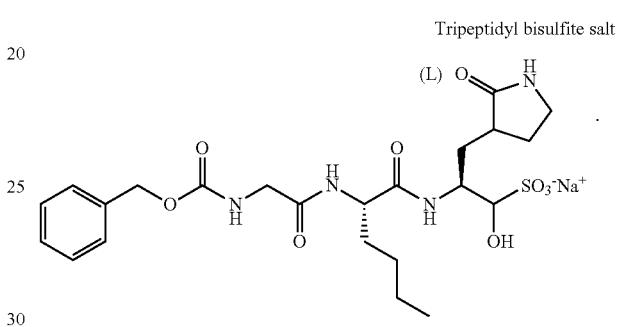

White solid (0.25 g, 89.3% yield), mp 128-130° C. 1H NMR (CDCl$_3$): δ 0.70-0.90 (s, 3H), 1.10-1.30 (m, 4H), 1.45-1.80 (m, 4H), 1.85-2.25 (m, 2H), 3.00-3.25 (m, 2H), 3.60-3.80 (m, 2H), 4.00-4.19 (m, 2H), 4.40 (m, 1H), 5.00 (s, 2H), 5.22 (d, 1H), 5.44 (d, 1H), 7.20-7.40 (m, 5H).

Results and Discussion

1. Toxicity of the compounds. Inhibitor D (also referred to herein as "GC373"), Inhibitor J (also referred to herein as "GC375"), and the bisulfite adduct inhibitor referred to herein as "GC376" did not show any cytotoxicity in the various cells up to 500 μM.

2. The effects of the compounds on various proteases and virus replication. In protease assay, GC373 and GC376 were efficient inhibitors of various viruses except HAV while GC375 was also a good inhibitor against most enzymes including HAV (Table 3), suggesting these compounds were broad-spectrum inhibitors for multiple enzymes.

TABLE 3

The effects of compound GC373, GC375 and GC376 on the protease of various viruses in enzyme assay

| | Inhibition [ED$_{50}$ (μM)] against various viruses | | | | | | | | | |
|---|---|---|---|---|---|---|---|---|---|---|
| | | Calicivirus | | Coronavirus | | | | Picornavirus | | |
| Compound | HG23 cells | FCV | MNV-1 | TGEV | FIPV | MHV | 229E | HAV | Teschovirus | EV71 |
| GC373 | 2.1 | 65 | 6.5 | 0.3 | 0.3 | 2 | 0.2 | >100 | 0.15 | 11 |
| GC375 | 3.2 | 4.5 | 85 | 0.2 | 1.5 | 4.5 | 0.15 | 20 | 0.2 | 15 |
| GC376 | 1.8 | 35 | 5.3 | 0.15 | 0.2 | 1.1 | 0.3 | 50 | 0.15 | 10 |

Cell culture system confirmed the broad-spectrum activity of these compounds to various virus replication using different cell types determined by TCID50 (Table 4), real time qRT-PCR and/or Western blot analysis.

TABLE 4

The effects of compound GC373, GC375 and GC376 in the replication of various viruses in cell culture

| | Inhibition [IC$_{50}$ (μM)] against recombinant 3C or 3CL | | | | | | | |
|---|---|---|---|---|---|---|---|---|
| | Calicivirus | | Picornavirus | | | | Coronavirus | |
| Compound | NV | MD145 | HAV | HRV | Polio V | FMDV | TGEV | SARS-Co |
| GC373 | 2.7 | 20.3 | >100 | 0.3 | 3.6 | 0.4 | 1.7 | 45 |
| GC375 | 5.5 | 6.4 | 36.5 | 0.2 | 2.8 | 0.8 | 2.8 | 5.1 |
| GC376 | 1.3 | 9.8 | >100 | 0.4 | 1.5 | 0.6 | 0.4 | 4.0 |

These results were especially significant because these compounds are able to enter cells and inhibit the enzyme within the cells, and consequently block virus replication at low concentrations. Furthermore, these compounds did not show any toxicity up to 500 μM, suggesting there are high potentials to develop the compounds as antivirals.

In conclusion, members of these series of compounds can be developed as antiviral therapeutics targeting a specific virus or, more importantly, they can be developed as broad-spectrum antivirals targeting multiple viruses. The wide applicability of the latter would constitute a significant advance in antiviral research and public health.

Example 3

Additional Study and Analysis of Viral Protease Inhibitors

In this Example: a FRET-based assay for norovirus 3CLpro is described; NV replicon-harboring cells have been established and the feasibility of using them for the discovery of potential antiviral therapeutics for norovirus infection has been demonstrated; initial series of peptidyl transition state (TS) inhibitors incorporating in their structure a glutamine surrogate have been designed (FIG. 8); and the inhibitory activities of the compounds have been investigated toward norovirus 3CLpro, as well as in NV replicon-harboring cells; the binding and detailed interactions, as well as the mechanism of action of NV 3CLpro with one of the compounds (GC376), were probed using X-ray crystallography and high-field NMR; three compounds were used to obtain a preliminary evaluation of their physicochemical properties using in vitro ADMET, rat PK and oral bioavailability; and finally, the effect of one of the inhibitors (GC376) on norovirus replication in vivo using the gnotobiotic pig model has been investigated. The results of these studies are briefly summarized below.

1. Antiviral Compounds

Figures 8, 9:
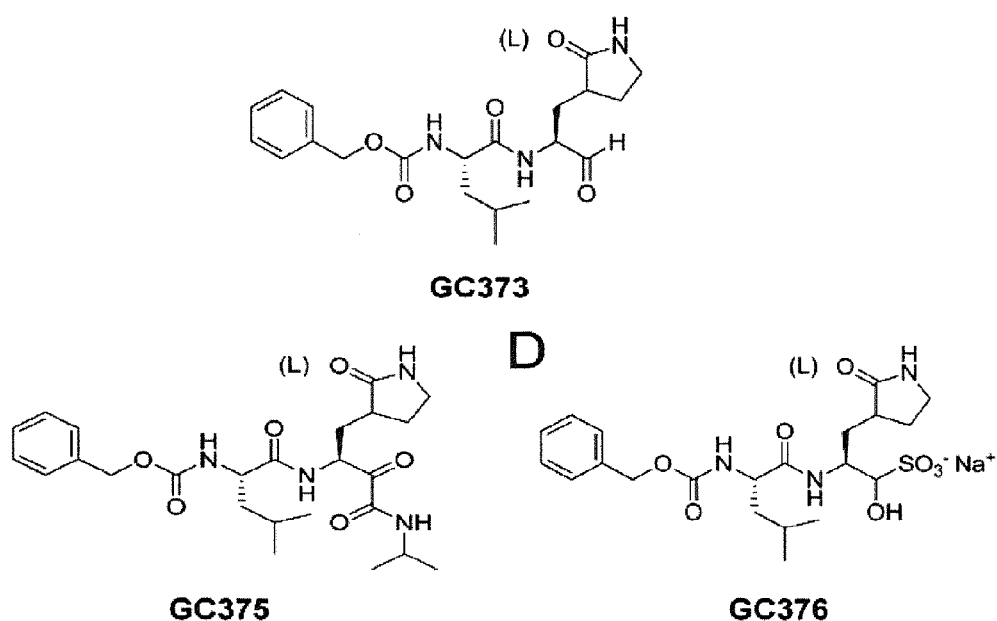
FIG. 8 illustrates three dipeptidyl compounds synthesized and examined in Example 2.
FIG. 9 is a table showing the effects of GC373, 375, and 376 on the 3CL protease of NV, MD145, MNV-1 in the FRET protease assay.

GC373, GC375, and GC376 were synthesized as described above in Example 2, and correspond to formulas (III), (IV), and (II), respectively described in the specification. The structures of the dipeptide inhibitors are shown in FIG. 9. Rupintrivir, a protease inhibitor designed against HRV 3C protease, was purchased from Axon Medchem (Groningen, Netherlands) and used as a control.

2. Cells, Viruses, and Reagents

Various cell lines, including HG23 cells (Huh-7 cells containing an NV replicon)(8), CRFK, RAW267.4, ST, CCL-9.1, MRC-5, FRhK-4, HeLa, and Vero cells, were maintained in Dulbecco's minimal essential medium (DMEM) or MEM containing 5% fetal bovine serum and antibiotics (chlortetracycline [25 μg/ml], penicillin [250 U/ml], and streptomycin [250 μg/ml]). All cells except HG23 cells were obtained from ATCC (Manassas, Va.). Viruses used in this study were FCV (strain Urbana), MNV-1, TGEV (strain Miller), BCV (a field isolate from Kansas State University [KSU] diagnostic lab), FIPV (strain 1146), human coronavirus 229E, MHV (strain A59), HAV (strain HM175), PTV (a field isolate from the KSU diagnostic lab), enterovirus 71 (strain H), and HRV (strains 18, 51, and 68). FCV and MNV-1 were obtained from Dr. Green at the NIH, and Dr. Virgin at Washington University (St. Louis, Mo.), respectively. BCV and PTV were obtained from the KSU diagnostic lab. All other viruses were obtained from ATCC.

3. Expression and Purification of 3Cpro and 3CLpro

The cDNAs encoding full length viral 3Cpro or 3CLpro of TGEV and HAV were amplified by reverse transcription-PCR (RT-PCR). Primers contained the nucleotide sequences of each corresponding protease, for cloning, as well as the nucleotides for 6 His (in the forward primers). The codon-optimized cDNAs for 3Cpro or 3CLpro of NV, MD145, SARS-CoV, PV, and FMDV were synthesized fused with 6 His at the N-terminal (Genscript, Piscataway, N.J.). Each synthesized gene or amplified product was subcloned into the pET-28a(+) vector. The expression and purification of each protease were performed by a standard method described previously by our lab (Takahashi et al., Biomol NMR Assign 85:12570-77 (2012)). Recombinant HRV 3Cpro was purchased from EMD chemicals, Inc. (Gibbstown, N.J.).

4. Biochemical Studies and Assay Development. Preliminary FRET Assay for Norovirus 3CLpro from NV, MD145 and MNV-1.

Noroviruses show high genetic diversity with at least five genogroups, GI-GV, of which GI and GII are responsible for the majority of norovirus infections in humans. The codon-optimized, full-length 3CLpro from human [NV (GI), MD145 (GII)], and murine [MNV-1 (GV)] noroviruses, as well as the mutant NV 3CLpro (C139A) with Cys (nucleophile) substitution with Ala at position 139 were generated and their enzymatic activities were characterized using FRET substrates.

Two fluorogenic substrates, Edans-EPDFHLQGPED-LAK-Dabcyl (SEQ ID NO:1) and Edans-DFHLQGP-Dabcyl (residues 3-9 of SEQ ID NO:1) derived from the P7-P7' and P5-P2' residues on the NS2/3 cleavage site in ORF1 of NV (FIG. 1), respectively, were used to optimize the FRET assay. All three proteases exhibited enzymatic activity with similar cleavage efficiency ($k_{cat}/K_m$), suggesting that the proteases are able to efficiently recognize and cleave the substrates derived from a cleavage site of GI norovirus. The proteases showed higher cleavage efficiency towards the shorter substrate, as indicated by higher $k_{cat}/K_m$ values, compared to the 14-residue substrate. As expected, the mutant NV protease (C139A) did not increase the fluorescence signal on addition of substrate. The mean Z factor for our FRET-based protease assay using NV and MD145 3CLpro and Edans-DFHLQGP-Dabcyl (residues 3-9 of SEQ ID NO:1) as a substrate was calculated as being in the 8-0.9 range, demonstrating an excellent signal-to-background ratio. In short, the FRET-based assay exhibits robustness, high sensitivity, and is amenable to HTS. The effects of three inhibitors on the activity of 3CLpro using the optimized FRET-based protease assay are summarized in FIG. 9. GC373 (dipeptidyl aldehyde) and GC376 (bisulfite adduct form of GC373) were highly effective against the proteases (NV, MD145, MNV-1) (FIG. 8-9). The inhibitory activity of GC375 (α-ketoamide) was also demonstrated against these proteases but was lower than those of GC373 and GC376.

5. Preliminary Study of Effect on Replication of NV, FCV and MNV-1.

The overall effects of the three compounds on the replication of various viruses in cell based assays are in line with those in the protease assay. Both GC373 and GC376 were highly effective against caliciviruses (NV and MNV-1) with nM or low μM $ED_{50}$ values (FIG. 10). As shown with the protease assay, GC375 was less effective against the replication of caliciviruses than GC373 and GC376. In this study, all compounds did not show any non-specific cytotoxicity up to 500 μM in the cells used for virus replication. FCV, a vesivirus, was less sensitive to GC373 and GC376 with IC50 values of 65 and 35 μM, respectively, compared to noroviruses (FIG. 10).

6. Broad-Spectrum Activity of GC373, GC375 and GC376.

Because calicivirus 3CLpro share similar structural and functional characteristics to that of the picornaviruses and coronaviruses, we examined the effect of GC373, GC375 and GC376 compounds against those viruses in enzyme and cell-based assays. We included human rhinovirus (HRV), enterovirus 71 (EV71), poliovirus (PV), foot-and-mouth disease virus (FMDV), hepatitis A virus (HAV), and porcine teschovirus (PTV) (Picornaviridae); human 229E coronavirus, transmissible gastroenteritis virus (TGEV), murine hepatitis virus (MHV), bovine coronavirus (BCV), feline infectious peritonitis virus (FIPV), and severe acute respiratory syndrome coronavirus (SARS-CoV)(Coronaviridae) in the study. All compounds were found to be highly effective against the majority of tested picornaviruses and coronaviruses with the IC50 values in the high nM or low μM range against 3CLpro (FIG. 11) or in cell-based (FIG. 12-13) assays, and a high therapeutic index.

a. FRET-Based Assay

Fluorogenic substrates with Edans and Dabcyl as a donor and quencher pair were purchased from Bachem (coronavirus substrate) or synthesized by GenScript. The viral proteases and the corresponding fluorogenic substrates are listed in Table 5, along with their sources.

TABLE 5

| Virus family and virus | Fluorogenic substrates | pH | Buffer conditions[b] Glycerol (%) | DTT (mM) | NaCl (mM) |
|---|---|---|---|---|---|
| *Caliciviridae* | | | | | |
| NV | Edans-DFHLQ/GP-Dabcyl [truncated] (residues 3-9 SEQ ID NO: 1) | 8 | 60 | 6 | 120 |
| MD145 | Edans-DFHLQ/GP-Dabcyl (residues 3-9 SEQ ID NO: 1) | 8 | 60 | 6 | 120 |
| *Coronaviridae* | | | | | |
| TGEV | Dabcyl-KTSAVLQ/SGFRKME-Edans (SEQ ID NO: 2) | 6 | 30 | 4 | 120 |
| SARS-CoV | Dabcyl-KTSAVLQ/SGFRKME-Edans (SEQ ID NO: 2) | 6 | 30 | 4 | 120 |
| *Picornaviridae* | | | | | |
| PV | Dabcyl-KTSAVLQ/SGFRKME-Edans (SEQ ID NO: 2) | 8 | 20 | 4 | 120 |
| HRV | Edans-DFHLQ/GP-Dabcyl (residues 3-9 SEQ ID NO: 1) | 7 | 20 | 4 | 120 |
| HAV | Dabcyl-GLRTQ/SFS-Edans (SEQ ID NO: 3) | 7 | 20 | 4 | 120 |
| FMDV | Edans-APAKQ/LLN-Dabcyl (SEQ ID NO: 4) | 8 | 50 | 4 | 120 |

[a]NV, norovirus strain Norwalk; MD145, norovirus strain MD145; TGEV, transmissible gastroenteritis virus; SARS-CoV, severe acute respiratory syndrome coronavirus; PV, poliomyelitis virus; HRV, human rhinovirus; HAV, human hepatitis A virus; FMDV, foot-and-mouth disease virus.
[b]The buffer contained 20 mM HEPES and 0.4 mM EDTA.

The designation of substrate residues for P1 and P1' starts at the scissile bond and counts toward the N- or C-termini, respectively. The fluorescence resonance energy transfer (FRET) protease assay was performed as follows.

Stock solutions (10 mM) of the substrates and the compounds were prepared in dimethyl sulfoxide (DMSO) and diluted in assay buffer. The assay buffer comprised 20 mM HEPES buffer containing NaCl (0 mM for HAV 3Cpro and 200 mM for all other proteases), 0.4 mM EDTA, Glycerol (60% for NV and MD145 3CLpro and 30% for TGEV and 229E 3CLpro), and 6 mM (NV and MD145 3CLpro and HAV 3Cpro) or 4 mM (all other proteases) dithiothreitol (DTT) at pH 6 (coronavirus 3CLpro) or 8 (all other proteases). Each protease was mixed with serial dilutions of each compound or with DMSO in 25 µl of assay buffer and incubated at 37° C. for 30 min, followed by the addition of 25 µl of assay buffer containing substrate. Fluorescence readings were obtained using an excitation wavelength of 360 nm and an emission wavelength of 460 nm on a fluorescence microplate reader (FLx800; Biotek, Winooski, Vt.) at 1 h following the addition of substrate. The relative fluorescence units (RFU) were determined by subtracting background values (substrate-containing well without protease) from the raw fluorescence values. The dose-dependent FRET inhibition curves were fitted with a variable slope by using GraphPad Prism software (GraphPad, La Jolla, Calif.) in order to determine the $IC_{50}$s of compounds.

The toxic dose for 50% cell death ($TD_{50}$) for each compound was determined for the various cells used in this study. Confluent cells grown in 96-well plates were treated with various concentrations (1 to 500 µM) of each compound for 72 h. Cell cytotoxicity was measured by a CytoTox 96® nonradioactive cytotoxicity assay kit (Promega, Madison, Wis.) and crystal violet staining. The In vitro therapeutic index was calculated by dividing the $TD_{50}$ by the $IC_{50}$.

The effects of the compounds as well as rupintrivirin optimized FRET protease assays are summarized in FIG. 11. GC373 (dipeptidyl aldehyde), was previously shown to be effective against NV3CLpro, inhibited the activities of all viral proteases except HAV 3Cpro; it was effective against the proteases of caliciviruses (NV and MD145 virus); coronaviruses (TGEV and SARS-CoV), and picornaviruses (PV, FMDV and HRV), with $IC_{50}$s ranging from 0.61 to 3.48 µM under our assay conditions (FIG. 11). The effects and range of inhibition of GC376 were comparable to those of GC373 against various 3Cpro or 3CLpro. The inhibitory effects of GC375 (dipeptidyl α-ketoamide) were moderate (2.87 to 4.02 µM) against the proteases of caliciviruses (FIG. 11). However, the inhibitory activities of GC375 against the proteases of picornaviruses and coronaviruses were comparable to those of GC373 and GC376 (FIG. 11). In addition, GC375 showed weak but appreciable inhibitory effects on HAV 3Cpro compared to GC373 and GC376. Rupintrivir, used as a control, showed similar activities against calicivirus and picornavirus proteases compared to GC373 and GC376 but was substantially less effective against the coronavirus proteases (FIG. 11).

b. Cell Culture System

The effects of each compound on viral replication were examined in cell culture systems. Virus-infected cells were incubated at 37° C., except for HRV-infected HeLa cells, which were maintained at 33° C. The viruses and corresponding cell lines are listed in Table 6.

TABLE 6

| Virus family | Virus[a] | Cell line |
| --- | --- | --- |
| Caliciviridae | NV | HG23 |
|  | FCV | CRFK |
|  | MNV-1 | RAW267.4 |
| Coronaviridae | TGEV | ST |
|  | FIPV | CRFK |
|  | 229E | MRC-5 |
|  | MHV | CCL-9.1 |
|  | BCV | HRT-18 |
| Picornaviridae | HAV | FRhK-4 |
|  | EV71 | Vero |
|  | HRV 18, 51, 68 | HeLa |
|  | PTV | ST |
|  | Cox A9, B2, B3 | HeLa |

[a]MNV-1, murine norovirus-1; FIPV, feline infectious peritonitis virus; 229E, human coronavirus 229E; MHV, mouse hepatitis virus; BCV, bovine coronavirus; EV71, Enterovirus 71; HRV 18, 51, and 68, human rhinovirus strains 18, 51, and 68; PTV, porcine teschovirus; Cox, coxsackievirus.

Briefly, confluent or semiconfluent cells were inoculated with virus at a multiplicity of infection of 0.05 for 1 h, and the inoculum was replaced with medium containing DMSO (<0.1%) or each compound (up to 100 The virus-infected cells were further incubated for up to 168 h, and the replication of virus was measured by the 50% tissue culture infectious dose ($TCID_{50}$) method and/or real time quantitative RT-PCR (qRT-PCR). The $TCID_{50}$ method was used for titration of viruses showing apparent cell cytopathic effects, which included FCV, MNV-1, TGEV, FIPV, MHV, BCV, HAV, 229E, EV71, and PTV. Real-time qRT-PCR was performed for titration of NV (replicon-harboring cells) and HRV. For HAV and 229E, real time qRT-PCR was also used to confirm the $TCID_{50}$ results. For real-time qRT-PCR, RNA was extracted from each sample (cell lysates for HG23 cells and viral suspensions for HAV, HRV, and 229E) by the use of an RNeasy kit (Qiagen, Valencia, Calif.), followed by amplification in a Cepheid SmartCycler with the following parameters: 45° C. for 30 min and 95° C. for 10 min followed by 40 cycles of denaturation at 95° C. for 30s, annealing at 50° C. for 1 min, and elongation at 72° C. for 30 s. The primers and probes used for real-time qRT-PCR are listed in Table 7 below. The $IC_{50}$s were determined by GraphPad Prism software.

TABLE 7

```
VirusSequences

NV    5'-CGYTGGATGCGNTTYCATGA-3' (SEQ ID NO: 5);
      5'-CTTAGACGCCATCATCATTYAC-3' (SEQ ID NO: 6);
      6-carboxyfluorescein (FAM)-5'-AGATYGCGATCYCCTGTCCA-3'-6-
      carboxytetramethylrhodamine (TAMRA) (SEQ ID NO: 7)

HAV   5'-ACTGCAGTGACTGGTGCTTC-3' (SEQ ID NO: 8);
      5'-CCG GGTTTATCAACAGAGGT-3' (SEQ ID NO: 9);
      FAM-5'-CCTGGTGTGATCCAACCTCAGCTG-3'-IABkFQ (SEQ ID NO: 10)

HRV   5'-TGTTCYAGCCTGCGTGGC-3' (SEQ ID NO: 11);
      5'-GAAACACGGACACCCAAAGTA-3' (SEQ ID NO: 12);
      FAM-5'-TCCTCCGGCCCCTGAATGYGGC-3'-IABkFQ (SEQ ID NO: 13)
```

TABLE 7-continued

VirusSequences 229E 5'-TTCCGACGTGCTCGAACTTT-3' (SEQ ID NO: 14);
    5'-CCAACACGGTTGTGACAGTGA-3' (SEQ ID NO: 15);
    FAM-5'-TCCTGAGGTCAATGCA-3'-IABkFQ (SEQ ID NO: 16)

Figures 13, 14:
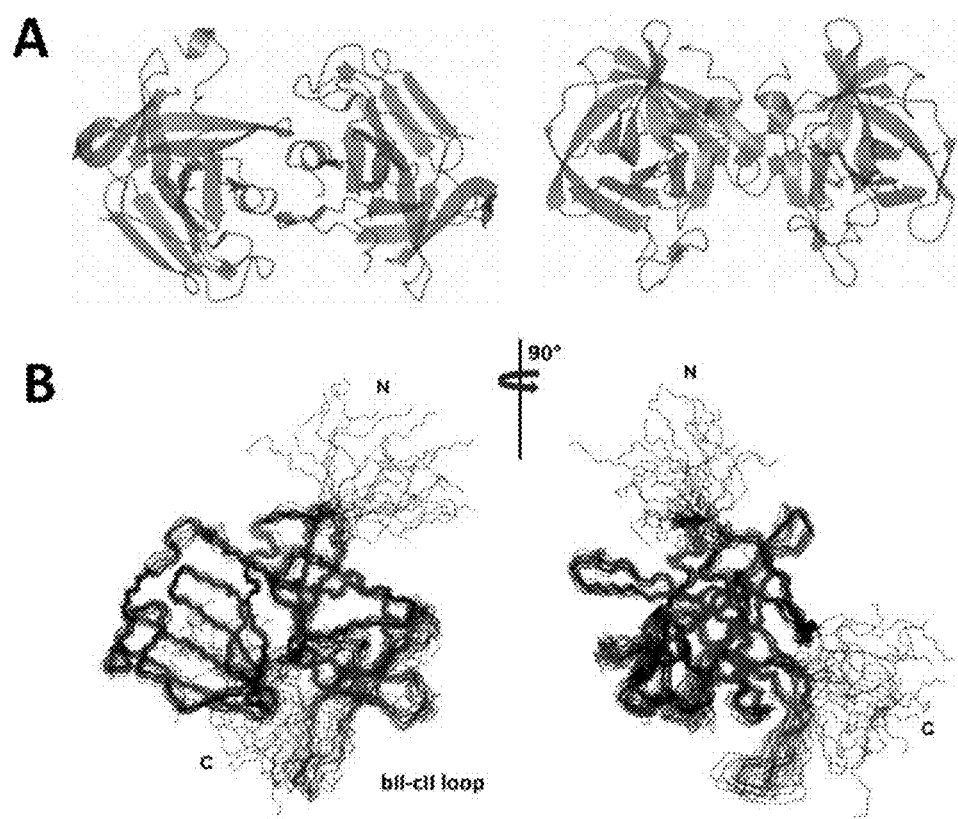
FIG. 13 is an additional table of the effects of GC373, 375, and 376 on the replication of various viruses in cell culture.
FIG. 14 is an illustration of the apo NV3CL protease structure solved by X-ray crystallography and NMR showing the (A) dimer form of NV 3CL protease by X-ray crystallography; and (B) solution structure of NV 3CL protease by NMR with backbone overlays of the 20 lowest energy structures. The a-helix is colored in red and the b-strand in blue, and a large structural variation was observed in bII-cII β-sheet region as well as N- and C-terminal segments.

The overall effects of the compounds on the replication of various viruses in the cell-based assays were in line with those in the protease assay (FIG. 12-13). Both GC373 and GC376 were significantly effective against caliciviruses (NV and MNV-1), coronaviruses (TGEV, FIPV, MHV, 229E, and BCV), and picornaviruses (HRVs18, 51, and 68, EV71, and PTV), with nanomolar or low micromolar $IC_{50}$s, except FCV and HAV (FIG. 12-13). Interestingly, FCV was less sensitive to GC373 and GC376, with $IC_{50}$s of 65 and 35 µM, respectively (FIG. 12). As shown with the protease assay, GC373 and GC376 showed no or weak effectiveness against the replication of HAV in cells. GC375 showed significant antiviral effects against NV and all coronaviruses and picornaviruses, including HAV, but no effects against FCV and MNV-1 at concentrations up to 50 µM (FIG. 12-13). Rupintrivir inhibited the replication of NV (in HG23 cells), TGEV, FIPV, 229E, BCV, HRV strains 18, 51, and 68, EV71, and PTV, with various potencies. Note that rupintrivir did not inhibit the replication of MNV-1, FCV, and MHV at concentrations up to 50 µM or 100 µM. All compounds, including rupintrivir, did not show any non-specific cytotoxicity at concentrations up to 500 µM in the cells used for virus replication in this study.

7. Structural Studies—X-Ray Crystallography and High-Field NMR Studies

To place the design and subsequent optimization of the NV 3CLpro inhibitors on a secure structural and biochemical footing, structural studies were initiated. Purified NV 3CLpro, PV 3Cpro and TGEV 3CLpro concentrated to 10 mg/mL in 100 mM NaCl, 50 mM PBS pH 7.2, 1 mM DTT were used to prepare complexes with GC376. All crystallization screening was conducted in Compact Jr. (Emerald Biosystems) sitting drop vapor diffusion plates at 20° C. using equal volumes of protein and crystallization solution equilibrated against 75 µL of the latter. A 100 mM stock solution of GC376 was prepared in DMSO and complexes with the proteases were prepared as follows. NV 3CLpro-GC376:290 µL of NV 3CLpro (0.48 mM) was mixed with 10 µL of GC376 (3.3 mM) and PV 3Cpro-GC376:392 µL of PV 3Cpro (0.48 mM) was mixed with 8 µL of GC376 (2.0 mM). TGEV 3CLpro-GC376: 490 µL of TGEV 3CLpro (0.48 mM) was mixed with 10 µL of GC376 (2.0 mM). The complexes were incubated on ice for 1 hr and loaded onto a Superdex 75 10/300 GL column equilibrated with 100 mM NaCl, 20 mM Tris pH 8.0. Then the elution fractions were pooled and concentrated in a Vivaspin-20 concentrator (MWCO=10 kDa) to 14, 9.7, and 10.7 mg/mL for NV 3CLpro, PV 3Cpro, and TGEV 3CLpro, respectively, for crystallization.

Crystals were obtained from the following conditions. NV 3CLpro: Apo crystals, displaying a prismatic morphology, were obtained in 24 hrs from Wizard 3 screen (Emerald Biosystems) condition #10 (20% [w/v] PEG 3350, 100 mM sodium thiocyanate). Needle shaped crystals were obtained in 24 hrs from the NV3CLpro-GC376 complex were obtained in 24 hrs from the Wizard 4 screen (Emerald Biosystems) condition #25 (30% [w/v] PEG 2000MME, 150 mM sodium bromide). PV 3Cpro-GC376: Plate shaped crystals were obtained in 24 hrs from Wizard 3 screen (Emerald Biosystems) condition #47 (30% [w/v] PEG 5000MME, 100 mM MES pH 6.5, 200 mM ammonium sulfate). TGEV 3CLpro-GC376: A cluster of plate shaped crystals were obtained in 48 hrs from Wizard 3 screen (Emerald Biosystems) condition #1 (20% [w/v] PEG 3350, 200 mM sodium acetate). All crystals, except those of the NV 3CLpro-GC376 complex, were transferred to a solution containing 80% crystallization and 20% PEG 400 and frozen in liquid nitrogen for data collection. For the NV 3CLpro-GC376 complex, 20% PEG 200 was used as the cryoprotectant. X-ray diffraction data were collected at the Advanced Photon Source beamline 17-ID using a Dectris Pilatus 6M pixel array detector.

For all structures, the following software was used unless specified otherwise. Intensities were integrated using XDS and the Laue class check and data scaling were performed with Pointless and Scala. Structure solution was conducted by molecular replacement with Molrep for the NV 3CLpro structures and Phaser via the Phenix interface for all other structures. Refinement and manual model building were conducted with Phenix and Coot respectively. TLS refinement was incorporated in the latter stages of refinement for the NV 3CLpro and PV 3Cpro structures, to model the anisotropic atomic displacement parameters of the protein atoms. Structure validation was conducted with Molprobity and figures were prepared using the CCP4MG package. Disordered side chain atoms were truncated to the point where electron density could be observed.

For apo NV 3CLpro, the highest probability Laue class was 2/m and space group P21 and the Matthew's coefficient (Vm) and solvent content were estimated to be Vm=3.7/67.0% solvent and Vm=1.9/34.0% solvent for 1 and 2 molecules in the asymmetric unit, respectively. Molecular replacement searches for two molecules in the asymmetric unit were conducted in the space groups P2 and $P2_1$. A previously determined structure of NV 3CLpro (PDB: 2FYQ) was used as the search model. The top solution was found in the space group P21 that consisted of a non-crystallographic dimer. For the NV 3CLpro-GC376 complex, the highest probability Laue class was mmm and space group $P2_12_12_1$. The Matthew's coefficient (Vm) and solvent content were estimated to be Vm=3.9/68.8% solvent and Vm=2.0/37.6% solvent for 1 and 2 molecules in the asymmetric unit, respectively. Molecular replacement search for two molecules in the asymmetric unit was conducted using the apo NVPro structure as a search model. The highest correlation coefficient (0.672) was obtained in the space group $P2_12_12_1$. Examination of the active site revealed prominent difference in electron density (Fo-Fc) in each subunit greater than 3σ that was consistent with GC376. However, the bisulfite group appeared to have been removed and the inhibitor was covalently bound to Cys 139. The 6-membered aromatic ring of the inhibitor was disordered and could not be fit to the electron density maps due to disorder. Residues between Leu 122-Gly 133 of apo NV 3CLpro chain A and Leu 122-Asn 126 of chain B were disordered and could not be modeled as were the C-terminal residues from Gly 174 to Glu 181.

For the PV 3Cpro-GC376 complex, the highest probability Laue class was mmm and possible space groups $I2_12_12_1$ or I222. The Matthew's coefficient (Vm) and solvent content were estimated to be Vm=2.2/43.0% solvent for 1 molecule in the asymmetric unit. Molecular replacement was conducted using an apo PV 3Cpro structure as the search model (PDB: 1L1N) and the top solution was found in the space group I222. Examination of the active site revealed prominent difference in electron density (Fo-Fc) greater than 3σ that was consistent with GC376 which was covalently bound to Cys 147. Two sulfate ions were included in the model along with a DTT molecule. The latter resides on a crystallographic 2-fold axis. Prominent electron density (Fo-Fc) was observed near the DTT molecule that appeared to be covalently connected. However, the identity of this electron density could not be conclusively confirmed and was not assigned.

For the TGEV 3CLpro-GC376 complex, the highest probability Laue class was 2/m and the most probable space group was $P2_1$. The Matthew's coefficient (Vm) and solvent content were estimated to be Vm=3.1/60.2% solvent and Vm=2.3/46.9% solvent for 3 and 4 molecules in the asymmetric unit, respectively. Molecular replacement was conducted using a previously determined structure of 3CLpro of TGEV as the search model (PDB: 2AMP). The top solution was found in the space group $P2_1$ with 4 molecules in the asymmetric unit. Examination of the active site revealed prominent difference in electron density (Fo-Fc) in each subunit greater than 3a that was consistent with GC376 covalently bound to Cys 144.

a. Crystal Structure of NV 3CLpro Refined to 1.50 Å Resolution

The apo structure (dimer form), which represents a new crystal form of NV 3CLpro, was similar to a previously reported crystal structure of NV 3CLpro (PDB 2FYQ) (FIG. 14A). Superposition of residues Ala 1-Ala 173 of our structure with those of 2FYQ using Superpose via the CCP4 interface yielded root-mean-square deviations (RSMD) of 0.84 Å and 0.77 Å between the Ca atoms for chains A and B, respectively. The largest differences were observed in certain loop regions of the protease, including Met 101 to Arg 112, Lys 146 to Val 152, and Thr 161 to Thr 166, and are not likely due to crystal contacts (coordinates and structure factors for the apo NV 3CLpro have been deposited in the Protein Data Bank, accession code 3UR6). These loop regions are known to be flexible and involved in the substrate recognition and interaction for the protease activity.

We have also established complete backbone and side chain chemical shift assignments and the chemical shift-based secondary structure prediction of NV 3CLpro. The overall fold of NV 3CLpro solution structures agrees well with that of the crystal structures (the structure has been deposited in the Protein Data Bank, accession code 2LNC). A notable difference is an additional short β-strand structure (V72-E74) observed in linker region connecting N- and C-domains of the NV 3CLpro solution structure, which is consistent with our published chemical shift-based secondary structure prediction. FIG. 14B shows superposition of the backbone atom of the 20 lowest energy conformers for NV 3CLpro over residues 1-173.

b. Crystal Structure of NV 3CLpro in Complex with GC376 Refined to 1.65 Å Resolution.

Figure 15:
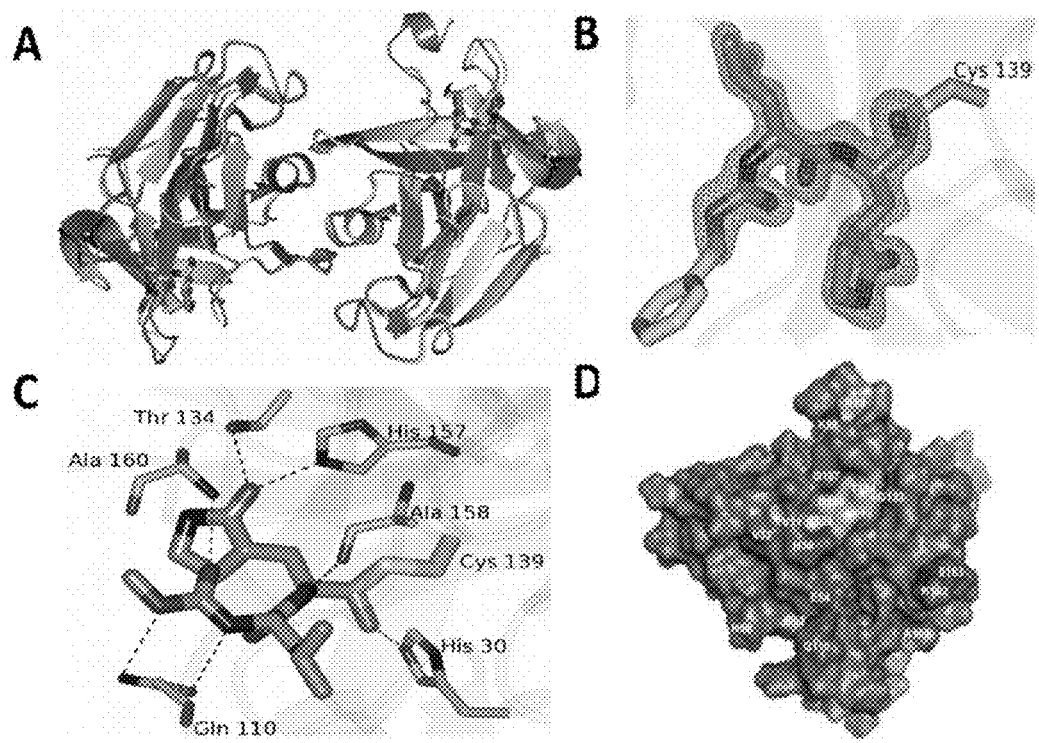
FIG. 15 is an illustration of the interaction of NV 3CL protease and GC376 as determined by X-ray crystallography (A-C) and NMR (D), showing (A) NCS dimer of apo NV3CL protease showing chain A (magenta) and chain B (blue) superimposed with the GC376 bound form showing chain A (cyan) and chain B (green); (B) Fo-Fc omit maps contoured at 3s for GC376, wherein the aromatic ring of the inhibitor not included in the model due to disorder is colored green; (C) hydrogen bonding (dashed lines) interactions between NV3CL protease (cyan) and GC376 (grey); and (D) NV 3CL protease residues changed by binding with GC376. Chemical shift difference values (Δω) of the 1H and 15N resonances were determined and residues that showed peak disappearance (most affected) are indicated by red colors and residues with Δω more than 0.1 ppm by pink color.
Figure 16:
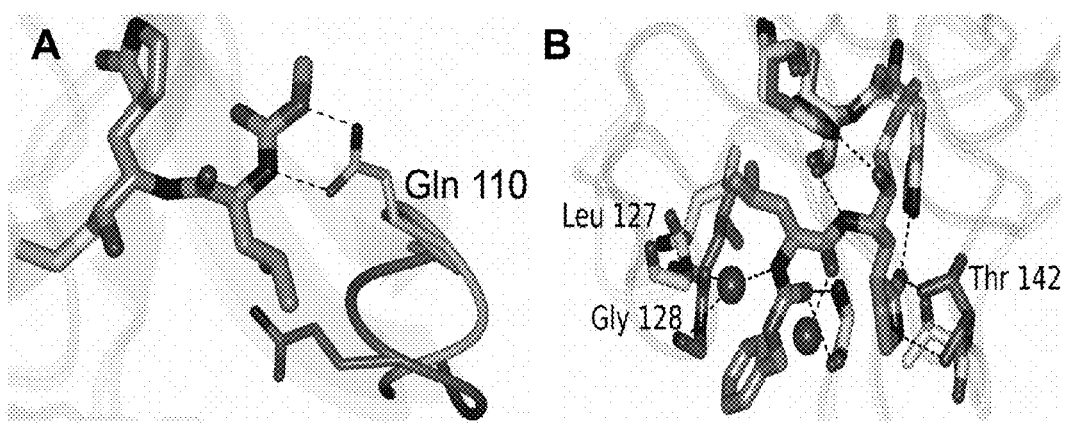
FIG. 16 is an illustration of conformational changes during binding of NV 3CLpro or PV 3Cpro and GC376, showing: (A) Conformational changes in the loop containing Gln 110 in NV 3CLpro that occur upon inhibitor binding. The apo and inhibitor-bound forms are colored magenta and cyan, respectively. The hydrogen bonds that form between Gln 110 and the inhibitor are indicated by dashed lines. (B) Conformational changes in the loops containing Leu 127, Gly 128, and Thr 142 of PV 3Cpro that occur upon ligand binding. The apo and ligand-bound forms are colored green and magenta, respectively. Leu 127 and Gly 128 undergo a conformational change to accommodate a water-mediated hydrogen bond. The red spheres are water molecules.
Figures 17, 18:
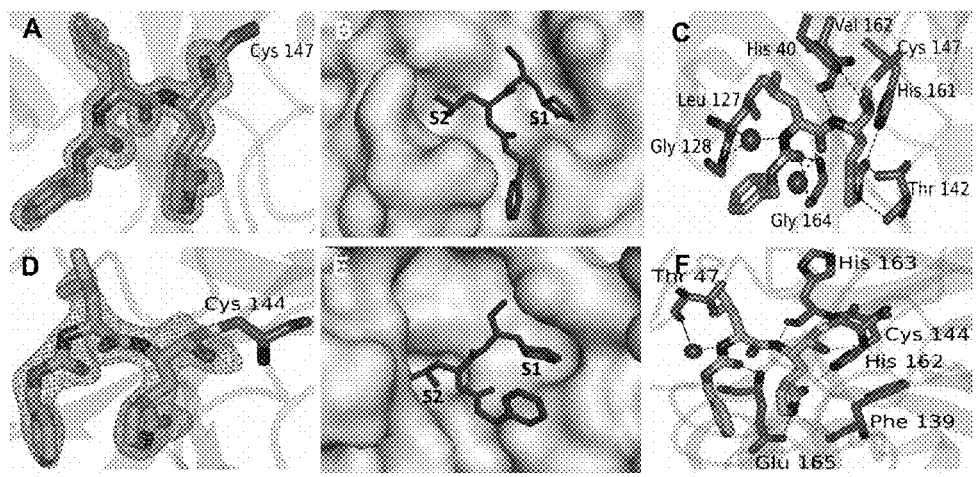
FIG. 17 is an illustration of the PV 3Cpro-GC376 complex showing: (A) Fo-Fc omit map contoured at 3σ for GC376; (B) GC376 (red) in the S1 and S2 positions of the active site of PV 3Cpro (grey); (C) Hydrogen bonding (dashed lines) interactions between PV 3Cpro (magenta) and GC376 (grey); and the TGEV 3CLpro-GC376 complex showing: (D) Fo-Fc omit map contoured at 3σ s for GC376; (E) GC376 (red) in the S1 and S2 positions of the active site of TGEV 3CLpro (grey); and (F) Hydrogen bonding (dashed lines) interactions between PV 3Cpro (magenta) and GC376 (blue). The red spheres in panels C and F are water molecules.
FIG. 18 is a table showing the in vivo PK and oral bioavailability studies in rats.

We have also determined the high resolution structure of the NV 3CLpro-ligand complex using inhibitor GC376. NV3CLpro existed as a noncrystallographic dimer that was nearly identical to that observed for the apo crystal form (FIG. 15A). Examination of the active site revealed a prominent difference in electron density (Fo-Fc) of greater than 3σ in each subunit, consistent with GC376. However, the bisulfite group appeared to have been removed and the compound was converted to the aldehyde form which created a covalent bond with Cys 139 (FIG. 15B-C). The 6-membered aromatic ring of the compound is not included in the modeling due to disorder, which may have resulted from the possibility that the aromatic ring does not bind to the S3 site but faces outwards towards the solvent (FIG. 15B). The glutamine surrogate ring and the Leu of GC376 fit into the S1 and S2 sites, respectively, as expected. The hydrogen bond interactions between the amino acid residues of His 30, Gln 110, Thr 134, His 157, Ala 158 and Ala 160 in NV 3CL pro and GC376 are shown in FIG. 15C. Superposition of residues Ala 1 to Ala 173 of apo NV 3CLpro, with the NV 3CLpro-GC376 complex yielded an RMSD of 0.80 Å and 0.68 Å between Ca atoms for chains A and B, respectively. The largest differences were observed in the loop containing Gln 110 which undergoes a dramatic conformational change to accommodate hydrogen bonding to GC376 (FIG. 16A). Gln 100 and Ala 160 are involved in tight binding to GC376, with large conformational changes in the loops containing those amino acids. All other residues that form hydrogen bonds to the compound are in similar positions in both the apo and ligand bound forms. Comparison of binding interactions between Southampton norovirus 3CLpro with a Michael acceptor inhibitor, acetyl-Glu-Phe-Gln-Leu-Gln-CH=CHCOO⁻ (residues 3-7 of SEQ ID NO:18) and between NV 3CLpro and GC376 demonstrated that the same amino acids were involved in the interactions with the inhibitors. The binding of GC376 and NV 3CLpro was also confirmed by NMR spectroscopy with measuring peak shifts in the presence of various concentrations of GC376 (FIG. 15D).

c. Crystal Structure of PV3Cpro and TGEV 3CLpro in Complex with GC376, Refined to 1.6-Å and 2.25-Å Resolution, Respectively The proteases of a picornavirus (PV3Cpro) and a coronavirus (TGEV 3CLpro) were selected to study the interaction with GC376 in comparison to that with NV3CLpro (FIG. 17A-F). Examination of the active site revealed prominent difference in electron density ($F_o$-$F_c$) in each subunit (>3σ) that was consistent with GC376 (FIG. 17A, D). Like the case with NV 3CLpro, the glutamine surrogate ring and Leu of GC376 fit into the S1 and S2 sites, respectively (FIG. 16B, E). The GC376-bound structures of PV 3Cpro and TGEV 3CLpro are similar overall to the corresponding apo crystal form (PV3Cpro [PDB accession no. 1L1N] and TGEV 3CLpro [PDB accession no. 2AMP]). Hydrogen bonding interactions between PV 3Cpro or TGEV 3CLpro and GC376 are shown in FIGS. 17C and F. For the PV 3Cpro-GC376 complex, the hydrogen bond interactions between amino acid residues His 40, Leu 127, Gly 128, Thr 142, His 161, Val 162, and Gly 164 in the protease and the compound are shown in FIG. 17C. Superposition of residues Ala 7 to Leu 174 of apo-PV 3Cpro with those of the PV 3Cpro-GC376 complex yielded an RMSD of 0.83 Å between the Ca atoms. The largest differences that occur upon ligand binding were observed in the loops containing Leu 127, Gly 128, and Thr 142 (FIG. 16B). Leu 127 and Gly 128 undergo a conformational change to accommodate a water-mediated hydrogen bond with the compound, and Thr 142 moves to form a hydrogen bond with the pyrrolidine ring of GC376 (FIG. 16B). For the TGEV 3CLpro-GC376 complex, the hydrogen bond interactions between amino acid residues Thr 47, Phe 139, His 162, His 163, and Glu 165 in the protease and the compound are shown in FIG. 3I. The interactions between PV 3Cpro and GC376 also lead to conformational changes in loops containing Leu 127, Gly 128, and Gly 164 to accommodate hydrogen bonding. Like NV 3CLpro, the inhibitor was converted to the aldehyde form, which created a covalent bond with Cys 147 or Cys 144 in PV 3Cpro or TGEV 3CLpro, respectively. Water-mediated contacts between the protein and inhibitor were observed for PV 3Cpro and TGEV 3CLpro, as shown in FIG. 17. The B factors for these water molecules were 28.7 $Å^2$ and 36.5 $Å^2$ for PV 3Cpro, similar to the average B factor for all atoms in the model (22.7 $Å^2$). For TGEV 3CLpro, a single water-mediated contact was observed in a similar position in 3 of the 4 subunits. The Bfactors for these water molecules were 34.8 $Å^2$, 35.3 $Å^2$, and 30.8 $Å^2$ (subunits A, B, and C respectively), comparable to the average B factors for all atoms (31.9 $Å^2$). In addition, the water molecules fit well to the electron density maps, with no residual positive or negative density observed in the $F_o$-$F_c$ map following refinement.

8. In Vitro ADMET.

Overall in vitro ADMET profiles for GC373, GC375 and GC376 were determined (Cerep Inc). Metabolic stability studies showed that 20-56% of the compounds were metabolized in 30 min when incubated with human liver microsomes, which was further characterized with individual CYP inhibition assay. All compounds were not toxic up to 100 μM in cell viability assay with HepG2 cells. No cardiac toxicity was observed up to 100 μM.

9. Oral Bioavailability Studies in Rats.

Following the intravenous (IV) or oral (PO) administration of each compound at 20 mg/Kg (body weight) in rats, blood samples were obtained at 0.5, 1, 4, 8, 12, 16 and 24 h. Bioavailability data for the compounds is presented in FIG. 18. Most of GC376 was converted to the aldehyde form (GC373) in rat plasma when administered via VI and PO routes. Compounds GC373 and GC376 exhibited low oral bioavailability with % F values of 3 and 4, respectively. GC376 had a higher Cmax by IV and higher AUC by IV and PO, which indicated that the bisulfite adduct improved in vivo PK profiles. The oral availability of GC375 was fair (% F 16), and overall in vivo PK profiles were better than for the aldehyde counterpart (GC373), suggesting that the ketoamide residue may be important in improving PK parameters in animals.

10. Animal Studies.

We investigated if fecal norovirus shedding in human norovirus-inoculated gnotobiotic (Gn) pigs is altered the by treatment with GC376. Seven day-old piglets were randomly assigned to one of three groups: human norovirus HS194 strain (HuNoV, GII.4 strain)-inoculated (n=4) with GC376 treatment, HuNoV-inoculated (n=4) with mock treatment (DMSO), and negative control (n=2). The piglets (body weight 1-1.5 kg) were treated orally with 25 mg/kg of GC376 or mock treatment twice a day for 10 days and approximately 12.5 mg/kg twice a day for 5 more days. On day 2 after antiviral treatment, they were inoculated orally with $1.0 \times 10^{10}$ genome equivalent (GE) of Human norovirus (GII.12 HS206). Rectal swabs were collected daily from each animal throughout the experiment, and fecal virus shedding and clinical signs were monitored daily until virus was not detectable by real-time qRT-PCR. The Table below summarizes the results.

TABLE 8

| Treatment groups (n = 2-4/group) | Mean onset of virus shedding (PID) (SEM) | Mean duration of virus shedding (SEM) | | | Mean $log_{10}$ viral titer/rectal swab (GE/ml) (SEM) | | |
|---|---|---|---|---|---|---|---|
| | | Tx (+) at PIDs 1-13 | Tx (−) at PIDs 14-27 | Overall duration of virus shedding at PID1-27 | Tx (+) at PIDs 1-13 | Tx (−) at PIDs 14-27 | Overall viral titer shed at PIDs 1-27 |
| GC376 + HuNoV | 2.3 (0.6)$^A$ | 7.5 (0.9)$^A$ | 0 (0)$^B$ | 7.5 (0.9)$^A$ | 4.98 (0.09)$^B$ | <4.70 (0)$^{a,B}$ | 4.86 (0.05)$^B$ |
| HuNoV only | 4.5 (1.3)$^A$ | 8.5 (1.3)$^A$ | 8.0 (1.3)$^A$ | 16.5 (2.5)$^A$ | 5.01 (0.04)$^A$ | 4.93 (0.05)$^A$ | 4.97 (0.03)$^A$ |
| No HuNoV, no antiviral | 0 (0)$^B$ | 0 (0)$^B$ | 0 (0)$^B$ | 0 (0)$^B$ | <4.70 (0)$^B$ | <4.70 (0)$^B$ | <4.70 (0)$^B$ |

*The limit of viral RNA detection in the qRT-PCR assay was 4.7 $log_{10}$ GE/ml. Virus titers that were undetectable during the shedding period were assigned as a value of 4.7 $log_{10}$ GE/ml for statistical analysis.
**One-way ANOVA and the Tukey's test were used for statistical analysis, and different capital letters denote significant differences among groups.

Figures 19, 20:
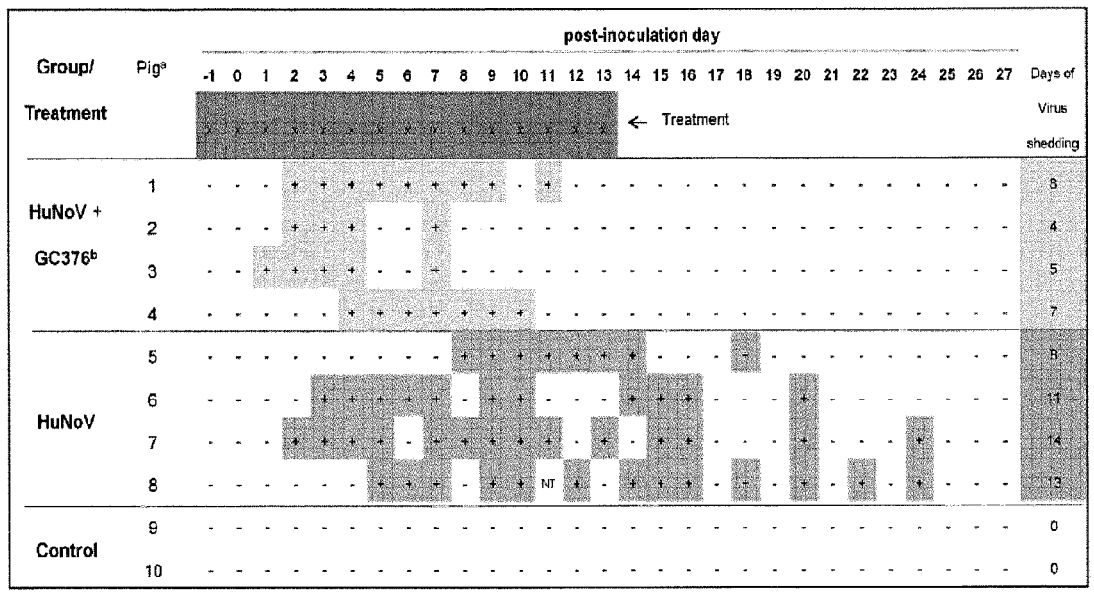
FIG. 19 is a table showing the virus shedding patterns in the feces of HuNoV-inoculated Gn pigs (1×10$^{10}$ GE/pig) with or without oral treatment of GC376.
FIG. 20 is a table of the selection of MNV-1 resistance against GC376.

As also shown in FIG. 19, oral treatment with GC376 significantly reduced the duration of virus shedding compared to untreated animals. The GC376-treated pigs shed significantly less fecal viral RNA for the treatment period, compared to HuNoV only group. After treatment was discontinued, the Gn pigs treated with GC376 showed no detectable viral RNA shedding as compared to HuNoV only. These results indicate that this compound with lower bioavailability showed antiviral activity against human norovirus, reducing viral shedding, even in this unoptimized dosage and frequency of a treatment regime.

The experiment was repeated using a higher dosage of GC376 (100 mg/kg/day). Piglets were randomly assigned to one of two groups: (1) GC376+HuNoV (n=3) and (2) 30% DMSO (vehicle)+HuNoV only (positive control) (n=2). On day 1 after oral inoculation with $8.0 \times 10^9$ GE of human norovirus (the GII.12 HS206), 7-day-old piglets (body weight 1-1.5 kg) were treated therapeutically orally with 100 mg/kg of GC376 once a day for 5 days. After antiviral treatment or HuNoV inoculation, clinical signs and fecal virus shedding were monitored daily through day 14. The results are summarized in the Table below.

TABLE 9

| Treatment groups n = 2-3/group | Mean onset of virus shedding (PID) (SEM)$^a$ | Mean duration of virus shedding (SEM)$^a$ | | | Mean log$_{10}$ viral titer/rectal swab (GE/ml) (SEM) | | |
|---|---|---|---|---|---|---|---|
| | | Tx (+) at PIDs 1-5 | Tx (−) at PIDs 6-14 | Overall duration of virus shedding at PIDs1-14 | Tx (+) at PIDs 1-5 | Tx (−) at PIDs 6-14 | Overall viral titer shed at PIDs 1-14 |
| GC376 + HuNoV | 2.7 (0.3) | 3.3 (0.3) | 4.0 (2.0) | 7.3 (1.9) | 5.28 (0.13)$^{b,A}$ | 5.11 (0.10)$^B$ | 5.17 (0.08)$^B$ |
| DMSO + HuNoV | 3.0 (0.5) | 3.0 (0.5) | 8.0 (0) | 11.0 (0.5) | 5.21 (0.19)$^A$ | 5.85 (0.09)$^A$ | 5.62 (0.11)$^A$ |

*More animals are required for statistical analysis of onset and duration of virus shedding.
**The limit of viral RNA detection in the qRT-PCR assay was 4.7 log$_{10}$ GE/ml. Virus titers that were undetectable during the shedding period were assigned as a value of 4.7 log$_{10}$ GE/ml for statistical analysis.
***One-way ANOVA and the Tukey's test was used for statistical analysis, and different capital letters denote significant differences among groups The results show that after treatment was discontinued, the Gn pigs treated with GC376 had significantly lower fecal viral RNA titers as compared to positive control pigs treated with 30% DMSO (vehicle). The results indicate that the oral administration of GC376 significantly reduced the viral shedding levels (viral titers in fecal samples) and the duration of virus shedding in gnotobiotic pig model for norovirus infection in two independent trials.

11. Viral Resistance Studies Using MNV-1.

To study viral resistance, the selection of escaping mutants (MNV-1) against GC376 was performed by passaging the virus in the presence of the drug up to 20 passages. Initial IC50 values determined at approximately 6.2-7.1 μM increased up to 10-fold at passage number 15 (FIG. 20). The sequence analysis of ORF1 of viruses collected at passage number 5 and 15 revealed 2 point mutations. The mutations are located at the dII β-sheet of 3CLpro, and at the P3 position near the cleavage site between VPg and 3CLpro (FIG. 21). The viral fitness of the mutated viruses decreased compared to wild-type viruses.

In order to optimize the identified norovirus 3CLpro series of inhibitors, a two-pronged strategy that is focused on the de-peptidization of identified peptidyl inhibitors to generate an array of α-ketoamide and α-ketoheterocycle peptidomimetics, including macrocyclic inhibitors that display superior drug-like characteristics will be employed. Specifically, the molecular properties that are important for oral bioavailability and favorable ADMET characteristics include a molecular weight of ≤500 Da, hydrogen bond donors≤5, sum of N and O hydrogen bond acceptors≤10, and c log P≤5. To further ensure that oral bioavailability is optimized, due consideration will be given to the number of rotatable bonds≤10, total hydrogen bond count (sum of donors and acceptors)≤12, and polar surface area (PSA) ≤140 Å present in the inhibitors. Reduced molecular flexibility (as measured by the number of rotatable bonds) and low PSA, are important predictors of good oral bioavailability, independent of molecular weight. Thus, incorporation of appropriate structural features into our lead compounds that are consistent with these guidelines will likely ensure that drug-likeness is optimized. Other important considerations that are an integral component of the optimization process for evaluating the quality of our lead compounds include maintaining good ligand efficiency (LE), a key molecular property defined as LE=1.4 log K$_i$ (or IC50)/n, where n is the number of heavy atoms. Maintaining a desirable ligand lipophilicity efficiency (LLE), defined as LLE=pK$_i$ (or pIC$_{50}$)−c log P is particularly important because of its profound influence on potency, PK, and toxicity.

12. Peptidomimetics. Inhibitor Design.

Norovirus 3CLpro is a chymotrypsin-like cysteine protease having a Cys-His-Glu catalytic triad and an extended binding site. The substrate specificity of norovirus 3CLpro has been determined using peptidyl chromogenic and fluorogenic substrates. Our foray in this area focused initially on the design of transition state inhibitors (FIG. 22) of NV 3CLpro that incorporate in their structure a recognition element (a peptidyl fragment) that is congruent with the known substrate specificity of the enzyme and a warhead (aldehyde, α-ketoamide, or α-ketoheterocycle) that interacts with the active site cysteine (Cys139) to form a reversible adduct (FIG. 2). NV 3CLpro shows a strong preference for a D/E-F-X-L-Q-G- sequence (where X is Q, H, or E) corresponding to the subsites $S_5$-$S_4$-$S_3$-$S_2$-$S_1$-$S_1$'- (cleavage is at the $P_1$-$P_1$' [Q-G] scissile bond). (See FIG. 1) The recognition element is responsible for binding and correct positioning of the inhibitor to the active site so that favorable binding interactions (H bonds, hydrophobic and dipole-dipole interactions) are optimal.

Since the primary specificity residue (P1) of norovirus 3CLpro is Gln, initial design considerations included the use of a glutamine surrogate for optimal synthetic tractability and design flexibility. Thus, a series of peptidyl aldehydes (Ia), α-ketoamides (Ib), α-ketoheterocycles (Ic) depicted in FIG. 22, and their bisulfite adducts were synthesized and screened against norovirus 3CLpro enzyme and in a cell-based replicon system. Our initial SAR studies in the peptidyl aldehyde series probed the nature of the P2 residue, since our structural studies suggested that the Leu side chain of the compounds did not optimally fill the S2 pocket. Thus we furthermore examined the effect of extending the recognition element (dipeptidyl versus tripeptidyl) on potency and permeability of the compounds. In addition, the S1' subsite (and beyond) was probed by varying the nature of the R$^1$ group in the α-ketoamide series (FIG. 22, structure (Ib)). Briefly, the results of those studies have demonstrated that (a) dipeptidyl inhibitors Ia-c inhibit norovirus 3CLpro enzyme, as well as norovirus replication in a cell-based replicon system; (b) a P2 residue with an R=n-butyl or cyclohexylmethyl side chain is preferred; (c) an array of structurally diverse R$^1$ groups are tolerated in the α-ketoamide series (FIG. 22, structure (Ib)); (d) a high resolution X-ray crystal structure of the NV 3CLpro-ligand complex with (Ia) has been determined (determination of the X-ray crystal structures of NV 3CLpro with α-ketoamide (Ib) (R¹=cyclopropyl) and α-ketoheterocycle (oxazole) are currently in progress); and (e) the bisulfite salt adduct of aldehyde (Ia) was found to show efficacy in the gnobiotic pig model of norovirus infection. This is the first time that transition state (TS) inhibitors and a high-resolution crystal structure of a TS inhibitor-enzyme complex, have been reported for norovirus 3CLpro. It is also the first time that bisulfite salt adducts of transition state inhibitors have been shown to inhibit norovirus 3CLpro enzyme, to exhibit anti-norovirus activity in a cell-based replicon system, and to have efficacy in an animal model of norovirus infection.

Example 4

Peptidyl α-Ketoamides and α-Ketoheterocyles

In this Example, a series of peptidyl α-ketoamides and α-ketoheterocycles (FIG. 22 Ib and Ic) were synthesized and then utilized in the in vitro inhibition of norovirus 3CLpro, as well as the inhibition of norovirus using the cell-based replicon system. The synthesized compounds were also used to probe the S' subsites of the enzyme.

Figure 24:
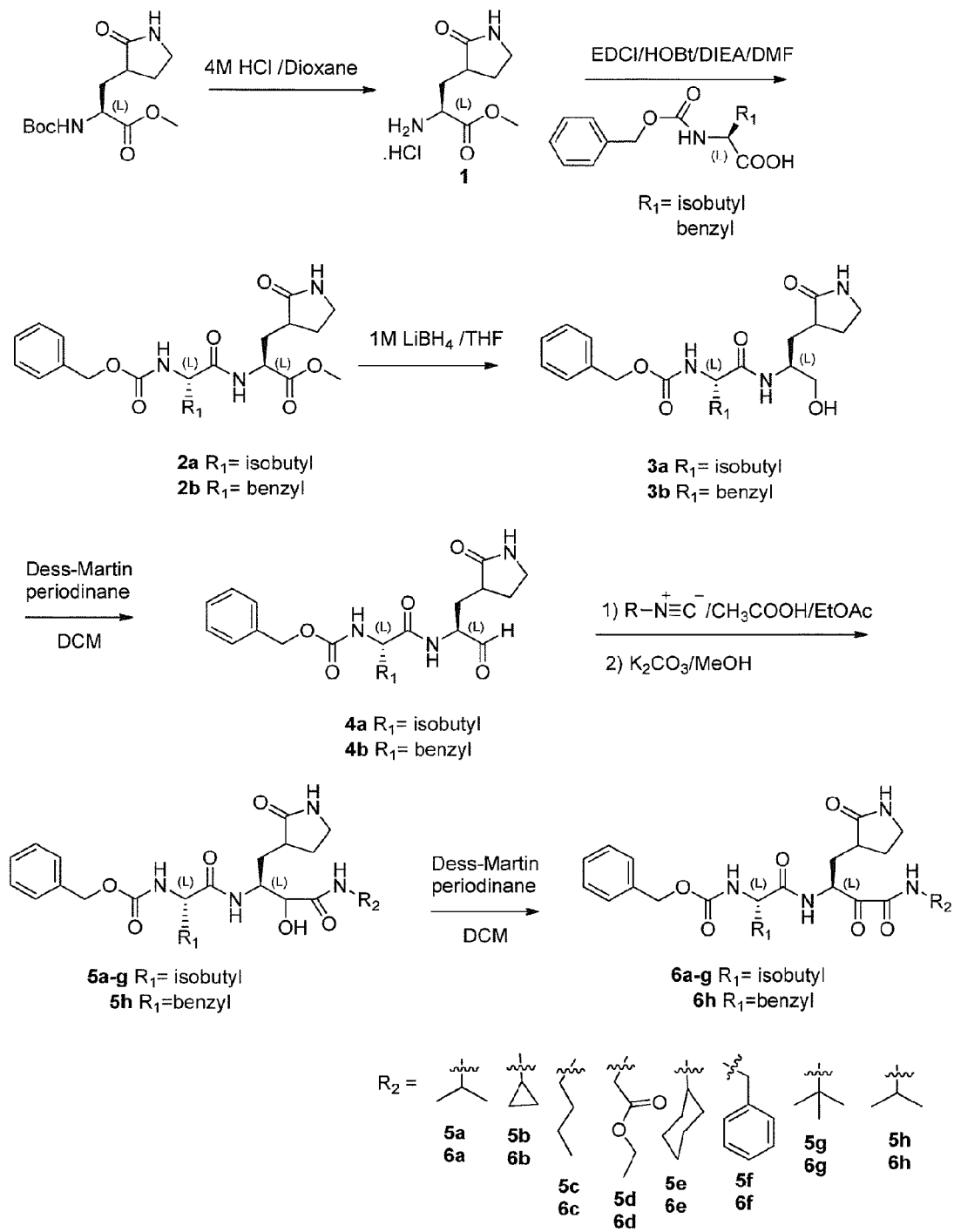
FIG. 24 is a reaction scheme showing the synthesis of the α-ketoamide peptidyl compounds in Example 4.
Figure 25:
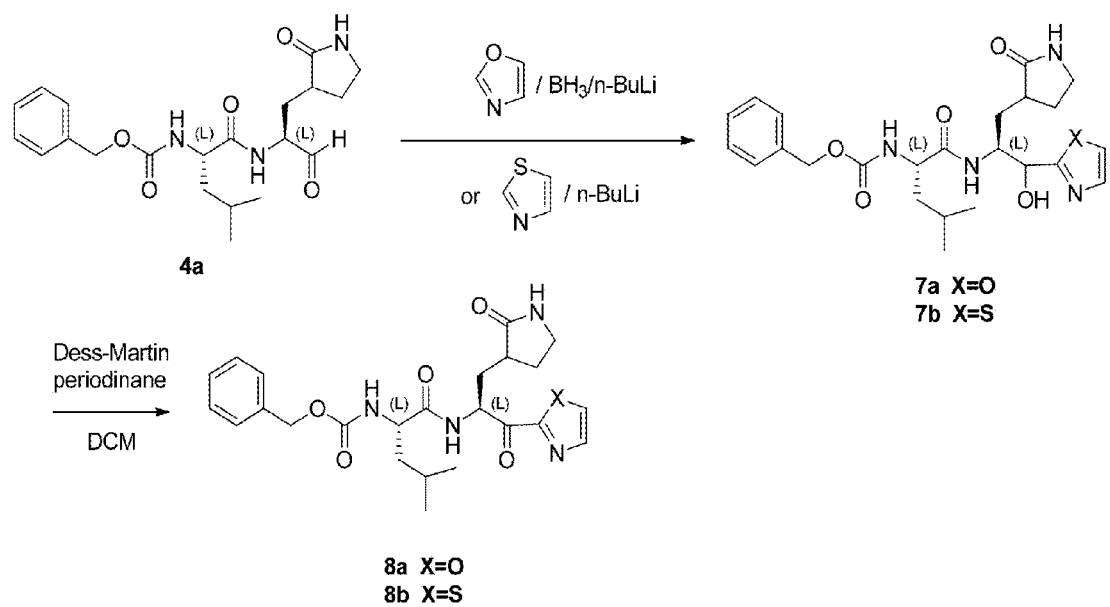
FIG. 25 is a reaction scheme showing the synthesis of the α-ketoheterocyle compounds in Example 4.

The syntheses of α-ketoamides 6a-h and α-ketoheterocycles 8a-b were carried out as illustrated in FIGS. 24 and 25, respectively. The resulting compounds as numbered herein are depicted in FIG. 23. Precursor and final compounds are numbered sequentially for ease of reference as illustrated in FIGS. 24 and 25, and described herein. The glutamine surrogate was utilized as the primary specificity ($P_1$) residue. The Boc-protected surrogate was synthesized and subsequently deprotected to yield compound 1 as illustrated in FIG. 24. EDCI-mediated coupling with Z-(L)-Leu-OH or Z-(L)-Phe-OH yielded compounds 2a-b, depicted in FIG. 24, which were reduced to the corresponding alcohols using lithium borohydride. Dess-Martin oxidation furnished aldehydes 4a-b, as depicted in FIG. 24, which were reacted with an array of structurally-diverse isonitriles to generate a series of precursor alcohols 5a-g and 5h, depicted in FIG. 24, which, upon oxidation, yielded the desired α-ketoamides 6a-h, depicted in FIG. 24. As depicted in FIG. 25, α-Ketoheterocycle 8a was synthesized by sequentially treating a solution of oxazole in THF with borane and n-butyl lithium, followed by reaction with aldehyde 4a depicted in FIG. 25, to yield precursor alcohol 7a which was subsequently oxidized to form α-ketoheterocycle 8a. As alternatively depicted in FIG. 25, reaction of compound 4a with the anion generated by reacting thiazole with n-butyl lithium, followed by Dess-Martin oxidation of the isolated precursor alcohol, yielded α-ketoheterocycle 8b. The activities of the precursor and generated compounds against norovirus were investigated in vitro and in a cell-based system and are summarized in FIG. 23, along with their chemical structures. Compound 6a corresponds to Formula (IV) in the description (also referred to herein as Inhibitor J or GC375). Compound 7a corresponds to Formula (VI), where X=O. Compound 7b corresponds to Formula (VI), where X=S. Compound 8a corresponds to Formula (V), where X=O. Compound 8b corresponds to Formula (V), where X=S.

The results indicate that α-ketoamides and α-ketoheterocycles inhibit norovirus 3CLpro in vitro, and also exhibit potent anti-norovirus activity in a cell-based system. The S' subsites of norovirus 3CLpro were also probed using a series of structurally-diverse α-ketoamides. It is evident from the results summarized in FIG. 23 that peptidyl α-ketoamides (compounds 6a-g) potently inhibit norovirus 3CLpro in vitro. Most importantly, the compounds exhibit potent anti-norovirus activity in a cell-based replicon system. In order to enhance further the pharmacological activity of the compounds by exploiting favorable binding interactions between the R group in (I) (assumed to be projecting toward the S' subsites) and the enzyme, the nature of the R group was varied. The results indicate that a wide range of R groups can be tolerated. The corresponding precursor alcohols (compounds 5a-h, FIG. 23) were substantially less active. Furthermore, replacement of P2 Leu with Phe decreased potency 4-fold (compare compounds 6a and 6h). Intriguingly, precursor alcohols 5a, 5h and 7b exhibited noteworthy activity in the cell-based replicon system despite their weak in vitro inhibitory activity against norovirus 3CLpro.

Figure 26:
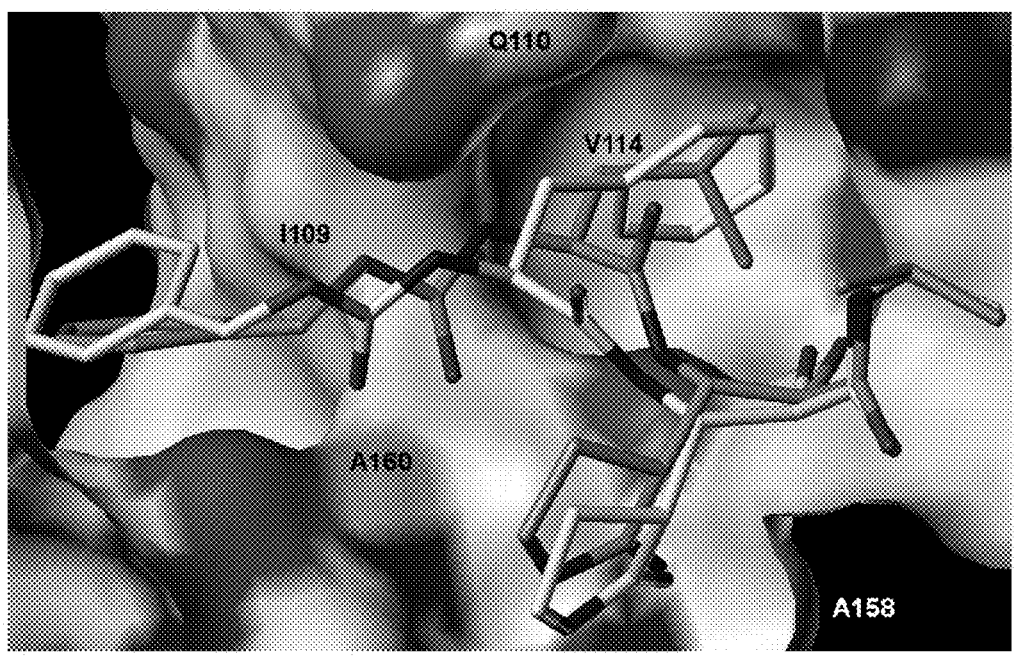
FIG. 26 illustrates predicted binding modes for norovirus 3CLpro inhibitors 6a and 6h synthesized in Example 4. The norovirus 3CLpro receptor is rendered as a Connolly surface, and is colored as follows: red=polar O, blue=polar N, cyan=polar H, white=polarized alkyl or aryl (C,H), and yellow=hydrophobic. The ligands are represented as CPK-colored sticks, with carbon atoms colored as follows: green=compound 6a and white=compound 6h. A selection of receptor residues with key ligand interactions are labeled.

In order to computationally predict binding modes for compounds 6a and 6h, a receptor structure for norovirus 3CLpro was prepared using the reported crystal structure by extracting the co-crystallized covalently-bound peptidyl ligand and all resolved water. The two inhibitors are capable of adopting similar low-energy conformations (FIG. 26) and engage in multiple favorable binding interactions with the enzyme, including lipophilic interactions involving the —($CH_2CH_2$)— segment of the glutamine surrogate with the corresponding —($CH_2CH_2$)— segment of Pro136 (above the viewing plane in FIG. 26), the Leu side chain in each inhibitor with His30 (also above plane), Ile109 and Val114, and interactions of the phenyl ring in the Cbz cap—partially occupying the S4 pocket—with Ile109. A network of hydrogen bonds involving Ala158 (backbone carbonyl), Gln110 (side chain amide) and Ala160 (backbone amide hydrogen) are also evident. Comparison of the binding modes of 6a and 6h suggests that the decline in potency in the latter may arise from the substitution of a more bulky group (benzyl) into the relatively small hydrophobic pocket (defined by Val114 in FIG. 26), which tends to shift the 6h binding mode outwards, disrupting the ligand H-bond with Gln110.

α-Ketoheterocycles 8a-b were also found to inhibit norovirus 3CLpro in vitro, with the oxazole derivative being about 4-fold more potent than the corresponding thiazole compound (FIG. 23). Both compounds were found to inhibit norovirus in a cell-based replicon system, with isoxazole 8a being the most effective ($ED_{50}$ 900 nM).

In summary, a series of structurally-diverse α-ketoamides and α-ketoheterocycles has been synthesized and shown to potently inhibit norovirus 3CLpro in vitro, as well as norovirus in a cell-based replicon system.

Example 5

Potent Inhibition of Feline Coronaviruses with Peptidyl Compounds Targeting Coronavirus 3C-Like Protease Feline coronavirus affects animals in the family Felidae, including cheetahs, wildcats, lions and leopards. Feline coronavirus serotype I is more prevalent than serotype II, and feline coronaviruses of both serotypes can cause mild or asymptomatic feline enteritis (FECV) and feline infectious peritonitis (FIP) in cats. FIP is a fatal disease in cats and currently one of the leading infectious causes of fatality among young cats in multiple cat households and shelters. Despite the fatal nature and increasing incidence of FIP, no effective prophylactic or therapeutic agent is currently available for FIP virus. In this Example, the antiviral effects of peptidyl protease inhibitors (GC373 and GC376) and cathepsin inhibitors against the replication of FECV and FIPV in cells is examined. The combined antiviral effects of GC373 and CA074-Me, a cathepsin B inhibitor, against FIPV in cell culture are also studied.

Materials and Methods

1. Compounds.

GC373 and GC376 compounds were synthesized as described above. Cathepsin B inhibitor CA074-Me [L-3-trans-((propylcarbamyl) oxirane-2-Carbonyl)-L-isoleucyl-L-proline methyl ester] and pan-cysteine cathepsin inhibitor E64d [(2S,3S)-trans-epoxysuccinyl-L-leucylamido-3-methylbutane ethyl ester] were purchased from Calbiochem (Darmstadt, Germany).

2. The Expression and Purification of TGEV 3CL Protease.

The 3CL proteases are highly conserved among all coronaviruses, and feline coronavirus 3CL protease is closely related TGEV 3CL protease. Therefore we cloned and expressed the TGEV 3CL protease for the FRET assay. The cDNA encoding the full length of 3CL protease of TGEV Miller strain was amplified with RT-PCR as previously described. The primers contained the nucleotide sequence of the 3CL protease for cloning as well as the nucleotides for 6 Histidine in the forward primer. The amplified product was subcloned to pET-28a(+) vector (GenScript, Piscataway, N.J.). The expression and purification of the 3CL protease was performed with a standard method described previously by our lab (Chang et al., 2012b; Takahashi et al., 2012; Tiew et al., 2011).

3. FRET-Based Protease Assay.

Our protease inhibitor compounds and commercial cathepsin inhibitors CA074-Me and E64d were prepared in DMSO as stock solutions (10 mM), and further diluted in assay buffer consisting of 20 mM HEPES, 0.4 mM EDTA, 30% glycerol, 120 mM NaCl, and 4 mM DTT at pH 6. The final concentrations of DMSO in the assay did not exceed 1.5% (v/v). TGEV 3CL protease at a final concentration of 0.1~0.2 μM and the substrate (Dabcyl-KTSAVLQS-GFRKME-Edans; SEQ ID NO:2) at 10 μM were used for the studies. The substrate was purchased from Bachem Americas, Inc (Torrance, Calif.). Compounds at various concentrations (0~50 μM) were pre-incubated with TGEV 3CL protease in 25 μl for 30 min at 37° C., and the same volume of substrate was added to a 96-well black plate. The mixtures were then incubated at 37° C. for 60 min, and fluorescence readings were obtained on a microplate reader at 360 nm excitation and 480 nm emission wavelengths. The relative fluorescence units (RFU) were calculated by subtracting background (substrate control well without protease) from the fluorescence readings. The dose-dependent FRET inhibition curves were fitted with variable slope (four parameters) using GraphPad Prism software (La Jolla, Calif.) in order to determine the compound concentration that gives a half-maximum response (IC50).

4. Cells, Viruses, and Reagents.

Crandell Rees feline kidney (CRFK) cells were maintained in minimal essential medium containing 2-5% fetal bovine serum and antibiotics (chlortetracycline [25 μg/ml], penicillin [250 U/ml], and streptomycin [250 μg/ml]). FIPV WSU 79-1146 and FECV WSU 79-1683 strains are the prototypes of serotype II FIPV or FECV, respectively, and were purchased from ATCC (Manassas, Va.).

5. Antiviral Effects of the Protease and Cathepsin Inhibitors Against FIPV and FECV in Cells.

Virus infection was performed as follows: solvent (0.1% DMSO), CA074-Me, E64d, GC373 or GC376 was added at various concentrations to two-day old monolayers of CRFK cells prepared in 6 well plates. The cells were further incubated in the presence of each compound for 1 hr at 37° C. Then FIPV-1147 or FECV-1683 was inoculated to the cells at a multiplicity of infection (MOI) of 0.05 or 5. The virus infected cells were incubated in the presence of a compound for up to 2 days, and the compound concentration that reduced the CPE by 50% ($ED_{50}$) was determined by the $TCID_{50}$ method.

a. Western Blot Analysis.

Cell lysates from CRFK cells were prepared by adding sodium dodecyl sulfate polyacrylamide gel electrophoresis (SDS-PAGE) sample buffer containing 2% β-mercaptoethanol and sonication for 20 sec. The proteins were then resolved in a 10% Novex Bis-Glycin gel (Invitrogen, Carlsbad, Calif.) and transferred to a nitrocellulose membrane. The transferred nitrocellulose membranes were incubated with primary antibodies to coronavirus nucleocapsid protein (Biocompare, Windham, N.H.) or β-actin as a loading control overnight, and then with the secondary antibodies conjugated with peroxidase for 2 hrs. Following incubation with a chemiluminescent substrate (SuperSignal West Pico Chemiluminescent Substrate, Pierce biotechnology, Rockford, Ill.), the signals were detected on X-ray film.

b. $TCID_{50}$ Method. A standard $TCID_{50}$ method with the 10-fold dilution of each sample was used for virus titration.

c. Nonspecific Cytotoxic Effect.

We determined the toxic dose for 50% cell death ($TD_{50}$) for each compound in CRFK cells. Confluent cells grown in 24-well plates were treated with various concentrations of compounds at up to 100 μM for cathepsin inhibitors and 500 μM for protease inhibitors for 24 or 48 hrs. Cell cytotoxicity was measured by a CytoTox 96® non-radioactive cytotoxicity assay kit (Promega, Madison, Wis.) and crystal violet staining. The in vitro therapeutic index (TI) was calculated by dividing $TD_{50}$ by $ED_{50}$.

6. Combination Treatment of the Cathepsin B Inhibitor, CA074-Me, and GC373.

The CRFK cells were incubated with GC373 (0.02~0.2 μM), CA074-Me (0.5~5 μM), or the combinations of GC373 (0.02~0.2 μM) and CA074-Me (0.5~5 μM) for 1 hr at 37° C. prior to inoculation of FIPV-1146 at an MOI of 0.05. After 24 hrs of incubation, virus replication was assessed with virus titration using the $TCID_{50}$ method. Drug-drug interactions were analyzed by the three-dimensional model of Prichard and Shipman, using the MacSynergy II software at 95% confidence limits. Theoretical additive interactions were calculated from the dose-response curve for each compound individually, and the calculated additive surface was subtracted from the experimentally determined dose-response surface to give regions of synergistic or antagonistic interactions. The resulting surface appears as horizontal plane at 0% of synergy if the interactions of two compounds are additive. Any peak above or below this plane indicates synergy or antagonism, respectively.

Results

1. Effects of the Protease Inhibitors on the Protease Activity in the FRET-Based Assay.

Figure 27:
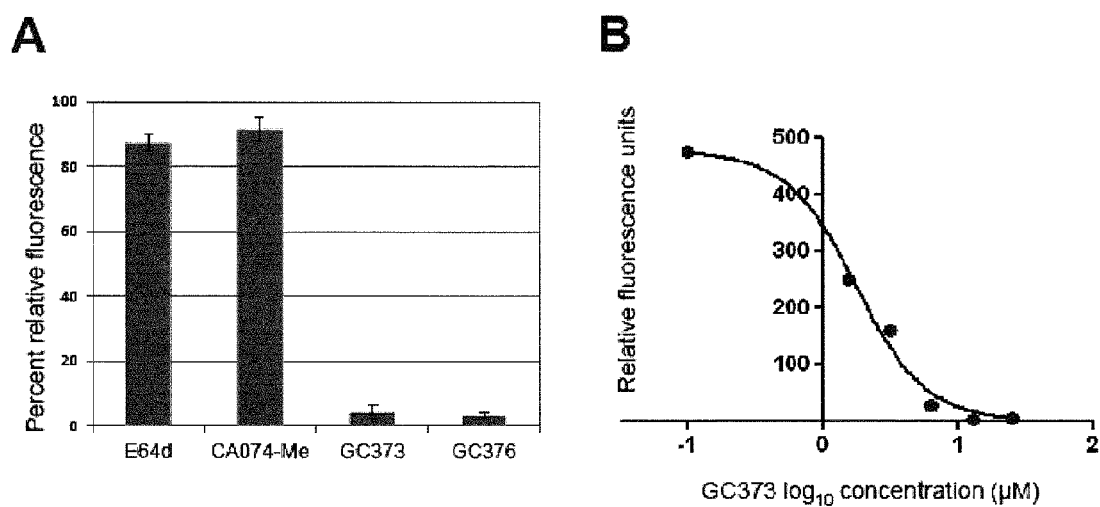
FIG. 27 shows the results of the FRET-based protease assay from Example 5. A. The effects of the 3CL protease inhibitors, GC373 and GC376, cathepsin B inhibitor CA074-Me, and pan-cysteine cathepsin inhibitor E64d on the activity of TGEV 3CL protease in the FRET-protease assay. TGEV 3CL protease was incubated with each compound at 50 µM for 20 min before the substrate was added to the mixture. Each bar represents the percent relative fluorescence (mean±standard error of the mean [SEM]). B. A plot of $\log_{10}$ GC373 concentration versus relative fluorescence units. TGEV 3CL protease was incubated with GC373 at increasing concentrations prior to addition of substrate. The fluorescence signals were detected by a spectrophotometer, and the data are then plotted as relative fluorescence units against the log concentrations of the compound.

The protease inhibition assay was performed using the florescence substrate derived from a cleavage site of SARS-CoA (Bachem Americas, Inc., Torrance, Calif.) to examine the inhibition of the 3CL protease by GC373 and GC376. The inhibitory effects of each compound at 50 μM (final concentration) on the activity of TGEV 3CL protease are shown in FIG. 27A. Cathepsin B inhibitor CA074-Me and pan-cysteine cathepsin inhibitor E64d were included as controls. GC373 and GC376 remarkably inhibited the activity of TGEV 3CL protease at 50 uM, but the cathepsin inhibitors did not (FIG. 27A). The dose-dependent inhibition of TGEV 3CL protease activity by GC373 is shown in FIG. 27B. The IC50 values of GC373 and GC376 against 3CL protease determined in the FRET assay were 0.98 µM and 0.82 µM, respectively.

2. Effects of the Protease and Cathepsin Inhibitors Against the Replication of Feline Coronaviruses in Cells.

Figure 28:
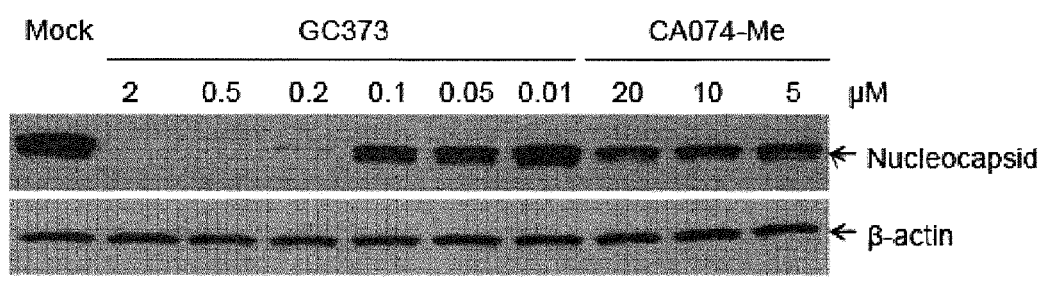
FIG. 28 is an image of the Western blot analysis of the effects of GC373 and CA074-Me on the accumulation of coronavirus nucleocapsid protein in CRFK cells infected with FIPV-1146. CRFK cells were treated with 0.1% DMSO, GC373 or CA074-Me for 2 hrs, followed by virus infection at an MOI of 5, and further incubated for 12 hrs. Cell extracts were analyzed by Western blot for expression of coronavirus nucleocapsid protein and β-actin was loaded as an internal control.

The antiviral effects of the protease and cathepsin inhibitors were studied in cell culture. The replication of FECV-1683 and FIPV-1146 were markedly inhibited by the presence of GC373, GC376, CA074-Me, or E64d (Table 10, FIG. 28). However, suppression of virus replication by the protease inhibitors was more potent than CA074-Me and E64d at 24 and 48 hrs, indicated by the $ED_{50}$ values (Table 10). Notably, the antiviral activities of CA074-Me and E64d decreased substantially over time (Table 10).

TABLE 10

| | Inhibition [$ED_{50}$ (µM)] against FIPV and FECV* | | | |
|---|---|---|---|---|
| | FECV-1683 | | FIPV-1146 | |
| | 24 hrs | 48 hrs | 24 hrs | 48 hrs |
| GC373 | 0.04 ± 0.01 | 0.09 ± 0.01 | 0.07 ± 0.04 | 0.43 ± 0.35 |
| GC376 | 0.17 ± 0.11 | 0.28 ± 0.10 | 0.15 ± 0.05 | 0.30 ± 0.10 |
| CA074-Me | 4.0 ± 0.71 | >10 | 2.5 ± 1.4 | >10 |
| E64d | 2.3 ± 0.28 | >10 | 1.45 ± 0.49 | >10 |

*The mean and standard error of the mean (SEM) of the $ED_{50}$ values for virus inhibition at 24 and 48 hr post infection are summarized. CRFK cells were incubated with each compound for 2 hrs before virus infection at an MOI of 0.05 and further incubated in the presence of each compound for up to 48 hrs. Virus titers were determined using the $TCID_{50}$ method for the calculation of the $ED_{50}$ values.

The antiviral effects of the protease inhibitors were selective; they were not active against unrelated viruses such as influenza virus and porcine respiratory and reproductive syndrome virus (data not shown). The antiviral activity of GC373 and GC376 was not due to nonspecific cytotoxicity since the protease inhibitors did not show any cytotoxicity in various cells even at 500 µM. The cathepsin inhibitors CA074-Me and E64d also did not show any toxicity at 100 µM. The in vitro therapeutic indices calculated from the ratio of $ED_{50}/TD_{50}$ of cathepsin and protease inhibitors are at least 25 and 2,900, respectively, at 24 hr post virus infection. These results demonstrate that the replication of FIPV and FECV is effectively inhibited by the protease inhibitors with an excellent safety margin in cells.

3. Effects of the Combined Treatment of GC373 and CA074-Me in the Replication of FIPV.

Figure 29:
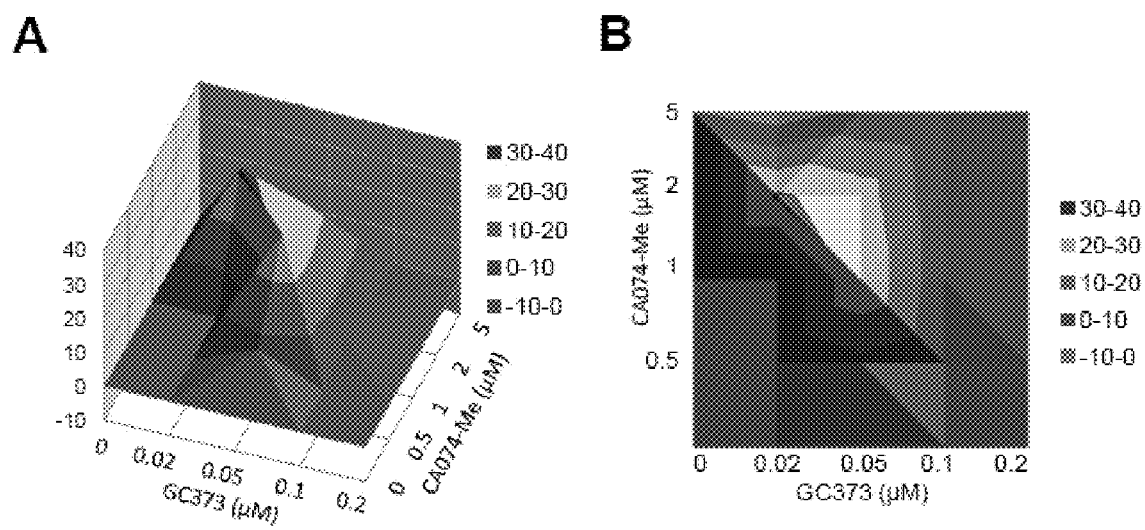
FIG. 29 shows the Three-dimensional plots showing the interaction of GC373 and CA074-Me on the replication of FIPV-1146. A and B. CRFK cells were incubated with CA074-Me (0.5~5 µM), GC373 (0.02~0.2 µM) or combinations of CA074 and GC373 for 2 hrs before virus was inoculated in the cells at an MOI of 0.05. The cells were further incubated in the presence of each compound for 24 hrs, and virus replication was measured by the $TCID_{50}$ method. Drug-drug interactions were analyzed by the three-dimensional model of Prichard and Shipman, using the MacSynergy II software at a 95% confidence interval. Surface above the plane of 0% synergy in the plot indicate synergy. B. Contour plots (two-dimensional representations of the data) for easier identification of the concentration ranges where statistically significant synergistic or antagonistic effects occurred.

Combination treatment of GC373 and CA074-Me was performed to investigate the interactions of the two compounds with different modes of inhibition against the replication of FIPV. The effects of combination were determined to be strongly synergistic as analyzed in a mathematical model based on the MacSynergy. Antiviral synergy was observed between GC373 and CA074-Me with an average $Synergy_{95}$ volume of 99.3 µM²% at a 95% confidence interval over two experiments (FIGS. 29A and B, and Table 11). Absolute values over 25 µM²% indicate significant values of synergy. For example, when virus-infected CRFK cells were treated with GC373 at 0.05 µM or CA074-Me at 1 each resulted in a 0.5 $log_{10}$ reduction of virus titers; in contrast, the combination of the two led to a 2 $log_{10}$ viral titer reduction, which was much more effective than either compound alone (indicated as synergy % in Table 11).

TABLE 11

| CA074-Me (µM) | GC373 (µM) | | | | | Synergy volume* | Antagonism volume* |
|---|---|---|---|---|---|---|---|
| | 0 | 0.02 | 0.05 | 0.1 | 0.2 | | |
| 5 | 0 | −5.78 | 1.87 | 0 | −0.0004 | 99.3 | −5.79 |
| 2 | 0 | 31.45 | 25.23 | 1.94 | 0 | | |
| 1 | 0 | 0 | 28.95 | 2.56 | 0 | | |
| 0.5 | 0 | n/a | 7.28 | 0 | 0 | | |
| 0 | 0 | 0 | 0 | 0 | 0 | | |

*Synergy/antagonism volumes were calculated at the 95% confidence level (µM² %).

DISCUSSION

Cathepsin inhibitors CA074-Me and E64d significantly inhibited the replication of FIPV at 24 hrs, although their potency was 13~100-fold lower than that of the protease inhibitors. However, a rapid loss of activity of CA074-Me and E64d was observed over time in cell culture without daily addition of the compound, compared to the protease inhibitors. The shorter duration of the activity of cathepsin inhibitors against viral replication is speculated to be viruses overcoming the antiviral blockade imposed by inhibition of cathepsin activity by resynthesis of uninhibited cathepsins or the relative instability of the cathepsin inhibitors in media. The antiviral effects of non-specific cathepsin inhibition by E64d against FIPV and FECV was more potent than the inhibition of cathepsin B at 24 hrs post infection, which may be explained by differences in affinity for the protease, stability of compounds, or potential presence of cathepsins other than cathepsin B that are able to process the viral polyproteins.

Since our protease inhibitors and CA074-Me act on different targets, we subsequently investigated the effects of the combined treatment of GC373 and CA074-Me against FIPV in cells. The analysis of the drug-drug combination at the 95% confidence interval by MacSynergy software showed the synergy volume of 99.3 µM²%. Only small volume of antagonism (−5.79 µM²%) was observed when a high concentration of CA074-Me (5 µM) were added to the cells containing GC373. At high concentrations, synergic activity was reduced as the antiviral response by single treatment reached high, and the synergy was most evident at mid range of compound concentrations used. We found no significant synergy of drug cytotoxic effects at the concentrations used. Our results showed the entry blocker and the protease inhibitor that work at the different stages of virus life cycle act synergistically at the concentrations shown. The favorable drug-drug interactions observed with FIPV suggest a potential use of combination of compounds that target the host factor involved in virus entry and the virus protease for feline coronavirus infection.

In summary, the protease inhibitors used in this study were found to be highly effective against FIPV and FECV in cells and the antiviral effects of those protease inhibitors were more profound than inhibition of cathepsins. Strong synergic effects were observed in combination treatment of a cathepsin B inhibitor and our protease inhibitor. These findings underscore the effectiveness of the inventive protease inhibitors for feline coronavirus infection and potential use of protease inhibitors as a single therapeutic agent or in combination with cathepsin B inhibitors.

Example 6

Tripeptidyl Compounds

In this example, tripeptidyl compounds (NPI52 (aka Formula VII) and NPI59 (aka Formula VIII)) were synthesized and then tested for their effect on the replication of calicivirus (norovirus), coronavirus and picornavirus in cell culture.

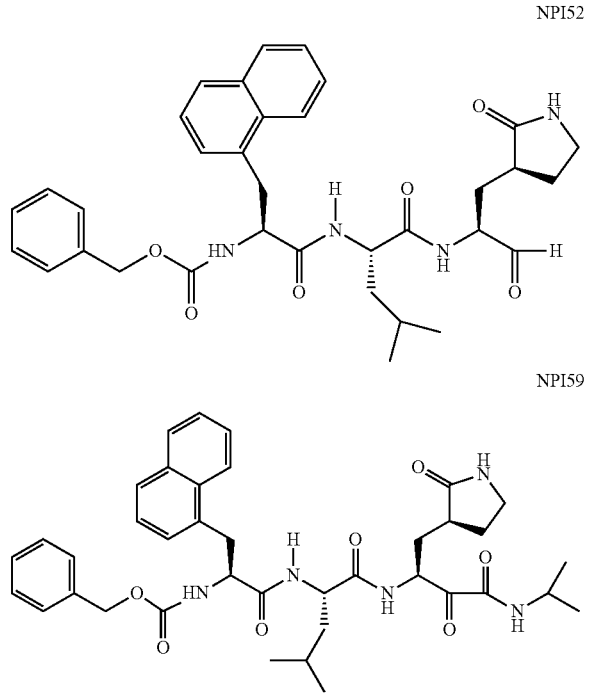

Tripeptide Synthesis

Figure 30:
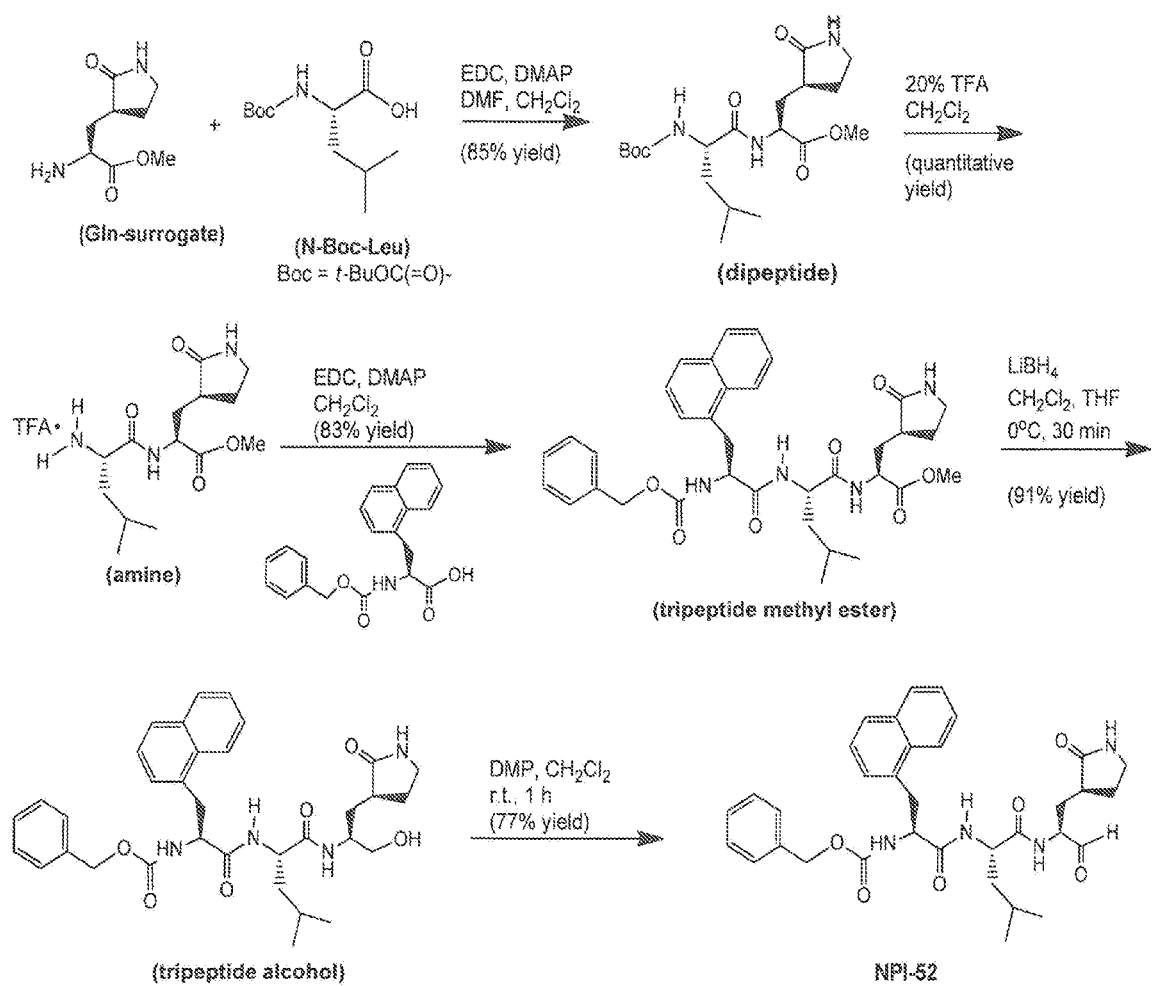
FIG. 30 illustrates the reaction scheme for synthesizing tripeptidyl compound NPI52.

NPI52 was synthesized via a sequence of peptide synthesis shown in FIG. 30. The synthesis of tripeptide NPI52 started from a coupling reaction of glutamine surrogate and N-Boc-L-leucine. To a solution of 80 mg (0.36 mmol) glutamine surrogate, 98 mg (0.39 mmol) N-Boc-L-leucine, 0.14 g (0.72 mmol) EDC, and 88 mg (0.72 mmol) DMAP in 5 mL dichloromethane under argon was added 1 mL DMF. The resulting solution was stirred at room temperature for 12 h, diluted with water and extracted three times with dichloromethane. The combined extract was washed with water and brine, dried (MgSO$_4$), concentrated, and column chromatographed on silica gel using a 15:1 mixture of dichloromethane and methanol as eluant to give 0.12 g (85% yield) dipeptide, as shown in FIG. 30. $^1$H NMR (400 MHz, CHLOROFORM-d) δ ppm 0.95 (dd, J=6.05, 3.71 Hz, 6H) 1.34-1.53 (s, 9H) 1.56-1.91 (m, 5H) 2.20-2.31 (m, 1H) 2.31-2.52 (m, 4H) 3.24-3.41 (m, 2H) 3.65-3.78 (s, 3H) 4.31 (m, 1H) 4.49 (td, J=7.42, 3.51 Hz, 1H) 5.20 (d, J=8.59 Hz, 1H) 6.98 (br. s., 1H) 7.87 (d, J=7.03 Hz, 1H); $^{13}$C NMR (100 MHz, CHLOROFORM-d) δ ppm 180.0, 173.6, 172.5, 155.9, 80.0, 53.0, 52.6, 51.3, 42.5, 40.7, 38.5, 33.3, 28.5, 28.3, 24.8, 23.1, 22.3. MS calcd for C$_{19}$H$_{33}$N$_3$O$_6$ (M+Na)$^+$ 422.2, found 422.1.

A solution of 0.12 g (0.30 mmol) dipeptide synthsized above in 10 mL 20% TFA in dichloromethane was stirred at room temperature for 1 h, concentrated on a rotary evaporator to yield an oil. As shown in FIG. 30, chloroform (10 mL) was added to the oil and concentrated to dryness leaving 130 mg (quantitative yield) of amine as a TFA salt. $^1$H NMR (400 MHz, CHLOROFORM-d) δ ppm 0.99 (dd, J=10.15, 6.25 Hz, 6H) 1.65-1.95 (m, 5H) 1.95-2.16 (m, 2H) 2.44 (br. s., 1H) 2.69 (br. s., 1H) 3.46 (d, J=7.42 Hz, 2H) 3.76 (s, 3H) 4.09 (br. s., 1H) 4.44-4.54 (m, 1H) 7.49 (br. s., 1H) 8.67 (d, J=5.86 Hz, 1H).

Without purification, 0.42 g (1.0 mmol) amine.TFA was mixed with 0.35 g (1.0 mmol) N-(benzyloxycarbonyl)-L-1-naphthylalanine, 0.38 g (2.0 mmol) EDC, and 0.24 g (2.0 mmol) DMAP, as shown in FIG. 30, followed by addition of 10 mL dichloromethane under argon. The resulting solution was stirred at room temperature for 18 h, diluted with water and extracted three times with dichloromethane. The combined extract was washed with water and brine, dried (MgSO$_4$), concentrated, and column chromatographed on silica gel using a mixture of 40:1 dichloromethane and methanol as eluant to give 0.53 g (83% yield) tripeptide methyl ester. $^1$H NMR (400 MHz, CHLOROFORM-d) δ ppm 0.78-1.03 (m, 6H) 1.38-1.89 (m, 5H) 2.09-2.47 (m, 3H) 3.11-3.31 (m, 2H) 3.39 (dd, J=14.45, 7.81 Hz, 1H) 3.55-3.79 (m, 4H) 4.45 (br. s., 1H) 4.67 (m, 2H) 4.91-5.06 (s, 2H) 5.60-5.71 (m, 1H) 6.95 (d, J=9.76 Hz, 1H) 7.09-7.37 (m, 8H) 7.40-7.54 (m, 2H) 7.66-7.87 (m, 2H) 8.01-8.18 (m, 2H), $^{13}$C NMR (100 MHz, CHLOROFORM-d) δ ppm 180.1, 172.7, 172.4, 171.4, 156.3, 136.3, 134.1, 132.9, 132.3, 129.1, 128.7, 128.4, 128.2, 128.0, 127.9, 126.3, 126.0, 125.5, 123.9, 67.2, 56.0, 52.6, 51.9, 51.4, 42.2, 40.8, 38.6, 35.5, 33.3, 28.2, 24.8, 23.1, 22.3. MS calcd for C$_{35}$H$_{42}$N$_4$NO$_7$ (M+Na)$^+$ 653.0, found 653.2.

As depicted in FIG. 30, to a cold (0° C.) solution of the tripeptide methyl ester synthesized above in 10:1 dichloromethane and THF under argon was added 27 mg (1.2 mmol) lithium borohydride. The solution was stirred at 0° C. for 30 min, diluted with water and dichloromethane (50 mL each), and the water layer was extracted with dichloromethane four time. The combined extract was washed with brine, dried (MgSO$_4$), and concentrated to yield 0.46 g (91% yield) tripeptide alcohol as a crude product, as shown in FIG. 30. $^1$H NMR (400 MHz, CHLOROFORM-d) δ ppm 0.78-0.92 (m, 6H) 1.33-1.54 (m, 5H) 1.60-1.79 (m, 3H) 2.18-2.37 (m, 3H) 3.20-3.29 (m, 2H) 3.32-3.72 (m, 5H) 3.86-3.96 (m, 1H) 4.46 (d, J=3.12 Hz, 1H) 4.54-4.63 (m, 1H) 4.96-5.06 (m, 2H) 5.46 (d, J=7.03 Hz, 1H) 5.94 (s, 1H) 6.92 (d, J=6.64 Hz, 1H) 7.19-7.40 (m, 7H) 7.43-7.61 (m, 2H) 7.69-7.90 (m, 2H) 8.15 (d, J=8.59 Hz, 1H); MS calcd for C$_{34}$H$_{42}$N$_4$O$_6$ (M+Na)$^+$ 625.3, found 625.2.

Without purification, 0.46 g (0.76 mmol) the tripeptide alcohol in 15 mL dichloromethane under argon was mixed with 0.64 g (1.51 mmol) Dess-Martin periodinane (DMP), as shown in FIG. 30. The reaction mixture was stirred at room temperature for 1 h, concentrated on a rotary evaporator to ~2 mL, and subjected to a silica gel column. After elution with a gradient mixture of dichloromethane and acetone, 0.35 g (77% yield) aldehyde NPI52 was obtained. $^1$H NMR (400 MHz, CHLOROFORM-d) δ ppm 0.88 (dd, J=6.25, 1.95 Hz, 6H) 1.38-1.87 (m, 5H) 1.95-2.09 (m, 2H) 2.25-2.36 (m, 2H) 3.25 (d, J=7.81 Hz, 2H) 3.42 (d, J=14.25, 7.22 Hz, 1H) 3.64 (dd, J=14.06, 6.64 Hz, 1H) 4.23 (br. s., 1H) 4.56-4.68 (m, 2H) 5.01 (s, 2H) 5.60 (d, J=7.81 Hz, 1H) 6.50 (s, 1H) 7.01-7.11 (m, 1H) 7.19-7.37 (m, 7H) 7.44-7.53 (m, 2H) 7.69-7.77 (m, 1H) 7.80-7.87 (m, 1H) 8.15 (d, J=5.47 Hz, 2H) 9.39 (s, 1H), $^{13}$C NMR (100 MHz, CHLOROFORM-d) δ ppm 200.2, 180.1, 173.3, 171.4, 156.5, 136.2, 134.1, 132.8, 132.3, 129.1, 128.8, 128.5, 128.2, 128.1, 127.9, 126.7, 126.1, 125.6, 123.9, 67.3, 57.8, 56.0, 52.0, 41.9, 40.8, 38.4, 35.4, 29.9, 28.7, 25.0, 23.1, 22.1; MS calcd for C$_{34}$H$_{40}$N$_4$O$_6$ (M+Na)$^+$ 623.3, found 623.4.

Tripeptideketoamide NPI59 was synthesized from NPI52 and isopropyl isocyanide in ethyl acetate (EtOAc) and acetic acid (AcOH) at room temperature, as shown in FIG. 31. To a solution of 0.14 g (0.23 mmol) aldehyde NPI52 in 5 mL ethyl acetate and 2 drops of acetic acid was added 22 μL isopropyl isocyanide. After stirring the solution at room temperature for 12 h, the solution was concentrated to dryness, diluted with 5 mL of a 1:1 methanol and water, and the solution was stirred at room temperature for 3 h. The solution diluted with 5 mL of brine and extracted with ethyl acetate five times (15 mL each). The combined extract was washed with brine, dried (MgSO$_4$), concentrated to yield 0.13 g white solid hydroxyl amide. $^1$H NMR (400 MHz, CHLOROFORM-d) δ ppm 0.77-0.91 (m, 6H) 1.06-1.18 (m, 6H) 1.35-1.65 (m, 3H) 1.71 (br. s., 1H) 1.93-2.11 (m, 2H) 2.31 (br. s., 2H) 3.19 (d, J=10.93 Hz, 2H) 3.29-3.41 (m, 1H) 3.68 (d, J=13.28 Hz, 1H) 3.94-4.09 (m, 2H) 4.15 (br. s., 1H) 4.28-4.52 (m, 2H) 4.54-4.66 (m, 2H) 4.99 (br. s., 2H) 5.48-5.69 (m, 2H) 6.19 (br. s., 1H) 6.34 (br. s., 1H) 6.74-6.84 (m, 1H) 6.99 (br. s., 1H) 7.08-7.37 (m, 7H) 7.48 (d, J=7.03 Hz, 2H) 7.69-7.88 (m, 2H) 8.13 (d, J=8.20 Hz, 1H); MS calcd for C$_{38}$H$_{49}$N$_5$O$_7$ (M+Na)$^+$ 710.4, found 710.5.

Without purification, 0.13 g (0.19 mmol) of the hydroxyl amide in 8 mL dichloromethane under argon was mixed with 0.16 g (0.38 mmol) DMP and the reaction mixture was stirred at room temperature for 2 h. It was concentrated on a rotary evaporator to about 2 mL and subjected to a silica gel column chromatography eluting with a gradient mixture of dichloromethane and acetone to give 60 mg (46% yield) of ketoamide NPI-59 as a white solid, as shown in FIG. 31.

$^1$H NMR (400 MHz, CHLOROFORM-d) δ ppm 0.83-0.95 (m, 6H) 1.20 (dd, J=6.44, 3.32 Hz, 6H) 1.37-1.45 (m, 1H) 1.52-1.65 (m, 2H) 1.88-2.04 (m, 3H) 2.35-2.57 (m, 2H) 3.31 (d, J=7.81 Hz, 2H) 3.44 (dd, J=14.06, 7.42 Hz, 1H) 3.65 (dd, J=13.86, 6.05 Hz, 1H) 3.97-4.09 (m, 1H) 4.57-4.65 (m, 2H) 5.01 (s, 2H) 5.21 (br. s., 1H) 5.48 (d, J=7.42 Hz, 1H) 6.53 (s, 1H) 6.76-6.86 (m, 2H) 7.17-7.38 (m, 7H) 7.40-7.55 (m, 2H) 7.74 (d, J=7.81 Hz, 1H) 7.80-7.87 (m, 1H) 8.16 (d, J=8.20 Hz, 1H) 8.37 (d, J=5.86 Hz, 1H), $^{13}$C NMR (100 MHz, CHLOROFORM-d) δ ppm 195.5, 180.0, 172.3, 171.2, 158.7, 156.3, 136.3, 134.1, 132.8, 132.3, 129.1, 128.8, 128.4, 128.2, 128.1, 127.9, 126.7, 126.0, 125.6, 123.9, 67.3, 56.0, 53.7, 51.7, 42.1, 42.0, 40.9, 39.3, 35.4, 32.2, 28.4, 24.8, 23.1, 22.6, 22.5, 22.3; MS calcd for C$_{38}$H$_{47}$N$_5$O$_7$ (M+Na)$^+$ 708.3, found 708.4.

The synthesized peptides were then tested in cell culture as described in the Examples above. As shown by the results in FIG. 32, the cell culture system confirmed the broad-spectrum activity of these compounds which inhibits replication of various viruses.

---

The invention claimed is:

1. An antiviral compound selected from the group consisting of formulas II, III, IV, V, VI, VII, and VIII, or a pharmaceutically-acceptable salt thereof:

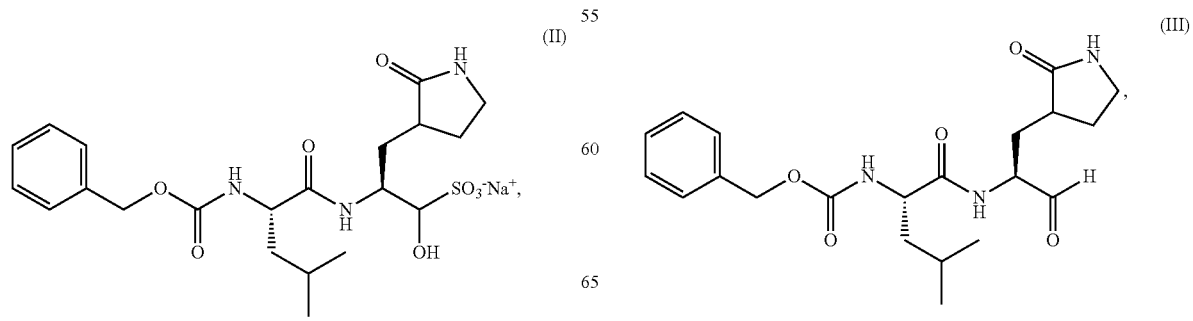

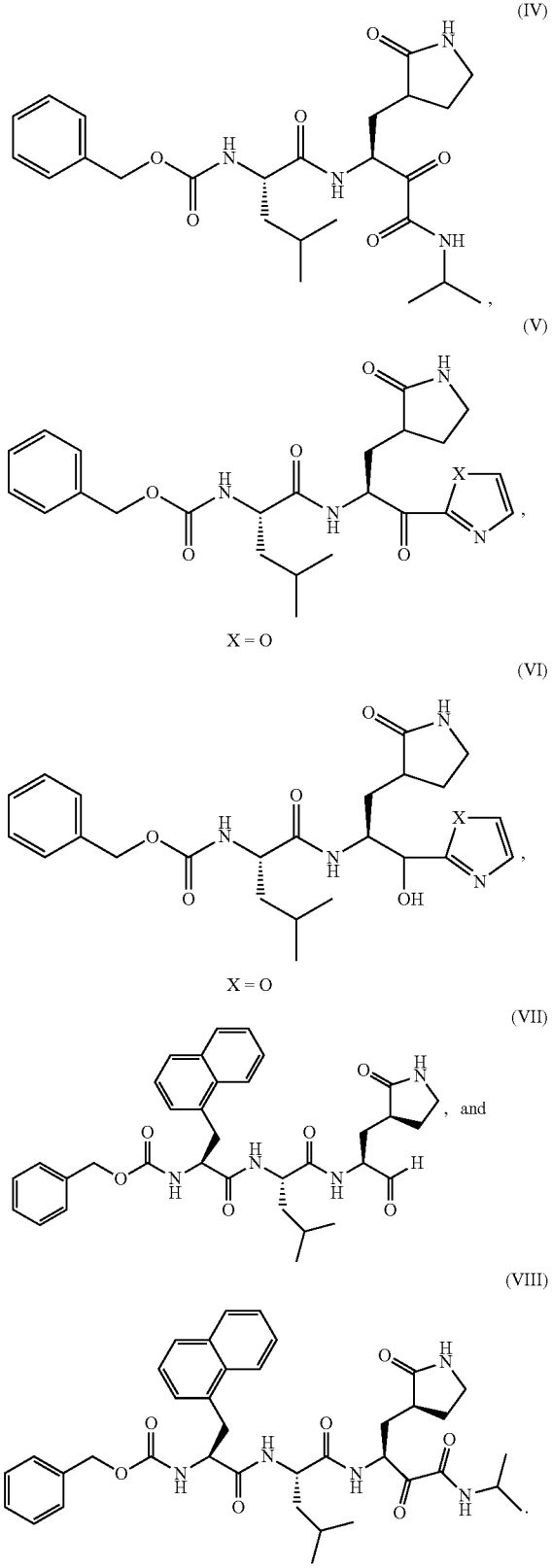

wherein the phenyl ring in the Cbz cap of any one of formulas II, III, IV, V, VI, VII, and VIII can be substituted or unsubstituted.

2. The compound of claim 1, wherein said compound inhibits viral replication of one or more viruses selected from the group consisting of caliciviruses, picornaviruses, and/or coronaviruses.

3. The compound of claim 2, wherein said compound inhibits 3C or 3C-like protease activity of said virus.

4. The compound of claim 1, wherein said compound has broad spectrum activity effective against multiple viruses.

5. A broad spectrum antiviral composition comprising a first antiviral compound according to claim 1 dispersed in a pharmaceutically-acceptable carrier.

6. The composition of claim 5, wherein said carrier is selected from the group consisting of sterile isotonic aqueous buffer, normal saline, phosphate buffered saline, DMSO, sterile water, oil-in-water emulsion, water-in-oil emulsion, and mixtures thereof.

7. The composition of claim 5, said composition comprising from about 5% to about 95% by weight of said antiviral compound, based upon the total weight of said composition taken as 100% by weight.

8. The composition of claim 5, further comprising a second antiviral compound, both of said compounds being dispersed in said pharmaceutically-acceptable carrier.

9. The composition of claim 8, wherein said second compound is an antiviral compound according to claim 1, said first compound being different from said second compound.

10. A kit comprising: an antiviral compound according to claim 1; and instructions for administering said compound to a subject in need thereof.

11. The kit of claim 10, wherein said compound is provided in unit dosage form.

12. The kit of claim 10, wherein said compound is provided in a first container, said kit further comprising a carrier in a second container; and instructions for preparing said antiviral compound for administration to said subject.

13. A method of treating a viral infection from one or more viruses selected from the group consisting of caliciviruses, picornaviruses, and/or coronaviruses in a subject, said method comprising administering to said subject a therapeutically-effective amount of a first antiviral compound according to claim 1.

14. The method of claim 13, wherein said compound has a therapeutic index of greater than about 500:1.

15. The method of claim 13, further comprising administering a second antiviral compound to said subject.

16. The method of claim 15, wherein said second compound is an antiviral compound according to claim 1, said first compound being different from said second compound.

17. The method of claim 15, wherein said first and second compounds are co-administered.

18. The method of claim 13, wherein said virus is selected from the group consisting of Norwalk virus, feline calicivirus, MD145, murine norovirus, vesicular exanthema of swine virus, rabbit hemorrhagic disease virus, enterovirus 71, poliovirus, coxsackievirus, foot-and-mouth disease virus, hepatitis A, porcine teschovirus, rhinovirus, human coronavirus, transmissible gastroenteritis virus, murine hepatitis virus, bovine coronavirus, feline infectious peritonitis virus, and severe acute respiratory syndrome coronavirus.

19. The method of claim 13, wherein said subject is suffering from a viral infection from a calicivirus, picornavirus, and/or coronavirus prior to said administering.

20. The method of claim 13, wherein said treatment comprises prophylactic administration.

* * * * *

SEQUENCE LISTING

```
<160> NUMBER OF SEQ ID NOS: 21

<210> SEQ ID NO 1
<211> LENGTH: 14
<212> TYPE: PRT
<213> ORGANISM: Artificial Sequence
<220> FEATURE:
<223> OTHER INFORMATION: Synthetic substrate

<400> SEQUENCE: 1

Glu Pro Asp Phe His Leu Gln Gly Pro Glu Asp Leu Ala Lys
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetic substrate

<400> SEQUENCE: 2

Lys Thr Ser Ala Val Leu Gln Ser Gly Phe Arg Lys Met Glu
1               5                   10

<210> SEQ ID NO 3
<211> LENGTH: 8
<212> TYPE: PRT
<213> ORGANISM: Artificial Sequence
<220> FEATURE:
<223> OTHER INFORMATION: Synthetic substrate

<400> SEQUENCE: 3

Gly Leu Arg Thr Gln Ser Phe Ser
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic substrate

<400> SEQUENCE: 4

Ala Pro Ala Lys Gln Leu Leu Asn
1               5
```

-continued

```
<210> SEQ ID NO 5
<211> LENGTH: 20
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (12)..(12)
<223> OTHER INFORMATION: n is any base or inosine

<400> SEQUENCE: 5
cgytggatgc gnttycatga                                               20

<210> SEQ ID NO 6
<211> LENGTH: 22
<212> TYPE: DNA
<213> ORGANISM: Artificial Sequence
<220> FEATURE:
<223> OTHER INFORMATION: PCR primer

<400> SEQUENCE: 6
cttagacgcc atcatcatty ac                                            22

<210> SEQ ID NO 7
<211> LENGTH: 20
<212> TYPE: DNA
<213> ORGANISM: Artificial Sequence
<220> FEATURE:
<223> OTHER INFORMATION: PCR probe
<220> FEATURE:
<221> NAME/KEY: misc_feature
<222> LOCATION: (9)..(9)
<223> OTHER INFORMATION: n is a or inosine
<220> FEATURE:
<221> NAME/KEY: misc_feature
<222> LOCATION: (12)..(12)
<223> OTHER INFORMATION: n is c, t, or inosine

<400> SEQUENCE: 7
agatygcgnt cncctgtcca                                               20

<210> SEQ ID NO 8
<211> LENGTH: 20
<212> TYPE: DNA
<213> ORGANISM: Artificial Sequence
<220> FEATURE:
<223> OTHER INFORMATION: PCR primer

<400> SEQUENCE: 8
actgcagtga ctggtgcttc                                               20

<210> SEQ ID NO 9
<211> LENGTH: 20
<212> TYPE: DNA
<213> ORGANISM: Artificial Sequence
<220> FEATURE:
<223> OTHER INFORMATION: PCR primer

<400> SEQUENCE: 9
ccgggtttat caacagaggt                                               20

<210> SEQ ID NO 10
<211> LENGTH: 24
<212> TYPE: DNA
<213> ORGANISM: Artificial Sequence
<220> FEATURE:
<223> OTHER INFORMATION: PCR probe
```

-continued

```
<400> SEQUENCE: 10
cctggtgtga tccaacctca gctg                                          24

<210> SEQ ID NO 11
<211> LENGTH: 18
<212> TYPE: DNA
<213> ORGANISM: Artificial Sequence
<220> FEATURE:
<223> OTHER INFORMATION: PCR primer

<400> SEQUENCE: 11
tgttcyagcc tgcgtggc                                                 18

<210> SEQ ID NO 12
<211> LENGTH: 21
<212> TYPE: DNA
<213> ORGANISM: Artificial Sequence
<220> FEATURE:
<223> OTHER INFORMATION: PCR primer

<400> SEQUENCE: 12
gaaacacgga cacccaaagt a                                             21

<210> SEQ ID NO 13
<211> LENGTH: 22
<212> TYPE: DNA
<213> ORGANISM: Artificial Sequence
<220> FEATURE:
<223> OTHER INFORMATION: PCR probe

<400> SEQUENCE: 13
tcctccggcc cctgaatgyg gc                                            22

<210> SEQ ID NO 14
<211> LENGTH: 20
<212> TYPE: DNA
<213> ORGANISM: Artificial Sequence
<220> FEATURE:
<223> OTHER INFORMATION: PCR primer

<400> SEQUENCE: 14
ttccgacgtg ctcgaacttt                                               20

<210> SEQ ID NO 15
<211> LENGTH: 21
<212> TYPE: DNA
<213> ORGANISM: Artificial Sequence
<220> FEATURE:
<223> OTHER INFORMATION: PCR primer

<400> SEQUENCE: 15
ccaacacggt tgtgacagtg a                                             21

<210> SEQ ID NO 16
<211> LENGTH: 16
<212> TYPE: DNA
<213> ORGANISM: Artificial Sequence
<220> FEATURE:
<223> OTHER INFORMATION: PCR probe

<400> SEQUENCE: 16
tcctgaggtc aatgca                                                   16

<210> SEQ ID NO 17
<211> LENGTH: 14
```

```
<212> TYPE: PRT
<213> ORGANISM: Norwalk virus

<400> SEQUENCE: 17

Leu Pro Asp Phe His Leu Gln Gly Pro Glu Asp Leu Ala Arg
1               5                   10

<210> SEQ ID NO 18
<211> LENGTH: 14
<212> TYPE: PRT
<213> ORGANISM: Norwalk virus

<400> SEQUENCE: 18

Gln Asp Glu Phe Gln Leu Gln Gly Pro Thr Tyr Asp Phe Asp
1               5                   10

<210> SEQ ID NO 19
<211> LENGTH: 14
<212> TYPE: PRT
<213> ORGANISM: Norwalk virus

<400> SEQUENCE: 19

Pro Ser Asp Ala Val Pro Glu Gly Lys Asn Lys Gly Lys Thr
1               5                   10

<210> SEQ ID NO 20
<211> LENGTH: 14
<212> TYPE: PRT
<213> ORGANISM: Norwalk virus

<400> SEQUENCE: 20

Asn Glu Lys Ile Asn Phe Glu Ala Pro Pro Thr Leu Trp Ser
1               5                   10

<210> SEQ ID NO 21
<211> LENGTH: 14
<212> TYPE: PRT
<213> ORGANISM: Norwalk virus

<400> SEQUENCE: 21

Glu Gly Glu Thr Ala Leu Glu Gly Gly Asp Lys Gly His Tyr
1               5                   10
```